(12) United States Patent
Yasuda et al.

(10) Patent No.: US 7,666,869 B2
(45) Date of Patent: Feb. 23, 2010

(54) NITROGEN-CONTAINING 5-MEMBERED RING COMPOUND

(75) Inventors: Kosuke Yasuda, Saitama (JP); Hiroshi Morimoto, Saitama (JP); Saburo Kawanami, Saitama (JP); Masataka Hikota, Shiki (JP); Takeshi Matsumoto, Saitama (JP); Kenji Arakawa, Saitama (JP)

(73) Assignee: Mitsubishi Tanabe Pharma Corp. (JP)

( * ) Notice: Subject to any disclaimer, the term of this patent is extended or adjusted under 35 U.S.C. 154(b) by 0 days.

(21) Appl. No.: 12/000,024

(22) Filed: Dec. 7, 2007

(65) Prior Publication Data

US 2008/0153821 A1   Jun. 26, 2008

Related U.S. Application Data

(62) Division of application No. 11/452,923, filed on Jun. 15, 2006, now Pat. No. 7,332,487, which is a division of application No. 10/398,485, filed as application No. PCT/JP01/08802 on Oct. 5, 2001, now Pat. No. 7,138,397.

(30) Foreign Application Priority Data

| Oct. 6, 2000 | (JP) | ............................. 2000/308528 |
| Oct. 12, 2000 | (JP) | ............................. 2000/312562 |
| Mar. 30, 2001 | (JP) | ............................. 2001/099251 |

(51) Int. Cl.
*A61K 31/535* (2006.01)
*A61K 31/425* (2006.01)
*A61K 31/496* (2006.01)

(52) U.S. Cl. .............................. 514/235.5; 514/254.01; 514/365

(58) Field of Classification Search ............... 514/235.5, 514/365, 254.01
See application file for complete search history.

(56) References Cited

U.S. PATENT DOCUMENTS

| 6,011,155 A | 1/2000 | Villhauer |
| 6,107,317 A | 8/2000 | Villhauer |
| 6,110,949 A | 8/2000 | Villhauer |
| 6,432,969 B1 | 8/2002 | Villhauer |

FOREIGN PATENT DOCUMENTS

| WO | WO 98/19998 | 5/1998 |
| WO | WO 00/34241 | 6/2000 |
| WO | WO 01/96295 | 12/2001 |
| WO | WO 02/051836 | 7/2002 |

OTHER PUBLICATIONS

Science (1999), vol. 286, 531-537.*
Cancer and Metastasis Reviews (1998), 17(1), 91-106.*
Huff, Joel R., "HIV Protease: A Novel Chemotherapeutic Target for AIDS," Journal of Medicinal Chemistry, vol. 34, No. 8, Aug. 1991, pp. 2305-2314.*
Supplementary European Search Report for related application EP 01 97 4716, mailed Apr. 6, 2005.
Augustyns, K., et al., The Unique Properties of Dipeptidyl-peptidase IV (DPP IV / CD 26) and the Therapeutic Potential of DPP IV Inhibitors, *Current Medicinal Chemistry*, pp. 311-327 (1999).

\* cited by examiner

*Primary Examiner*—Rebecca L Anderson
(74) *Attorney, Agent, or Firm*—Finnegan, Henderson, Farabow, Garrett & Dunner, LLP

(57) ABSTRACT

The present invention is to provide an aliphatic nitrogen-containing 5-membered ring compound represented by the formula [I]:

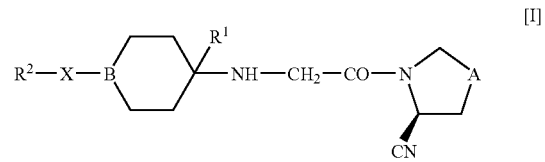

wherein symbols in the formula have the following meanings;
A: —$CH_2$— or —S—,
B: CH or N,
$R^1$: H, a lower alkyl group, etc.,
X: a single bonding arm, —CO—, -Alk-CO—, —$COCH_2$—, -Alk-O—, —O—$CH_2$—, —$SO_2$—, —S—, —COO—, —CON($R^3$)—, -Alk-CON($R^3$)—, —CON($R^3$)$CH_2$—, —$NHCH_2$—, etc.,
$R^3$: hydrogen atom or a lower alkyl group,
Alk: a lower alkylene group, and
$R^2$: (1) a cyclic group which may be substituted,
(2) a substituted amino group, etc.,
provided that when X is —CO—, then B is N,
or a pharmaceutically acceptable salt thereof.

2 Claims, No Drawings

NITROGEN-CONTAINING 5-MEMBERED RING COMPOUND

This is a division of application Ser. No. 11/452,923, filed Jun. 15, 2006, now U.S. Pat. No. 7,332,487, which is a division of application Ser. No. 10/398,485, filed Apr. 4, 2003, now U.S. Pat. No. 7,138,397, which is the National Stage of International Application No. PCT/JP01/08802, filed Oct. 5, 2001, all of which are incorporated herein by reference.

TECHNICAL FIELD

The present invention relates to a novel nitrogen-containing 5-membered ring compound having superior dipeptidylpeptidase IV (DPPIV) inhibitory action that is useful as a pharmaceutical.

BACKGROUND ART

Dipeptidylpeptidase. IV (DPPIV) is a kind of serine protease that specifically hydrolyzes a dipeptide of Xaa-Pro or Xaa-Ala (where Xaa may be any amino acid) from the N terminus of a polypeptide chain.

There are various reports regarding the role of DPPIV (also called to as CD26) in the body and its relationship with diseases (Holst, et al., Diabetes, Vol. 47, pp. 1663-1670, 1998; Augustyns, et al., Current Medicinal Chemistry, Vol. 6, pp. 311-327, 1999; Meester, et al., Immunol. Today, Vol. 20, pp. 367-375, 1999; and, Fleicher, et al., Immunol. Today, Vol. 15, pp. 180-184, 1994).

GLP-1 (glucagon-like peptide 1) is a peptide hormone that mainly acts in the pancreas after being secreted from the lower small intestine after meals, and primarily has the function of amplifying glucose-induced insulin secretion. In addition, there are several reports suggesting that GLP-1 has an appetite-suppressing action. DPPIV hydrolyzes GLP-1, forming an inactive or antagonistic peptide.

Substances that inhibit the enzyme activity of DPPIV enhance the insulin secretion response to oral glucose loading by enhancing the action of intrinsic GLP-1, thereby improving impaired glucose tolerance.

Consequently, DPPIV inhibitors are considered to be useful for the prophylaxis and treatment of diabetes (particularly type 2 diabetes), etc. Also, they are expected to be effective for the prophylaxis and treatment of other diseases induced or exacerbated by impaired glucose tolerance (including hyperglycemia (such as post-prandial hyperglycemia), hyperinsulinemia, diabetes complications (such as renal disorder and neurological disorder), lipid metabolism disorder and obesity, etc.).

Moreover, DPPIV inhibitors are also expected to be effective for the prophylaxis and treatment of diseases that are to be improved by enhancing the appetite-suppressing action of GLP-1 (including overeating and obesity, etc.).

Also, DPPIV (CD26) present on the surface of T cells is strongly upregulated following T cell activation, and plays an important role in the activation and proliferation of T cells. T cell activity is known to be suppressed when DPPIV (CD26) is blocked by antibodies or inhibitory substances. Also, there has been an interest in the correlation between this enzyme and the pathological state in collagen metabolism disorders and diseases associated with abnormal immunity. For example, the DPPIV (CD26) positive rate of peripheral blood T cells is elevated in rheumatoid patients, and high levels of DPPIV activity have been detected in the urine of nephritis patients. Moreover, DPPIV (CD26) is also thought to play an important role in the entry of HIV into lymphocytes.

Consequently, substances that inhibit DPPIV (CD26) are expected to demonstrate prophylactic and therapeutic effects against diseases including autoimmune diseases (such as arthritis and rheumatoid arthritis), osteoporosis, acquired immunodeficiency syndrome (AIDS) and rejections of transplanted organs and tissues.

On the other hand, as compounds having DPPIV inhibitory action, there are described 2-cyanopyrrolidine derivatives having DPPIV inhibitory action in International Patent Laid-Open Publications Nos. WO98/19998 and WO00/34241.

The present invention provides a novel aliphatic nitrogen-containing 5-membered ring compound having an excellent DPPIV inhibitory action.

As a result of earnest research to solve the above problems, the present inventors found a novel nitrogen-containing 5-membered ring compound having DPPIV inhibitory action, thereby accomplished the present invention.

DISCLOSURE OF THE INVENTION

Namely, the present invention relates to an aliphatic nitrogen-containing 5-membered ring compound represented by the formula [I]:

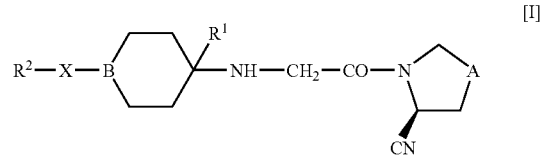

wherein symbols in the formula have the following meanings;

A: —$CH_2$— or —S—,

B: CH or N, $R^1$: H, a lower alkyl group, a hydroxy lower alkyl group or a lower alkoxy lower alkyl group, X: a single bonding arm, —CO—, -Alk-CO—, —$COCH_2$—, -Alk-O—, —O—$CH_2$—, —$SO_2$—, —S—, —COO—, —CON($R^3$)—, -Alk-CON($R^3$)—, —CON($R^3$)$CH_2$—, -Alk-CON($R^3$)$CH_2$—, —$COCH_2$N($R^3$)—, —$SO_2$N($R^3$)— or —$NHCH_2$—, where the bonding arm at a right terminal in each definition of the above X represents a bonding arm with B, $R^3$: hydrogen atom or a lower alkyl group, Alk: a lower alkylene group, and $R^2$: a group selected from the following (1), (2) and (3);

(1) a cyclic group which may be substituted, where the cyclic group portion is
  (i) a monocyclic or bicyclic hydrocarbon group, or
  (ii) a monocyclic or bicyclic heterocyclic group;
(2) an amino group substituted by 1 or 2 substituents which are the same or different and selected from a substituted or unsubstituted lower alkyl group; and
(3) a lower alkyl group, a carboxy lower alkyl group, a lower alkoxy group, a lower alkenyl group, a lower alkoxy-substituted lower alkyl group, a phenoxy group, a phenoxy-substituted lower alkyl group or a phenyl lower alkenyl group, provided that when X is a single bonding arm, then $R^2$ is a group selected from the above (1) and (2), and when X is —CO—, then B is N, or a pharmaceutically acceptable salt thereof.

BEST MODE FOR CARRYING OUT THE INVENTION

Although optical isomers based on an asymmetric carbon can be present in the objective compound [I] of the present invention, the present invention includes any of these optical isomers as well as mixtures thereof. In addition, although isomers (cis form or trans form) are also present based on the relative positions of substituents with respect to the standard plane of a cyclic group, the present invention also includes any of these isomers as well as mixtures thereof.

In the present invention, examples of a lower alkyl group, a lower alkylthio group, a lower alkylsulfonyl group, a lower alkoxy group and a lower alkylamino group include linear or branched groups having 1 to 6 carbon atoms, and particularly those having 1 to 4 carbon atoms. Also, examples of a lower alkanoyl group and a lower alkanoylamino group include linear or branched groups having 2 to 7 carbon atoms, and particularly those having 2 to 5 carbon atoms. Examples of a lower cycloalkyl group and lower cycloalkenyl group include those having 3 to 8 carbon atoms, and particularly 3 to 6 carbon atoms. Examples of a lower alkylene group include linear or branched groups having 1 to 6 carbon atoms, and particularly 1 to 4 carbon atoms. Examples of a lower alkenyl group and lower alkenylene group include those having 2 to 7 carbon atoms, and particularly 2 to 5 carbon atoms. Moreover, examples of a halogen atom include fluorine, chlorine, bromine and iodine.

In the compound [I] of the present invention, specific examples of "hydrogen atom, a lower alkyl group, a hydroxy lower alkyl group or lower alkoxy lower alkyl group" represented by $R^1$ include hydrogen atom, methyl group, hydroxymethyl group, methoxymethyl group, etc. Among them, hydrogen atom or a lower alkyl group (such as methyl group, etc.) is preferred.

In the compound [I] of the present invention, a cyclic group portion of "a cyclic group which may be substituted" represented by $R^2$ includes (i) a monocyclic or bicyclic hydrocarbon group and (ii) a monocyclic or bicyclic heterocyclic group.

Such monocyclic or bicyclic hydrocarbon groups include those having 3 to 15 carbon atoms, which may be partially or completely saturated.

As the monocyclic hydrocarbon group, those having 3 to 7 carbon atoms are preferred, examples of which may include phenyl group, cyclohexyl group, cyclopentyl group, cyclobutyl group, cyclopropyl group, and partially or completely saturated cyclic groups thereof, etc.

As the bicyclic hydrocarbon group, those having 9 to 11 carbon atoms are preferred, examples of which may include an indanyl group, an indenyl group, a naphthyl group, a tetrahydronaphthyl group and partially or completely saturated cyclic groups thereof, etc.

Examples of the monocyclic or bicyclic heterocyclic groups may include a monocyclic or bicyclic heterocyclic group containing 1 to 4 hetero atoms selected from nitrogen atom, oxygen atom and sulfur atom, which may be partially or completely saturated.

Examples of the monocyclic heterocyclic groups may include a heterocyclic group containing 1 to 2 hetero atoms selected from nitrogen atom, oxygen atom and sulfur atom and comprising of a saturated or unsaturated 5- to 7-membered ring, and specifically mentioned are: a pyrrolidinyl group, an imidazolidinyl group, a pyrazolidinyl group, an oxolanyl group, a thiolanyl group, a pyrrolinyl group, an imidazolinyl group, a pyrazolinyl group, a pyrrolyl group, an imidazolyl group, a pyrazolyl group, a triazolyl group, a tetrazolyl group, a furyl group, an oxazolyl group, an isoxazolyl group, an oxadiazolyl group, a thienyl group, a thiazolyl group, an isothiazolyl group, a thiadiazolyl group, a piperidyl group, a piperazinyl group, a morpholinyl group, a thiomorpholinyl group, a pyridyl group, a pyrimidinyl group, a pyrazinyl group, a pyridazinyl group, a pyranyl group, a tetrahydropyridyl group, a dihydro-pyridazinyl group, a perhydroazepinyl group, a perhydrothiazepinyl, and partially or completely saturated cyclic groups thereof, etc.

Examples of the bicyclic heterocyclic group may include a heterocyclic group containing 1 to 3 hetero atoms selected from nitrogen atom, oxygen atom and sulfur atom and comprising two saturated or unsaturated 5- to 7-membered rings being fused, and specifically mentioned are: an indolinyl group, an isoindolinyl group, an indolyl group, an indazolyl group, an isoindolyl group, a benzimidazolyl group, a benzothiazolyl group, a benzoxazolyl group, a benzodioxolyl group, a benzothienyl group, a benzofuryl group, a thienopyridyl group, a thiazolopyridyl group, a pyrrolopyridyl group, a dihydropyrrolopyridyl group, a quinolyl group, an isoquinolyl group, a quinoxalinyl group, a quinazolinyl group, a phthalazinyl group, a cinnolinyl group, a chromanyl group, an isochromanyl group, a naphthyridinyl group, and partially or completely saturated cyclic groups thereof, etc.

Among these cyclic groups (monocyclic or bicyclic hydrocarbon groups or monocyclic or bicyclic heterocyclic groups), "(i) a monocyclic hydrocarbon group having 3 to 7 carbon atoms, (ii) a monocyclic heterocyclic group (preferably, a monocyclic 5- to 6-membered aliphatic heterocyclic group) containing 1 to 2 hetero atoms selected from nitrogen atom, oxygen atom and sulfur atom, or (iii) a bicyclic heterocyclic group containing 1 to 3 hetero atoms selected from nitrogen atom, oxygen atom and sulfur atom and comprising two 5- to 7-membered rings being fused"

is preferred, and examples of which may include:

"phenyl group, cyclohexyl group, cyclopentyl group, cyclobutyl group, cyclopropyl group, a pyrrolidinyl group, an imidazolidinyl group, a pyrazolidinyl group, an oxolanyl group, a thiolanyl group, a pyrrolinyl group, an imidazolinyl group, a pyrazolinyl group, a pyrrolyl group, an imidazolyl group, a pyrazolyl group, a triazolyl group, a tetrazolyl group, a furyl group, an oxazolyl group, an isoxazolyl group, an oxadiazolyl group, a thienyl group, a thiazolyl group, an isothiazolyl group, a thiadiazolyl group, a piperidyl group, a piperazinyl group, a morpholinyl group, a thiomorpholinyl group, a pyridyl group, a pyrimidinyl group, a pyrazinyl group, a pyridazinyl group, a pyranyl group, a tetrahydropyridyl group, a dihydro-pyridazinyl group, a perhydroazepinyl group, a perhydrothiazepinyl group, an indolinyl group, an isoindolinyl group, an indolyl group, an indazolyl group, an isoindolyl group, a benzimidazolyl group, a benzothiazolyl group, a benzoxazolyl group, a benzodioxolyl group, a benzothienyl group, a benzofuryl group, a thienopyridyl group, a thiazolopyridyl group, a pyrrolopyridyl group, a dihydropyrrolopyridyl group, a quinolyl group, an isoquinolyl group, a quinoxalinyl group, a quinazolinyl group, a phthalazinyl group, a cinnolinyl group, a chromanyl group, an isochromanyl group, a naphthyridinyl group, and partially or completely saturated cyclic groups thereof, etc.".

Among them, "(i) a monocyclic heterocyclic group (preferably, a monocyclic 5- to 6-membered aliphatic heterocyclic group) containing 1 to 2 hetero atoms selected from nitrogen atom, oxygen atom and sulfur atom, or (ii) a bicyclic heterocyclic group containing 1 to 3 hetero atoms selected from nitrogen atom, oxygen atom and sulfur atom and comprising two 5- to 7-membered rings being fused" is more preferred.

Also, among them, more preferred examples may include:

"phenyl group, cyclohexyl group, cyclopropyl group, a pyrrolidinyl group, an imidazolidinyl group, a pyrazolidinyl group, a pyrrolyl group, an imidazolyl group, a pyrazolyl group, a furyl group, an oxazolyl group, an isoxazolyl group, a thienyl group, a thiazolyl group, an isothiazolyl group, a piperidyl group, a piperazinyl group, a morpholinyl group, a thiomorpholinyl group, a pyridyl group, a pyrimidinyl group, a pyrazinyl group, a pyridazinyl group, an isoindolinyl group, an indolinyl group, a thiazolopyridyl group, a pyrrolopyridyl group, a dihydropyrrolopyridyl group, a benzoxazolyl group, quinolyl group, an isoquinolyl group, a quinazolinyl group, an isoindolyl group, an indolyl group, and partially or completely saturated cyclic groups thereof, etc."

Also, more preferred examples may include:

"a piperidyl group (1-piperidyl group, etc.), a piperazinyl group (1-piperazinyl group, etc.), a morpholinyl group (4-morpholinyl group, etc.), an indolinyl group (1-indolinyl group, etc.), an isoindolinyl group (2-isoindolinyl group, etc.), a thiazolopyridyl group (thiazolo[5,4-b]pyridin-2-yl group, etc.), etc."

Also, among them, particularly preferred examples may include:

"1-piperidyl group, 1-piperazinyl group, 4-morpholinyl group, 1-indolinyl group, 2-isoindolinyl group, thiazolo-[5,4-b]pyridin-2-yl group, etc.".

"A cyclic group (a monocyclic or bicyclic hydrocarbon group or a monocyclic or bicyclic heterocyclic group) which may be substituted" represented by $R^2$ may be unsubstituted or may have 1 to 3 substituents which are the same or different.

The substituent(s) of the cyclic group is/are not particularly limited, and examples of which may include substituents selected from the following "substituents of Group A". Among them, "substituents of Group A'" are more preferred.

In the objective compound [I] of the present invention, substituents of "the amino group substituted by 1 or 2 substituents which are the same or different, selected from a substituted or unsubstituted lower alkyl group" represented by $R^2$ are not particularly-limited, and examples of which may include a lower alkyl group substituted by a group selected from "cyano group, a lower alkoxy group (methoxy group, etc.), a monocyclic-aryl group (phenyl group, etc.), a nitrogen-containing monocyclic 6-membered aromatic heterocyclic group (a pyridyl group, etc.), etc."

Substituents of Group A:

As substituents of Group A, the following substituents are exemplified:

a halogen atom (Cl, F, Br, etc.), cyano group, nitro group, amino group, oxo group, a lower alkyl group, a lower alkoxy group, a lower alkanoyl group, a lower alkoxycarbonyl group, a lower alkoxycarbonylamino group, a lower cycloalkanoyl, group, a halo-lower alkyl group, halo-lower alkylcarbonyl group, a nitrogen-containing monocyclic 5- to 6-membered aliphatic heterocyclic group-substituted carbonyl group, a nitrogen-containing monocyclic 6-membered aromatic heterocyclic group, a monocyclic aryl group, a monocyclic aryl group-substituted aryl lower alkylcarbonylamino group, a lower alkylthio group, an aminosulfonyl group, etc.

(As "a nitrogen-containing monocyclic 5- to 6-membered aliphatic heterocyclic group" in "the nitrogen-containing monocyclic 5- to 6-membered aliphatic heterocyclic group-substituted carbonyl group", specific examples include "a pyrrolidinyl group, a piperidinyl group, a piperazinyl group, etc."

Also, as "the nitrogen-containing monocyclic 6-membered aromatic heterocyclic group", specific examples may include "a pyridyl group, a pyrimidinyl group, a pyrazinyl group, a pyridazinyl group, a pyranyl group, etc."

As "the monocyclic aryl group" portion in "the monocyclic aryl group" and "the monocyclic aryl group-substituted aryl lower alkylcarbonylamino group", specific examples may include phenyl group, etc.)

Substituents of Group A' (Particularly Preferred Substituents of Group A):

As more preferred substituents of Group A, the following substitutes are exemplified:

oxo group, a lower alkanoyl group, a lower cycloalkanoyl group, a lower alkoxycarbonyl group and a nitrogen-containing monocyclic 5- to 6-membered aliphatic heterocyclic group-substituted carbonyl group (a pyrrolidinyl group, a piperidinyl group, etc.).

Among the objective compounds [I] of the present invention wherein B is CH, in case that X is a single bonding arm, preferred examples for $R^2$ may include (1) a monocyclic or bicyclic nitrogen-containing heterocyclic group which may be substituted or (2) an amino group substituted by 1 or 2 substituents selected from a substituted or unsubstituted lower alkyl group, represented by the formula:

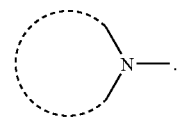

In the objective compound [I] of the present invention wherein B is CH, among the two kinds of cis-trans isomers based on a cyclohexyl ring in the structure [I] as a standard plane, a trans-isomeric compound is more preferred from the view point of obtaining a higher DPPIV inhibitory activity. That is, among the objective compound [I] of the present invention wherein B is CH, a compound having the following partial structure:

or a pharmaceutically acceptable salt thereof is preferred.

As one compound group of the compounds of the present invention, among the compounds of [I], those wherein X is a single bonding arm, -Alk-CO—, —COCH$_2$—, -Alk-O—, —O—CH$_2$—, —SO$_2$—, —S—, —COO—, —CON(R$^3$)—, -Alk-CON(R$^3$)—, —CON(R$^3$)CH$_2$—, -Alk-CON(R$^3$)CH$_2$—, —COCH$_2$N(R$^3$)—, —SO$_2$N(R$^3$)— or —NHCH$_2$—, and $R^2$ is (1) a cyclic group which may be substituted, where the cyclic group portion is (i) a monocyclic or bicyclic hydrocarbon group, or (ii) a monocyclic or bicyclic heterocyclic group; or (2) an amino group substituted by 1 or 2 substituents which are the same or different and selected from a substituted or unsubstituted lower alkyl group, can be exemplified.

(Compound Group 1, Compound I-e)

Also, as other compounds group, among the compounds [I] or the above-mentioned Compound Group 1, compounds group in which $R^2$ is a group selected from (1) a cyclic group which may have 1 to 3 substituents which are the same or different and selected from the substituents of Group A, where the cyclic group portion is (i) a monocyclic or bicyclic hydrocarbon group, or (ii) a monocyclic or bicyclic heterocyclic group;

(2) an amino group substituted by 1 to 2 substituents which are the same or different and selected from "a lower alkyl group which may be substituted by a substituent selected from cyano group, a lower alkoxy group, phenyl group and a nitrogen-containing monocyclic 6-membered aromatic heterocyclic group"; and (3) a lower alkyl group, a carboxy lower alkyl group, a lower alkoxy group, a lower alkenyl group, a lower alkoxy-substituted lower alkyl group, phenoxy group, a phenoxy-substituted lower alkyl group or a phenyl lower alkenyl group;

may be exemplified (Compound Group 2).

Also, as another compounds group, among the compounds [I] or the above-mentioned Compound Group 1 or 2, compounds group in which $R^2$ is a cyclic group which may be substituted, where the cyclic group portion is a group selected from (i) a monocyclic hydrocarbon group having 3 to 7 carbon atoms, (ii) a monocyclic heterocyclic group containing 1 to 2 hetero atoms selected from nitrogen atom, oxygen atom and sulfur atom, and (iii) a bicyclic heterocyclic group containing 1 to 3 hetero atoms selected from nitrogen atom, oxygen atom and sulfur atom and comprising two 5- to 7-membered rings being fused may be exemplified (Compound Group 3).

Also, as another more preferred compound group, among the compounds [I] or the above-mentioned Compound Group 1, 2 or 3, compounds in which $R^2$ is a cyclic group which may have 1 to 3 substituents which are the same or different, selected from the substituents of Group A', where the cyclic portion is a group selected from a piperidyl group, a piperazinyl group, a morpholinyl group, an indolinyl group, an isoindolinyl group, and a thiazolopyridyl group may be exemplified (Compound Group 4).

Also, as another preferred compound group, among the compounds [I] or the above-mentioned Compound Group 1, 2, 3 or 4, compounds wherein B is CH, X is a single bonding arm and $R^2$ is (1) a monocyclic or bicyclic nitrogen-containing heterocyclic group which may be substituted or (2) an amino group substituted by 1 or 2 substituents selected from a substituted or unsubstituted lower alkyl group, represented by the formula:

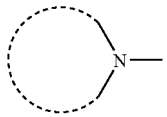

may be exemplified (Compound Group 5).

Also, as another preferred compound group, among the compounds [I] or the above-mentioned Compound Group 1, 2, 3, 4 or 5;

compounds group wherein B is CH, X is a single bonding arm, and A is —$CH_2$—;

compounds group wherein B is CH, X is a single bonding arm, A is —$CH_2$—, and $R^1$ is hydrogen atom or a lower alkyl group;

compounds group wherein B is CH, X is a single bonding arm, and A is —S—;

compounds group wherein B is CH, X is a single bonding arm, A is —S—, and $R^1$ is hydrogen atom or a lower alkyl group;

and the like may be exemplified.

Furthermore, in each of the above-mentioned compound groups, as a more preferred compound group, a group of compounds wherein B is CH, and the compound has the following partial structure:

may be exemplified.

Also, as specific examples of preferred compounds, the following compounds may be exemplified.

(S)-2-cyano-1-[t-4-(4-acetyl-1-piperazinyl)-1-methyl-r-1-cyclohexylamino]acetylpyrrolidine;

(S)-2-cyano-1-[trans-4-(1,3-dioxo-2-isoindolinyl)-cyclohexylamino]acetylpyrrolidine;

(S)-2-cyano-1-(trans-4-morpholinocyclohexylamino]-acetylpyrrolidine; and (S)-2-cyano-1-[trans-4-(thiazolo[5,4-b]pyridin-2-yl)-cyclohexylamino]acetylpyrrolidine, etc.

The objective compound. [I] or a pharmaceutically acceptable salt thereof of the present invention has superior inhibitory action on the enzyme activity of DPPIV. They have superior inhibitory action especially on human DPPIV. In addition, they also exhibit high selectivity with respect to DPPIV (namely, type IV dipeptidylpeptidase) in various serine proteases (e.g., plasmin, thrombin, prolylendopeptidase, trypsin and dipeptidylpeptidase II).

Also, the objective compound [I] or a pharmaceutically acceptable salt thereof of the present invention improves insulin secretion response to oral glucose loading by means of its DPPIV inhibitory action.

Thus, the objective compound [I] or a pharmaceutically acceptable salt thereof of the present invention is useful as prophylactic or therapeutic agents for diseases relating to DPPIV (diseases mediated by DPPIV), that is, diseases which is expected to be alleviated by inhibiting DPPIV enzyme activity.

Examples of such diseases include diabetes (e.g., type 1 diabetes and type 2 diabetes), hyperglycemia (such as postprandial hyperglycemia), hyperinsulinemia, diabetes complications (such as renal disorder and neurological disorder), obesity, overeating, lipid metabolism disorder (such as hyperlipemia including hypertriglyceridemia and others), autoimmune diseases (such as arthritis and rheumatoid arthritis), osteoporosis, acquired immunodeficiency syndrome (AIDS) and rejection of transplanted organs and tissues.

The objective compound [I] or a pharmaceutically acceptable salt thereof of the present invention is particularly useful as a prophylactic or therapeutic agent of diabetes (and particularly type 2 diabetes).

Further, the compound of the present invention has low toxicity, and thus, has a high level of safety when used as a pharmaceutical compound. Furthermore, it also demonstrates superior pharmacokinetic characteristics [including bioavailability, in vitro metabolic stability (stability in human liver homogenates), P450 inhibitory action and protein binding capabilities, etc.].

The DPPIV inhibitory action of the compound of the present invention as well as its pharmaceutical efficacy (including anti-hyperglycemia effect and the effect of improving insulin secretion response to glucose loading) based on that action can be confirmed by known methods or methods equivalent to those methods (WO 98/19998; WO 00/34241; Holst, et al., Diabetes, Vol. 47, pp. 1663-1670, 1998; Augustyns, et al., Current Medicinal Chemistry, Vol. 6, pp. 311-327, 1999; Meester, et al., Immunol. Today, Vol. 20, pp. 367-375, 1999; and, Fleicher, et al., Immunol. Today, Vol. 15, pp. 180-184, 1994).

The objective compound [I] of the present invention can be used for a pharmaceutical use either in a free form or in a form of a pharmaceutically acceptable salt. Examples of the pharmaceutically acceptable salt of the compound [I] include an inorganic acid salt such as hydrochloride, sulfate, phosphate or hydrobromide, and an organic acid salt such as acetate, fumarate, oxalate, citrate, methanesulfonate, benzenesulfonate, tosylate or maleate, etc. In addition, in case that a compound has a substituent(s) such as carboxyl group, a salt with a base (for example, an alkali metal salt such as a sodium salt, a potassium salt, etc., or an alkaline earth metal salt such as a calcium salt and the like) may be mentioned.

The objective compound [I] or the pharmaceutically acceptable salt thereof of the present invention include its internal salts, adducts, solvates and hydrates.

The objective compound [I] or pharmaceutically acceptable salts thereof of the present invention can be administered orally or parenterally and used as commonly used pharmaceutical preparations, such as tablets, granules, capsules, powders, injection solution and inhalants. The compound of the present invention, for example, can be used with pharmaceutically acceptable general excipients such as binder, disintegrator, extenders, fillers and lubricants, or diluents, and prepared according to the usual method.

The administration dose of the objective compound [I] or pharmaceutically acceptable salts thereof of the present invention may vary depending on the administration method, age, weight and condition of a patient, and it is generally about 0.01 to 300 mg/kg, preferably about 0.1 to 30 mg/kg per day.

The objective compound [I] of the present invention can be prepared according to the following (Process A) to (Process D), but it is not limited to these processes.

(Process A)

The objective compound [I] of the present invention can be prepared by reacting a compound represented by the formula [II]:

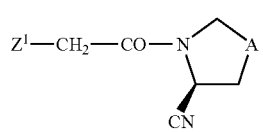

wherein $Z^1$ represents a reactive residue and A has the same meaning as defined above, with a compound represented by the formula [III]:

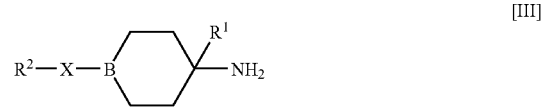

wherein $R^1$, $R^2$, B and X have the same meanings as defined above, or salts thereof, and optionally, by making the products into a pharmaceutically acceptable salt.

As examples of the salt of the compound [III], a salt with an inorganic acid such as hydrochloride and sulfate, or a salt with an inorganic base such as an alkali metal salt and an alkaline earth metal salt can be used.

As the reactive residue of $Z^1$, commonly used reactive residues such as a halogen atom, a lower alkylsulfonyloxy group and an arylsulfonyloxy group can be used, among which the halogen atom is particularly preferred.

The reaction of the compound [II] with the compound [III] or the salt thereof can be carried out in a suitable solvent or without solvent in the presence or absence of an acid acceptor.

As the solvent, any solvents may be suitable as long as it does not adversely affect to the reaction, and, for example, acetonitrile, methanol, ethanol, isopropyl alcohol, propyl alcohol, acetone, dimethylformamide, dimethyl sulfoxide, tetrahydrofuran, ether, dioxane, ethyl acetate, toluene, methylene chloride, dichloro-ethane, chloroform or a mixed solvent of these solvents can be suitably used.

This reaction suitably proceeds at 0 to 120° C., particularly at room temperature to 80° C.

As the acid acceptor, an inorganic base (for example, alkali metal hydride such as sodium hydride, alkali metal carbonate such as sodium carbonate and potassium carbonate, alkali metal alkoxide such as sodium methoxide, alkali metal such as sodium, and alkali metal hydroxide such as sodium hydroxide and potassium hydroxide, etc.) or an organic base (for example, triethylamine, diisopropylethylamine, N-methylmorpholine, pyridine, dimethylaniline, dimethylaminopyridine, etc.) can be suitably used.

(Process B)

In addition, among the objective compound [I] of the present invention, the compound wherein $R^2$ represents a monocyclic or bicyclic nitrogen-containing heterocyclic group which may be substituted, and X represents —COO—, represented by the formula [I-a]:

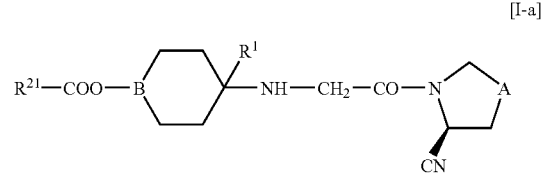

wherein $R^{21}$ represents a monocyclic or bicyclic nitrogen-containing heterocyclic group which may be substituted, and $R^1$, A and B have the same meanings as defined above, can be prepared by reacting a compound represented by the formula [IV]:

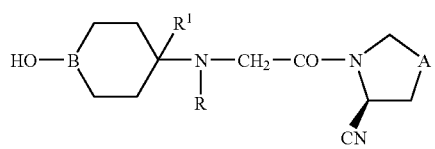

wherein R represents a protective group for the amino group, and R¹, A and B have the same meanings as defined above, or a salt thereof with a phosgene or an equivalent thereof, and subsequently, further reacting with a compound represented by the formula [V]:

R²¹H    [V]

wherein R²¹ has the same meaning as defined above, to obtain a compound represented by the formula [VI]:

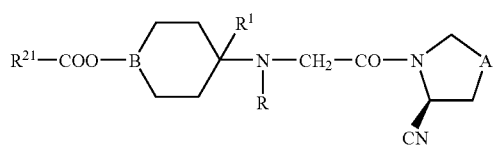

wherein R, R¹, R²¹, A and B have the same meanings as defined above, or a salt thereof, and further removing the protective group (R) for the amino group from the product.

Followed by reacting the compound [IV] with a phosgene or an equivalent thereof, the reaction with the compound [V] can be carried out in a suitable solvent or without solvent in the presence of a phosgene or an equivalent thereof and an acid acceptor.

As "the phosgene or the equivalent thereof", triphosgene, diphosgene, carbonyldiimidazol, 4-nitrophenyl-chloroformate, etc. can be suitably used.

As the acid acceptor, an inorganic base (for example, alkali metal hydride such as sodium hydride, alkali metal carbonate such as sodium carbonate and potassium carbonate, alkali metal amide such as sodium amide and lithium amide, alkali metal alkoxide such as sodium methoxide, alkali metal such as sodium, and alkali metal hydroxide such as sodium hydroxide and potassium hydroxide, etc.) or an organic base (for example, triethylamine, diisopropylethylamine, N-methylmorpholine, pyridine, dimethylaniline, dimethylaminopyridine, etc.) can be suitably used.

As the solvent, any solvents may be suitable as long as it does not adversely affect to the reaction, and, for example, methylene chloride, dichloroethane, chloroform, ether, tetrahydrofuran, ethyl acetate, toluene or a mixed solvent thereof can be suitably used. The present reaction suitably proceeds at −78° C. to 110° C., especially at 0° C. to room temperature.

The following removal of the protective group (R) for an amino group of the compound [VI] can be carried out according to the conventional method, and it can be carried out, for example, in a suitable solvent or without solvent by an acid treatment, base treatment or catalytic reduction.

As the acid, an inorganic acid such as hydrochloric acid, sulfuric acid, etc., and an organic acid such as acetic acid, trifluoroacetic acid, methanesulfonic acid, p-toluenesulfonic acid, etc. can be suitably used.

As the base, an inorganic base (for example, alkali metal hydride such as sodium hydride, etc., alkali metal carbonate such as sodium carbonate, potassium carbonate, etc., alkali metal amide such as sodium amide, lithium amide, etc., alkali-metal alkoxide such as sodium methoxide, etc., alkali metal such as sodium, etc., and alkali metal hydroxide such as sodium hydroxide, potassium hydroxide, etc.) or an organic base (for example, triethylamine, diisopropylethylamine, morpholine, N-methylmorpholine, pyridine, piperidine, dimethylaniline, dimethylaminopyridine, etc.) can be suitably used.

The catalytic reduction can be carried out by suitably using palladium-carbon, palladium hydroxide-carbon, platinum oxide or Raney nickel under hydrogen atmosphere.

As the solvent, any solvents may be suitable as long as it does not adversely affect to the reaction, and, for example, methanol, ethanol, isopropyl alcohol, propyl alcohol, dioxane, methylene chloride, chloroform, dichloro-ethane, ether, tetrahydrofuran, ethyl acetate, toluene or a mixed solvent thereof can be suitably used.

This reaction suitably proceeds at −78° C. to 80° C., particularly at 0° C. to room temperature.

(Process C)

In the objective compound [I] of the present invention, the compound wherein B is N, X is —CO—, -Alk-CO— or —SO₂—, represented by the formula [I-b]:

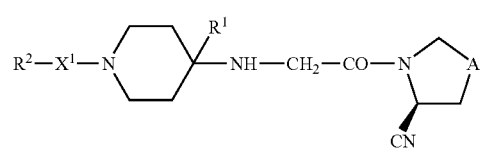

wherein X¹ represents —CO—, -Alk-CO— or —SO₂—, and R¹, R² and A have the same meanings as defined above, can be prepared by reacting a compound represented by the formula [VII]:

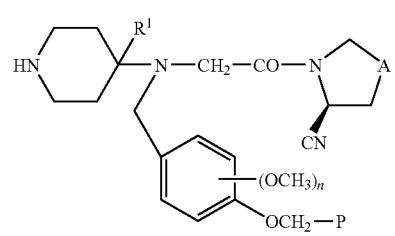

wherein n is 0, 1, 2 or 3, P represents a resin residue, and R¹ and A have the same meanings as defined above, with a compound represented by the formula [VIII]:

R²—V¹    [VIII]

wherein V¹ represents —COOH, -Alk-COOH or a chlorosulfonyl group, and R² has the same meaning as defined above, or a salt thereof, and subsequently removing a linker and the resin residue portion represented by the formula [IX]:

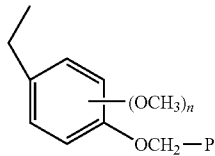

wherein P and n have the same meanings as defined above, from the reaction product.

Or else, in the compound [I-b], a compound wherein $X^1$ is —CO— and $R^2$ is a carboxy lower alkylene group can be prepared by using a compound represented by the formula [X]:

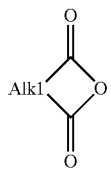

wherein Alk1 represents a lower alkylene group, in place of the compound [VIII] or a salt thereof to carry out the reaction with the compound [VII], and subsequently removing the linker and the resin residue portion represented by the formula [IX] from the reaction product.

(Process D)

Also, in the compound [I], a compound wherein B is CH and X is —CON($R^3$)—, -Alk-CON($R^3$)—, or —SO$_2$N($R^3$)—, represented by the formula [I-c]:

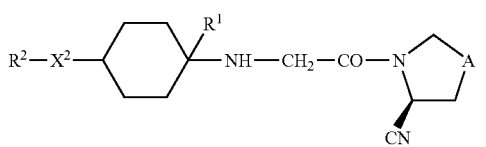

wherein $X^2$ represents —CON($R^3$)—, -Alk-CON($R^3$)— or —SO$_2$N($R^3$)—, and $R^1$, $R^2$, $R^3$ and A have the same meanings as defined above, can be prepared by reacting a compound represented by the formula [XI]:

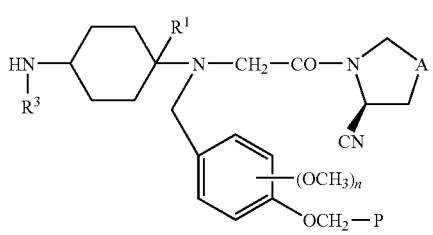

wherein $R^1$, $R^3$, A, P and n have the same meanings as defined above, with a compound represented by the formula [XII]:

$$R^2—V^2 \quad [XII]$$

wherein $V^2$ represents —COOH, -Alk-COOH or chlorosulfonyl group and $R^2$ has the same meaning as defined above, or a salt thereof, and subsequently removing the linker and the resin residue portion represented by the formula [IX] from the reaction product.

Alternatively, in the compound [I-c], a compound wherein $X^2$ is —CON($R^3$)— and $R^2$ is a carboxy lower alkyl group can be prepared by using a compound [X] in place of the compound [XII] or a salt thereof, reacting the same with the compound [XI], and subsequently removing the linker and the resin residue portion represented by the formula [IX] from the reaction product.

Also, in the compound [I], a compound wherein B is CH and X is —CON($R^3$)CH$_2$— or -Alk-CON($R^3$)CH$_2$—, represented by the formula [I-d]:

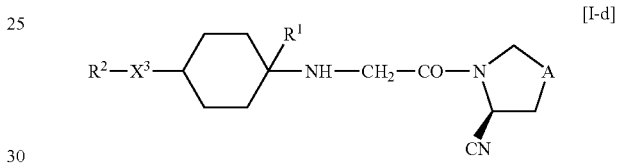

wherein $X^3$ represents —CON($R^3$)CH$_2$— or -Alk-CON($R^3$)CH$_2$—, and $R^1$, $R^2$, $R^3$ and A have the same meanings as defined above, can be prepared by reacting a compound represented by the formula [XIII]:

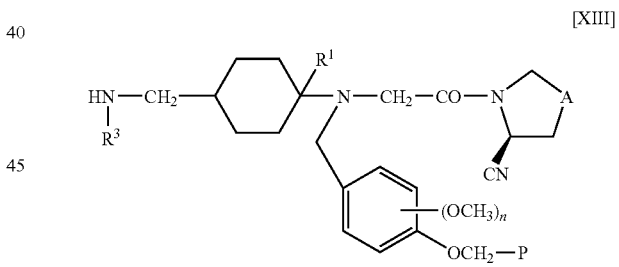

wherein $R^1$, $R^3$, A, P and n have the same meanings as defined above, with a compound represented by the formula [XII] or a salt thereof, and subsequently removing the linker and the resin residue portion represented by the formula [IX] from the reaction product.

Alternatively, a compound [I-d] wherein $X^2$ is —CON($R^3$)CH$_2$— and $R^2$ is a carboxy lower alkyl group can be prepared by using a compound [X] in place of the compound [XII], or a salt thereof, reacting the same with the compound [XIII], and subsequently removing the linker and the resin residue portion represented by the formula [IX] from the reaction product.

(Reactions in Process C and Process D)

The reactions in Process C (the reaction between the compound [VII] and the compound [VIII] or a salt thereof (or the compound [X])); and the reactions in Process D (the reaction between the compound [XI] or [XIII] and the compound [XII] or a salt thereof (or the compound [X]) can be carried out, optionally in the presence of a condensing agent and/or an acid acceptor, in a suitable solvent or without solvent. Further, the linker and the resin residue portion are removed according to the conventional method, and if necessary, purification is carried out by, for example, extraction, distribution, reprecipitation, crystallization, recrystallization, various kinds of chromatographies, high performance chromatography, etc.

As the linker, a group in which a resin residue (P) portion is removed from the group represented by the formula [IX] can be exemplified.

As the resin residue represented by P, a resin that is used in a conventional solid phase synthesis can be used, and there may be mentioned, for example, a Merrifield resin (4-chloromethyl polystyrene resin, etc.), a Wang resin (4-benzyloxybenzyl alcohol resin, etc.), a hydroxymethyl polystyrene resin (4-hydroxymethyl polystyrene resin, etc.), etc. As the kinds of resin, any resin may be used as long as it does not adversely affect to the reaction, and it is suitably selected depending on the kind of the objective compound. Generally, those with a particle diameter of 70 to 200 μm are preferably used, and a loading capacity is preferably 0.1 to 2 mmol/g.

As the condensing agent, O-benzotriazol-1-yl-N,N,N',N'-tetramethyluroniumhexafluorophosphate, DCC (dicyclohexylcarbodiimide), EDC (1-ethyl-3-(3-dimethyl-aminopropyl)carbodiimide), chloroformates (for example, ethyl chloroformate and isobutyl chloroformate) and carbonyldiimidazole, etc. can be suitably used. Also, for promoting the reaction, an additive such as a base (sodium carbonate, sodium hydrogencarbonate, triethylamine, pyridine, 4-dimethylaminopyridine, diisopropylethylamine, 1,8-diazabicyclo[5.4.0]undec-7-ene, etc.), 1-hydroxybenzotriazole, 1-hydroxysuccinimide, etc. can be added to the above condensing agent.

As the acid acceptor, alkali metal hydroxide such as sodium hydroxide and potassium hydroxide, alkali metal hydrogencarbonate such as sodium hydrogencarbonate and potassium hydrogencarbonate, alkali metal carbonate such as sodium carbonate and potassium carbonate, an organic base (triethylamine, pyridine, etc.), etc. can be suitably used.

The following removal of the linker and the resin residue portion can be suitably carried out in a suitable solvent or without solvent by treating the product with trifluoroacetic acid, trifluoromethanesulfonic acid, hydrogen fluoride, hydrogen bromide, hydrogen chloride, etc, and a mixture thereof.

As the solvent, any solvents may be suitable as long as it does not adversely affect to the reaction, and, for example, methylene chloride, N-methyl morpholine, dimethylformamide, tetrahydrofuran, dimethylacetamide or a mixed solvent thereof can be suitably used.

The reaction in Process C suitably proceeds at 0 to 120° C., particularly at 20 to 50° C. And the reaction in Process D suitably proceeds at 0 to 50° C., particularly at 0 to 30° C.

As the solvent to be used in the following reaction for removing the linker and the resin residue portion, any solvents may be suitable as long as it does not adversely affect to the reaction, and, for example, methylene chloride, acetic acid, trifluoroacetic acid or a mixed solvent thereof can be suitably used. The reaction suitably proceeds at 0 to 50° C., particularly at 0 to 30° C.

(Starting Material for Process A)

The starting material [II] of the present invention can be prepared, for example, according to the process described in International Patent Publications Nos. WO98/19998, WO00/34241 and Reference Examples mentioned below (Reference Example 1 or 2), etc.

For example, the compound [II] can be obtained by reacting a compound represented by the formula [20]:

[20]

wherein A has the same meaning as defined above, with a compound represented by the formula [21]:

$Z^2—CH_2CO—Z^3$ [21]

wherein $Z^2$ and $Z^3$ represent a reactive residue which may be the same or different, in the presence of an acid acceptor (for example, triethylamine, etc.) to obtain a compound represented by the formula [22]:

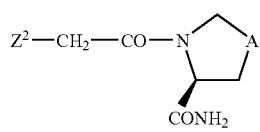

[22]

wherein $Z^2$ and A have the same meanings as defined above, and treating the product with a dehydrating agent (for example, phosphorous oxychloride, trifluoroacetic anhydride, etc.) according to the conventional method.

As the reactive residue of $Z^2$ or $Z^3$, the same reactive residue commonly used as mentioned above $Z^1$ can be suitably used.

The starting material [III] can be prepared, for example, by the same process as described in Reference Examples mentioned below (Reference Examples 7 to 10).

For example, the compound [III] wherein X is $—O—CH_2—$ or $—NHCH_2—$ can be prepared by reacting a compound represented by the formula [23]:

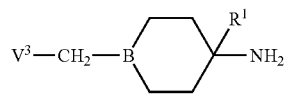

[23]

wherein $V^3$ represents a hydroxy group or an amino group, and $R^1$ and B have the same meanings as defined above, an amino group-protected material thereof or a salt thereof with a compound represented by the formula [24]:

$R^2—Z^4$ [24]

wherein $Z^4$ represents a reactive residue and the other symbol has the same meaning as defined above, in the presence or absence of an acid acceptor (for example, an organic base such as triethylamine, diisopropylethylamine, etc., and an inorganic base such as sodium hydride, potassium carbonate, etc.), and, if necessary, removing the protective group for the amino group according to the conventional method.

As the protective group for the amino group, any of the same protective groups commonly used as mentioned above R can be suitably used.

As the reactive residue of $Z^4$, the same reactive residue commonly used as mentioned above $Z^1$ can be suitably used.

Also, the compound [III] wherein X is -Alk-O— or —S— can be prepared by reacting a compound represented by the formula [25]:

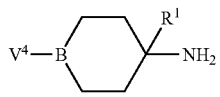

[25]

wherein $V^4$ represents a hydroxy group or a mercapto group and $R^1$ and B have the same meanings as defined above, an amino group-protected material thereof or a salt thereof with a compound represented by the formula [26a] or the formula [26b]:

$R^2—Z^{51}$ [26a] or $R^2$-Alk-$Z^{52}$ [26b]

wherein $Z^{51}$ and $Z^{52}$ represent a reactive residue and $R^2$ and Alk have the same meanings as defined above, in the presence or absence of an acid acceptor (for example, an organic base such as triethylamine, diisopropylethylamine, etc., and an inorganic base such as sodium hydride, potassium carbonate, etc.), and, if necessary, removing the protective group for the amino group according to the conventional method. As the protective group for the amino group, any of the same protective groups commonly used as mentioned above R can be suitably used.

As the reactive residue of $Z^{51}$ and $Z^{52}$, the same reactive residue commonly used as mentioned above $Z^1$ can be suitably used.

Also, the compound [III] wherein X is —COCH$_2$N(R$^3$)— or —SO$_2$N(R$^3$)— can be obtained by reacting a compound represented by the formula [27]:

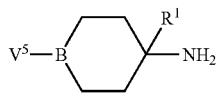

[27]

wherein $V^5$ represents —N(R$^3$)H, and $R^1$, $R^3$ and B have the same meanings as defined above, an amino group-protected material thereof or a salt thereof with a compound represented by the formula [28a] or the formula [28b]:

$R^2$—COCH$_2$—$Z^{61}$ [28a] or $R^2$—SO$_2$—$Z^{62}$ [28b]

wherein $Z^{61}$ and $Z^{62}$ represent a reactive residue and $R^2$ has the same meaning as defined above, in the presence or absence of an acid acceptor (for example, an organic base such as triethylamine, diisopropylethylamine, etc., and an inorganic base such as sodium hydride, potassium carbonate, etc.), and, if necessary, removing the protective group for the amino group according to the conventional method. As the protective group for the amino group, any of the same protective groups commonly used as mentioned above R can be suitably used.

As the reactive residue of $Z^{61}$; and $Z^{62}$, the same reactive residue commonly used as mentioned above $Z^1$ can be suitably used.

Also, the compound [III] wherein X is —CON(R$^3$)—, -Alk-CON(R$^3$)— or —SO$_2$N(R$^3$)— can be prepared by reacting the compound represented by the formula [27], an amino group-protected material thereof or a salt thereof, with a compound represented by the formula [29]:

$R^2$—$V^6$ [29]

wherein $V^6$ represents —COOH, -Alk-COOH or —SO$_3$H and $R^2$ has the same meaning as defined above, or a salt thereof in the presence of a condensing agent (1-ethyl-3-(3-dimethylaminopropyl)carbodiimide, etc.), and, if necessary, removing the protective group for the amino group according to the conventional method. As the protective group for the amino group, any of the same protective groups commonly used as mentioned above R can be suitably used.

Also, the compound [III] wherein X is —CON(R$^3$)CH$_2$— or -Alk-CON(R$^3$)CH$_2$— can be prepared by reacting a compound represented by the formula [30]:

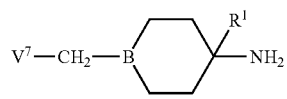

[30]

wherein $V^7$ represents —N(R$^3$)H, and $R^1$, $R^3$ and B have the same meanings as defined above, an amino group-protected material thereof or a salt thereof, with a compound represented by the formula [31]:

$R^2$—$V^8$ [–]

wherein $V^8$ represents —COOH or -Alk-COOH and $R^2$ has the same meaning as defined above, or a salt thereof in the presence of a condensing agent (1-ethyl-3-(3-dimethylaminopropyl)carbodiimide, etc.), and, if necessary, removing the protective group for the amino group according to the conventional method. As the protective group for the amino group, any of the same protective groups commonly used as mentioned above R can be suitably used.

Also, the compound [III] wherein B is H, X is —CO— or -Alk-CO— and $R^3$ is (1) a monocyclic or bicyclic nitrogen-containing heterocyclic group which may be substituted or (2) an amino group substituted by 1 or 2 substituents selected from a substituted or unsubstituted lower alkyl group, represented by the formula:

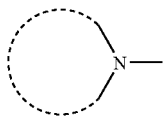

can be prepared by reacting a compound represented by the formula [32]:

  [32]

wherein $V^9$ represents —COOH and $R^1$ has the same meaning as defined above, an amino group-protected material thereof or a salt thereof, with a compound represented by the formula [33a]:

$R^{22}$-Alk-H  [33a]

wherein $R^{22}$ represents (1) a monocyclic or bicyclic nitrogen-containing heterocyclic group which may be substituted or (2) an amino group substituted by 1 or 2 substituents selected from a substituted or unsubstituted lower alkyl group, represented by the formula:

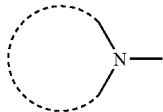

and Alk has the same meaning as defined above, or a salt thereof, in the presence of a condensing agent (1-ethyl-3-(3-dimethylaminopropyl)carbodiimide, etc.), and, if necessary, removing the protective group for the amino group according to the conventional method. As the protective group for the amino group, any of the same protective groups commonly used as mentioned above R can be suitably used.

Also, the compound [III] wherein B is N, X is —CO— or -Alk-CO— and $R^2$ is (1) a monocyclic or bicyclic nitrogen-containing heterocyclic group which may be substituted or (2) an amino group substituted by 1 or 2 substituents selected from a substituted or unsubstituted lower alkyl group, represented by the formula:

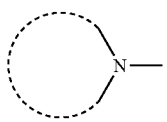

can be prepared by reacting a compound represented by the formula [330]:

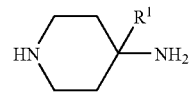  [330]

wherein $R^1$ has the same meaning as defined above, an amino group-protected material thereof or a salt thereof, with the compound represented by the formula [331] or [332]:

$R^{22}CO$—$Z^7$  [331]

$R^{22}$-Alk-COOH  [332]

wherein $R^{22}$ represents (1) a monocyclic or bicyclic nitrogen-containing heterocyclic group which may be substituted or (2) an amino group substituted by 1 or 2 substituents selected from a substituted or unsubstituted lower alkyl group, represented by the formula:

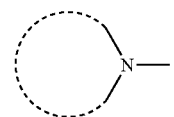

and $Z^7$ represents a reactive residue, or a salt thereof, in the presence or absence of an acid acceptor (for example, an organic base such as triethylamine, diisopropylethylamine, etc., and an inorganic base such as sodium hydride, potassium carbonate, etc.), and, if necessary, removing the protective group for the amino group according to the conventional method. As the protective group for the amino group, any of the same protective groups commonly used as mentioned above R can be suitably used. As the reactive residue of $Z^7$, the same reactive residue commonly used as mentioned above $Z^1$ can be suitably used.

Also, the compound [III] wherein B is CH, X is a single bonding arm and $R^2$ is (1) a monocyclic or bicyclic nitrogen-containing heterocyclic group which may be substituted or (2) an amino group substituted by 1 or 2 substituents selected from a substituted or unsubstituted lower alkyl group, represented by the formula:

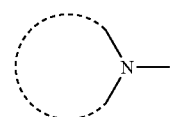

can be prepared by reacting the compound represented by the formula [34]:

  [34]

wherein $R^1$ has the same meaning as defined above, an amino group-protected material thereof or a salt thereof, with a compound represented by the formula [33b]:

R$^{22}$—H  [33b]

wherein R$^{22}$ has the same meaning as defined above, in the presence of a reducing agent (sodium triacetoxyborohydride, etc.), and, if necessary, removing the protective group for the amino group according to the conventional method. As the protective group for the amino group, any of the same protective groups commonly used as mentioned above R can be suitably used.

Also, the compound [III] wherein B is CH, X is a single bonding arm and R$^2$ is a group represented by the formula:

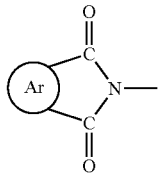

can be prepared by reacting a compound represented by the formula [35]:

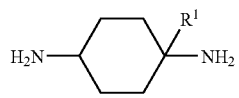
[35]

wherein R$^1$ has the same meaning as defined above, an amino group-protected material thereof or a salt thereof, with a compound represented by the formula [36]:

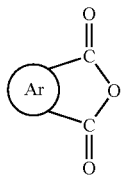

wherein Ar represents an arylene (phenylene, etc.) which may have a substituent(s), in the presence or absence of an acid acceptor (for example, an organic base such as triethylamine, diisopropylethylamine, etc., and an inorganic base such as sodium hydride, potassium carbonate, etc.), and, if necessary, removing the protective group for the amino group according to the conventional method. As the protective group for the amino group, any of the same protective groups commonly used as mentioned above R can be suitably used.

Also, the compound [III] wherein B is CH, X is a single bonding arm and R$^2$ is a nitrogen-containing heterocyclic group represented by the formula:

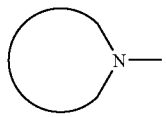

can be prepared by reacting the compound represented by the above-mentioned formula [35], an amino group-protected material thereof or a salt thereof, with a compound represented by the formula [37]

[37]

wherein Z$^{81}$ and Z$^{82}$ both represent a reactive residue, or a salt thereof, in the presence or absence of an acid acceptor (for example, an organic base such as triethylamine, diisopropylethylamine, etc., and an inorganic base such as sodium hydride, potassium carbonate, etc.), and, if, necessary, removing the protective group for the amino group according to the conventional method. As the protective group for the amino group, any of the same protective groups commonly used as mentioned above R can be suitably used.

As the reactive residue of Z$^{81}$ and Z$^{82}$, the same reactive residue commonly used as mentioned above Z$^1$ can be suitably used.

Also, the compound [III] wherein B is N and X is a single bonding arm can be prepared by reacting a compound represented by the formula [38]:

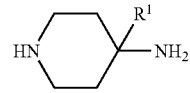
[38]

wherein R$^1$ has the same meaning as defined above, an amino group-protected material thereof or a salt thereof, with the compound represented by the above-mentioned formula [24]:

R$^2$—Z$^4$  [24]

wherein R$^2$ and Z$^4$ have the same meanings as defined above, in the presence or absence of an acid acceptor (for example, an organic base such as triethylamine, diisopropylethylamine, etc., and an inorganic base such as sodium hydride, potassium carbonate, etc.), and, if necessary, removing the protective group for the amino group according to the conventional method. As the protective group for the amino group, any of the same commonly used protective groups as mentioned above R can be suitably used.

Also, the compound [III] wherein X is —COO— can be prepared by reacting an amino group-protected material or a salt of a compound represented by the formula [39]:

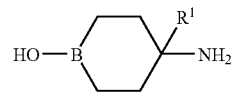
[39]

wherein R$^1$ and B have the same meanings as defined above, with a compound represented by the formula [40]:

R$^2$—COCl  [40]

wherein R$^2$ has the same meaning as defined above, in the presence of an acid acceptor (dimethylaminopyridine, etc.), and, if necessary, removing the protective group for the amino group according to the conventional method. As the protective group for the amino group, any of the same protective groups commonly used as mentioned above R can be suitably used.

The starting materials [20] to [40] can be prepared according to the known methods or in the same manner as mentioned in Reference Examples below. In the starting material [III] wherein B is CH, cis/trans isomers are present, taking a cyclohexane ring as a standard plane. In this case, it is possible to obtain a desired form of isomer of the starting material [III] by using a suitable isomer of the starting cyclohexane compound, corresponding to each of desired products.

Alternatively, a mixture of cis/trans isomers is obtained as a starting material [III], and then, a desired isomer can be separated by means of chromatography, etc.

(Starting Material of Process B)

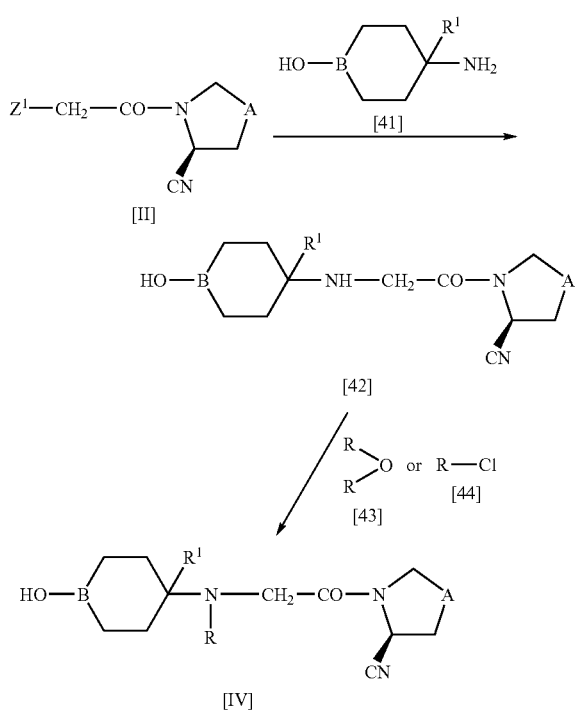

wherein R, $R^1$, $Z^1$, A and B have the same meanings as defined above.

A compound represented by the formula [IV] or a salt thereof can be prepared by reacting the compound represented by the above formula [II] with a compound represented by the formula [41] or a salt thereof to obtain a compound represented by the formula [42] or a salt thereof, and further reacting the same with a compound represented by the formula [43] or the formula [44].

Reaction between the compound [II] and the compound [41] or a salt thereof can be carried out in the presence or absence of an acid acceptor, in a suitable solvent or without solvent. As the solvent, any solvents may be suitable as long as it is not adversely affected to the reaction, and, for example, acetonitrile, methanol, ethanol, isopropyl alcohol, propyl alcohol, acetone, dimethylformamide, dimethyl sulfoxide, tetrahydrofuran, ether, dioxane, ethyl acetate, toluene, methylene chloride, dichloroethane, chloroform or a mixed solvent thereof can be suitably used. This reaction suitably proceeds at 0 to 120° C., particularly at room temperature to 80° C.

As the acid acceptor, an inorganic base (for example, alkali metal hydride such as sodium hydride, alkali metal carbonate such as sodium carbonate and potassium carbonate, alkali metal alkoxide such as sodium methoxide, alkali metal such as sodium, and alkali metal hydroxide such as sodium hydroxide and potassium hydroxide, etc.) or an organic base (for example, triethylamine, diisopropylethylamine, N-methylmorpholine, pyridine, dimethylaniline, dimethylaminopyridine, etc.) can be suitably used.

Reaction between the compound [42] or a salt thereof and the compound [43] or [44] can be carried out in the presence of an acid acceptor, in a suitable solvent or without solvent.

As the solvent, any solvents may be suitable as long as it is not adversely affected to the reaction, and, for example, acetonitrile, methanol, ethanol, isopropyl alcohol, propyl alcohol, acetone, tetrahydrofuran, ether, dioxane, ethyl acetate, toluene, methylene chloride, dichloroethane, chloroform, water or a mixed solvent thereof can be suitably used. This reaction suitably proceeds at 0 to 120° C., particularly at room temperature to 80° C.

As the acid acceptor, an inorganic base (for example, alkali metal hydride such as sodium hydride, alkali metal carbonate such as sodium carbonate and potassium carbonate, alkali metal alkoxide such as sodium methoxide, alkali metal such as sodium, and alkali metal hydroxide such as sodium hydroxide and potassium hydroxide, etc.) or an organic base (for example, triethylamine, diisopropylethylamine, N-methylmorpholine, pyridine, dimethylaniline, dimethylaminopyridine, etc.) can be suitably used.

(Starting Materials of Process C and Process D)

The compound [VII], the compound [IX] or the compound [XIII] can be each obtained by reacting a compound represented by the formula [50], [51] or [52]:

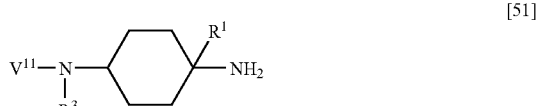

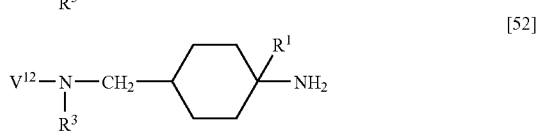

wherein $V^{10}$, $V^{11}$ and $V^{12}$ represent protective groups for the amino group, and $R^1$ and $R^3$ have the same meanings as defined above, with a compound represented by the formula [53]:

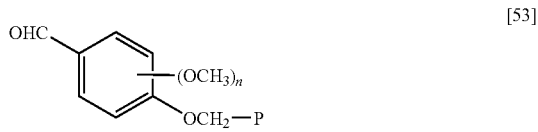

wherein P and n have the same meanings as defined above, according to a conventional method, in the presence of a reducing agent (for example, sodium triacetoxyborohydride, etc.), subsequently reacting the product in the presence of the compound [II] and an acid acceptor (diisopropylethylamine, etc.), and then, removing the protective group for the amino group according to the conventional method. As the protective group for the amino group, any of the same protective groups commonly used as mentioned above R can be suitably used.

The compound [I] of the present invention or its starting material prepared according to the above is, isolated in a free form or as a salt thereof, and purified. Salts can be prepared by subjecting to the salt-forming treatment conventionally used.

Isolation and purification can be carried out by applying the usual chemical operations such as extraction, concentration, crystallization, filtration, recrystallization, various kinds of chromatographies and the like.

For the compound of the present invention and a starting material thereof, optical isomers, such as racemic modifications, optically active substances, diastereomers, etc. can be present alone or as mixtures thereof.

A stereochemically pure isomer can be derived by using a stereochemically pure starting material or by separating an optical isomer according to the general separation process for racemic resolution. Also, diastereomeric mixtures can be separated according to the conventional method, for example, fractional crystallization or by chromatography.

EXAMPLES

The present invention will be described in detail by referring to the following Examples but these Examples do not intend to limit the present invention.

Example 1-1

An acetonitrile-methanol solution containing 100 mg of (S)-1-bromoacetyl-2-cyanopyrrolidine (Reference Example 1 mentioned below) and 247 mg of 4-amino-1-(2-pyrimidinyl)-piperidine (Reference Example 7-1 mentioned below) was stirred at room temperature for 15 hours. Water was added to the reaction mixture and the mixture was extracted with chloroform. After the extract was dried over anhydrous sodium sulfate, the solvent was removed under reduced pressure. The residue was purified by diol column chromatography (solvent: 0 to 10% methanol-chloroform), and dissolved in 0.5 ml of ethyl acetate-0.5 ml of chloroform. Added thereto were 1.0 ml of 2N hydrochloric acid-ether, followed by 2 ml of ether. The resulting precipitates were collected by filtration and washed with ether to obtain (S)-2-cyano-1-[1-(2-pyrimidinyl)piperidin-4-ylamino]-acetylpyrrolidine-dihydrochloride (Example 1-1 in Table 1).

Examples 1-2 to 1-90, 1-92 to 1-109

The compounds of Table 1 shown below (Examples 1-2 to 1-90, 1-92 to 1-109) were obtained in the same manner as in the above-mentioned Example 1-1 by using (S)-1-bromoacetyl-2-cyanopyrrolidine and corresponding starting materials. (Provided that the compound of Example 1-93 was obtained as a by-product of Example 1-33.)

(The corresponding starting materials were obtained in the same manner as described in Reference Examples mentioned below, by known methods or by a method in combination of these methods.)

Example 1-91

570 mg of (S)-1-bromoacetyl-2-cyanopyrrolidine was added to 5 ml of an acetonitrile solution containing 300 mg of trans-1,4-cyclohexanediamine and 457 µL of N,N-diisopropylethylamine, and the mixture was stirred at room temperature for 3 hours. The reaction mixture was diluted with brine and extracted with chloroform. After the extract was dried over anhydrous sodium sulfate, the solvent was removed under reduced pressure. The residue was purified by silica gel column chromatography (solvent: chloroform-methanol (100:0 to 95:5)) to obtain an oily product. The oily product was dissolved in 0.5 ml of chloroform, and added thereto were 0.5 ml of 1N hydrochloric acid-ether, followed by 4 ml of ether. The resulting precipitates were washed with ether to obtain 307 mg of (S)-2-cyano-1-{trans-4-[(S)-(2-cyano-1-pyrrolidinyl)carbonylmethylamino]
cyclohexylamino}acetylpyrrolidine.dihydrochloride (Example 1-91 in Table 1).

Examples 2-1 to 2-9

(1) A mixture comprising 600 mg of 4-tert-butoxycarbonylamino-4-methylcyclohexanone (the compound of Reference Example 6-1 (3)), 783 mg of sodium triacetoxyborohydride, 252 mg of morpholine, 159 mg of acetic acid and 6 ml of dichloroethane was stirred at room temperature for 16 hours. The mixture was diluted with an aqueous saturated sodium hydrogencarbonate solution and extracted with chloroform. The extract was dried over anhydrous sodium sulfate and the solvent was removed under reduced pressure. The residue was purified by silica gel column chromatography (solvent: chloroform-methanol (20:1) to chloroform-methanol (10:1)+ 1% aqueous ammonia) to obtain 600 mg of a mixture of N-tert-butoxycarbonyl-1-methyl-c-4-morpholino-r-1-cyclohexylamine and N-tert-butoxycarbonyl-1-methyl-t-4-morpholino-r-1-cyclohexylamine (Reference Example 8-54; a compound before deprotection). 220 mg of this compound was stirred in a mixed solution of 2 ml of 4N hydrochloric acid-dioxane and 2 ml of ethanol at room temperature for 15 hours to deprotect the N-tert-butoxycarbonyl group, and then, the reaction mixture was concentrated to obtain a residue.

(2) To the compound obtained in the above (1) were added 320 mg of (S)-1-bromoacetyl-2-cyanopyrrolidine, 0.6 ml of triethylamine, 3.5 ml of acetonitrile and 1 ml of methanol, and the mixture was stirred at room temperature for 15 hours. The mixture was diluted with an aqueous saturated sodium hydrogencarbonate solution and extracted with chloroform. The extract was dried over anhydrous sodium sulfate and the solvent was removed under reduced pressure. The residue was purified by silica gel column chromatography (solvent: chloroform-hexane (1:1) to chloroform) to obtain 2 kinds of oily products.

The compound with lower polarity was treated with hydrochloric acid to obtain 33 mg of (S)-2-cyano-1-[1-methyl-c-4-morpholino-r-1-cyclohexylamino]acetylpyrrolidine.dihydrochloride (Example 2-1 in Table 2). Also, the compound with higher polarity was treated with hydrochloric acid to obtain 82 mg of (S)-2-cyano-1-[1-methyl-t-4-morpholino-r-1-cyclohexylamino]acetylpyrrolidine.dihydrochloride (Example 2-2 in Table 2).

The compounds of Examples 2-3 to 2-9 in Table 2 were obtained in the same manner as mentioned above.

Example 3

(1) To 60 ml of acetonitrile-methanol (3/1) mixed solution containing 4.78 g of trans-4-aminocyclohexanol was added 3.00 g of (S)-1-bromoacetyl-2-cyanopyrrolidine under ice-cooling, and the mixture was stirred at room temperature for 14 hours. To the reaction mixture were added 1.93 ml of triethylamine, followed by 16 ml of an acetonitrile solution containing di-tert-butyldicarbonate at room temperature, and the mixture was stirred for 3 hours as such. After the solvent was removed under reduced pressure, water was added to the residue, and then neutralized with an aqueous sodium hydrogencarbonate solution. The mixture was then extracted with chloroform, dried and concentrated. The obtained residue was purified by silica gel column chromatography to obtain 4.72 g of (S)-1-(N-tert-butoxycarbonyl-trans-4-hydroxy-1-cyclohexylamino)acetyl-2-cyanopyrrolidine.

(2) 84 mg of triphosgene was added to 2 ml of a methylene chloride solution containing 150 mg of the compound obtained in the above (1) and 121 µL of pyridine at room temperature, and the mixture was stirred for 1 hour as such. Subsequently, to the mixture was added 1 mL of a methylene chloride solution containing 186 µL of morpholine, and the mixture was stirred at room temperature for 1 hour and diluted with an aqueous citric acid solution. The mixture was extracted with ethyl, acetate, dried and concentrated. Subsequently, it was purified by silica gel column chromatography to obtain 174 mg of (S)-1-[N-tert-butoxycarbonyl-trans-4-(morpholinocarbonyloxy)cyclohexylamino]acetyl-2-cyanopyrrolidine.

(3) 157 mg of the compound obtained in the above (2) was dissolved in 1.5 mL of trifluoroacetic acid and the mixture was stirred at room temperature for 1 hour. The solvent was removed under reduced pressure, and then, an aqueous sodium hydrogencarbonate solution was added to the residue, making the solution alkaline. The mixture was extracted with chloroform, dried and concentrated. Subsequently, the resulting residue was purified by column chromatography (solvent: 0 to 5% methanol-chloroform) to obtain an oily product. This was dissolved in 1 mL of ethyl acetate and added thereto were 0.5 mL of 1N hydrochloric acid-ether, followed by 2 mL of ether. The resulting precipitates were washed with ether to obtain 97 mg of (S)-2-cyano-1-[trans-4-(morpholinocarbonyloxy)cyclohexylamino]acetylpyrrolidine hydrochloride (Example 3 in Table 3).

Example 4-1

(1) A mixture comprising 500 mg of the resin compound obtained in Reference Example 3 (2) mentioned below and 0.5M methanesulfonic acid in dioxane-methylene chloride (1/9) was stirred at room temperature for 18 hours. The resin was collected by filtration and washed with dimethyl formamide, 10% triethylamine-methylene chloride, dimethylformamide-water (1:1), methanol, tetrahydrofuran, methanol and methylene chloride. A mixture comprising the obtained resin, 277 µl of benzyl isocyanate and 4 ml of methylene chloride was stirred at room temperature for 18 hours. The resin was collected by filtration and washed with dimethylformamide, dimethylformamide-water (1:1), methanol, tetrahydrofuran, methanol and methylene chloride, and dried under reduced pressure to obtain a resin.

(2) A mixture comprising the resin obtained in the above (1) and 4 ml of trifluoroacetic acid was stirred at room temperature for 18 hours. The resin was removed by filtration and washed with methylene chloride, and the filtrate and the washing solution were combined and concentrated. To the resulting residue was added an aqueous sodium hydrogencarbonate solution, thereby making the solution alkaline. Subsequently it was extracted with chloroform, dried and concentrated. The obtained residue was purified by diol column chromatography (solvent: 0 to 5% methanol-chloroform) to obtain an oily product. This was dissolved in 0.5 ml of ethyl acetate and added thereto were 0.5 ml of 1N hydrochloric acid-ether, followed by 2 ml of ether. The resulting precipitates were washed with ether to obtain (S)-2-cyano-1-[1-(benzylaminocarbonyl)piperidin-4-ylamino]-acetylpyrrolidine-hydrochloride (Example 4-1 in Table 4).

Examples 4-2 to 4-5

The compounds of Examples 4-2 and 4-3 in Table 4 were obtained in the same manner as in Example 4-1, using the corresponding starting materials (isocyanate compounds). Also, the compounds of Examples 4-4 and 4-5 in Table 4 were obtained in the same manner as in Example 4-1, using intramolecular cyclic anhydride of dicarboxylic acid (succinic anhydride and glutaric anhydride) as starting materials in place of the isocyanate compound.

Examples 4-6 to 4-10

The compound of Examples 4-6 in Table 4 was obtained in the same manner as in Example 4-1, except for using methylchloroformate as a starting material in place of benzyl isocyanate, and carrying out the reaction of the section (1) in the presence of triethylamine. Also, the compounds of Examples 4-7 to 4-10 were obtained in the same manner as mentioned above, using a corresponding starting material (chloride).

Example 4-11

A mixture comprising 500 mg of the resin compound obtained in the Reference Example 3 (2) and 0.5M methanesulfonic acid in dioxane/methylene chloride (1/9) was stirred at room temperature for 18 hours. The resin was collected by filtration and was washed with dimethylformamide, 10% triethylamine-methylene chloride, dimethylformamide-water (1:1), methanol, tetrahydrofuran, methanol and methylene chloride. A mixture of the obtained resin, 177 mg of 2-quinolinecarboxylic acid, 138 mg of 1-hydroxy-benzotriazol, 387 mg of O-benzotriazol-1-yl-N,N,N',N'-tetramethyluronium hexafluorophosphate, 224 ml of N-methylmorpholine and 4 ml of dimethylformamide was stirred at room temperature for 18 hours. The resin was collected by filtration and washed with dimethylformamide, dimethylformamide-water (1:1), methanol, tetrahydrofuran, methanol and methylene chloride, and dried under reduced pressure to obtain a resin. This resin was treated with trifluoroacetic acid in the same manner as in Example 4-1 (2) to obtain 136 mg of (S)-2-cyano-1-[1-(2-quinolylcarbonyl)-1-piperidin-4-ylamino]acetylpyrrolidine.dihydrochloride (Example 4-11 in Table 4).

Examples 4-12 to 4-19

The compounds of Examples 4-12 to 4-19 in Table 4 were obtained in the same manner as in Example 4-11 by using corresponding starting materials (carboxylic acid compounds).

Examples 5-1 to 5-12

The compounds of Examples 5-1 to 5-12 in Table 5 were obtained in the same manner as in Examples 4-1 to 4-10 by using a resin compound obtained in Reference Example 4 in place of the resin compound of Reference Example 3 (2).

Examples 5-13 to 5-36

The compounds of Examples 5-13 to 5-30 in Table 5 were obtained in the same manner as in Example 4-1, using a resin compound obtained in Reference Example 4 in place of the resin compound of Reference Example 3 (2). Also, the compounds of Examples 5-31 to 5-36 in Table 5 were obtained in the same manner by using a resin compound obtained in Reference Example 5 (5).

Examples 5-37 to 5-39

A mixture comprising 500 mg of the resin compound obtained in the Reference Example 5 (5) and 0.5M methanesulfonic acid in dioxane/methylene chloride (1/9) was shaken at room temperature for 30 minutes. The resin was collected by filtration and was washed with methylene chloride, 10% triethylamine-methylene chloride, methylene chloride, dimethylformamide, dimethylformamide-water (1:1), tetrahydrofuran, methanol, tetrahydrofuran, methanol and dimethylacetamide. A mixture of the obtained resin, 293 mg of 2-chloro-5-bromopyrimidine and 211 μl of triethylamine was shaken at 55° C. for 16 hours. The resin was collected by filtration and washed with dimethylformamide, methylene chloride, 10% triethylamine-methylene chloride, methylene chloride, dimethylformamide, dimethylformamide-water (1:1), tetrahydrofuran, methanol, tetrahydrofuran, methanol and methylene chloride. Whole amount of the obtained resin was treated with trifluoroacetic acid to obtain 61 mg of (S)-1-[trans-4-(5-bromopyrimidin-2-ylaminomethyl)cyclohexylamino]acetyl-2-cyanopyrrolidine.hydrochloride (Example 5-37 in Table 5).

Also, the compounds of Examples 5-38 to 5-39 were obtained in the same manner by using corresponding starting materials.

Example 6-1

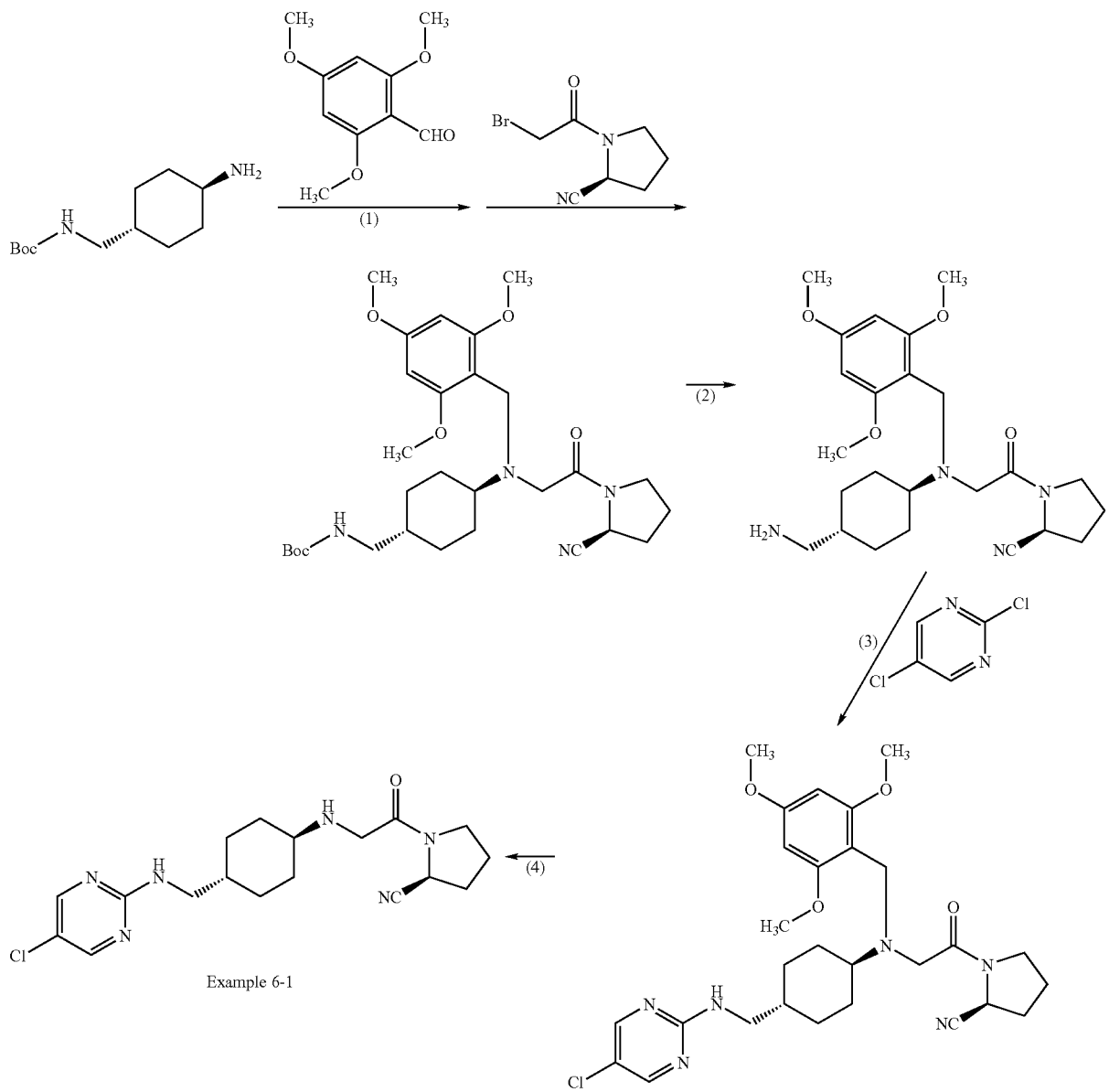

Example 6-1

(1) A mixture comprising 519 mg of trans-4-(tert-butoxycarbonylaminomethyl)cyclohexylamine (Reference Example 5 (3) mentioned below), 446 mg of 2,4,6-trimethoxybenzaldehyde, 608 mg of sodium triacetoxyborohydride and 11 mL of methylene chloride was stirred at room temperature for 14 hours. The reaction mixture was diluted with an aqueous saturated sodium hydrogencarbonate solution and extracted with chloroform. The extract was washed with brine, dried over anhydrous sodium sulfate, and the solvent was removed under reduced pressure. The residue was purified by diol column chromatography (solvent: 0-20% methanol-chloroform). A mixture of the obtained compound (969 mg), 641 mg of (S)-1-bromoacetyl-2-cyanopyrrolidine, 791 µl of diisopropylethylamine and 8 ml of dimethylacetamide was stirred at 50° C. for 1 hour. The reaction mixture was diluted with water and extracted with ethyl acetate. The extract was washed with water and brine, dried over anhydrous sodium sulfate, and the solvent was removed under reduced pressure. The residue was purified by diol column chromatography (solvent: 50-0% hexane-chloroform) to obtain 834 mg of (S)-2-cyano-1-[N-(2,4,6-trimethoxyphenylmethyl)-trans-4-(tert-butoxycarbonylaminomethyl)cyclohexylamino]acetylpyrrolidine.

(2) A mixture comprising 818 mg of the compound obtained in the above (I) and 20 mL of 0.5M methanesulfonic acid in dioxane/methylene chloride (1/9) was stirred at room temperature for 2 hours. The reaction mixture was diluted with an aqueous saturated sodium hydrogencarbonate solution and extracted with chloroform. The extract was washed with brine, dried over anhydrous sodium sulfate, and the solvent was removed under reduced pressure to obtain 647 mg of (S)-2-cyano-1-[N-(2,4,6-trimethoxyphenylmethyl)-trans-4-(aminomethyl)cyclohexylamino]acetylpyrrolidine.

(3) A mixture comprising 155 mg of the compound obtained in the above (2), 104 mg of 2,5-dichloropyrimidine, 146 µL of triethylamine, 1 mL of tetrahydrofuran, and 1 mL of dimethylformamide was stirred at 60° C. for 14 hours. The reaction mixture was diluted with water, and extracted with ethyl acetate. The extract was washed with water and brine, dried over anhydrous sodium sulfate, and then, the solvent was removed under reduced pressure. The residue was purified by diol column chromatography (solvent: 0-20% methanol-(33% hexane-chloroform)) to obtain 104 mg of (S)-2-cyano-1-[N-(2,4,6-trimethoxyphenylmethyl)-trans-4-(5-chloropyrimidin-2-ylaminomethyl)cyclohexylamino]acetylpyrrolidine.

(4) A mixture comprising 90 mg of the compound obtained in the above (3) and 4 mL of trifluoroacetic acid was stirred at room temperature for 18 hours. After trifluoroacetic acid was removed under reduced pressure, an aqueous saturated sodium hydrogencarbonate solution was added to the residue, and the mixture was extracted with chloroform. The extract was dried over anhydrous sodium sulfate, and the solvent was removed under reduced pressure. The residue was purified by diol column chromatography (solvent: 40-0% hexane-chloroform). The obtained compound was dissolved in 0.5 mL of chloroform, and were added thereto 0.5 mL of 1N hydrochloric acid-ether, followed by 2 mL of ether. The resulting precipitates were washed with ether to obtain 22 mg of (S)-1-[trans-4-(5-chloropyrimidin-2-ylaminomethyl)cyclohexylamino]acetyl-2-cyanopyrrolidine dihydrochloride (Example 6-1 in Table 6).

Examples 6-2 to 6-4

The compounds of Examples 6-2 to 6-4 in Table 6 were obtained in the same manner as in Example 6-1 (3) and (4) by using the compound obtained in the above Example 6-1 (2) and corresponding starting materials.

Examples 7-1 to 7-10

The compounds of Examples 7-1 to 7-10 in Table 7 were obtained in the same manner as mentioned above Example 1 by using (R)-3-chloroacetyl-4-cyanothiazolidine (a compound in Reference Example 2 mentioned below) in place of (S)-1-bromoacetyl-2-cyanopyrrolidine.

Examples 8-1 to 8-8

(R)-4-cyano-3-[N-(2,4,6-trimethoxyphenylmethyl)-trans-4-aminomethylcyclohexylamino]acetylthiazolidine was obtained in the same manner as in Example 6-1 (1) and (2) by using (R)-3-chloroacetyl-4-cyanothiazolidine in place of (S)-1-bromoacetyl-2-cyanopyrrolidine. By using this compound and corresponding starting materials, the compounds of Examples 8-1 to 8-8 in Table 8 were obtained in the same manner as in Examples 6-1 (3) and (4). (Provided that in case of Examples 8-7 and 8-8, in the process corresponding to Example 6-1 (3), a carboxylic acid compound was used as a starting material, and the reaction was carried out in the presence of 1-hydroxybenzotriazole and 1-ethyl-3-(3-dimethylaminopropyl)-carbodiimide.)

Reference Example 1

According to the process described in the literature (WO98/19998), (S)-1-bromoacetyl-2-cyanopyrrolidine was obtained by reacting L-prolineamide (commercially available product) and bromoacetyl bromide, followed by dehydration.

Reference Example 2

L-thioprolineamide hydrochloride was synthesized according to the process described in the literature (Ashworth et. al, Bioorg. Med. Chem. Lett., Vol. 6, pp. 2745-2748, 1996). 2.36 ml of chloroacetyl chloride was added to 150 ml of a dichloromethane solution containing 5.00 g of the thus obtained L-thioprolineamide hydrochloride and 8.67 ml of triethylamine under ice-cooling, and the mixture was stirred at the same temperature for 1 hour. To the reaction mixture were added 4.8 ml of pyridine and 8.4 ml of trifluoroacetic anhydride, and the mixture was further stirred at room temperature for 1 hour. The reaction mixture was washed with an aqueous 10% HCl solution and water, dried over magnesium sulfate, filtered and concentrated under reduced pressure. Subsequently, the residue was crystallized from ether to obtain 4.82 g of (R)-3-chloroacetyl-4-cyanothiazolidine as a yellowish brown crystal.

Reference Examples 3

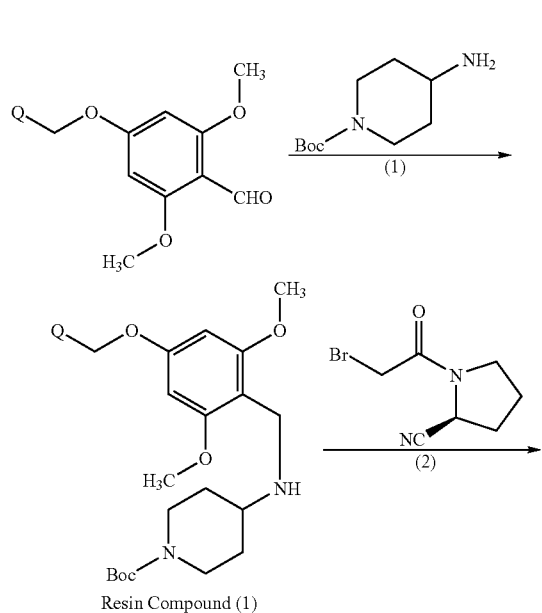

Resin Compound (1)

Reference Example 3
Resin Compound (2)

Boc: tert-butoxycarbonyl group
Q: polystyrene residue (1) A mixture comprising 14.5 g (1.40 mmol/g) of a resin ((4-formyl-3,5-dimethoxyphenyloxy)methyl polystyrene) [synthesized according to a method of Cecile Pegurier et al., (Bioorg. Med. Chem., Vol. 8, pp. 163-171, 2000), 7.85 g of 4-amino-1-tert-butoxycarbonylpiperidine, 10.71 g of sodium triacetoxyborohydride, and 180 ml of methylene chloride was stirred at room temperature for 18 hours. The resin was collected by filtration, and washed with methylene chloride, dimethylformamide-water (1:1), 10% triethylamine-methylene chloride, dimethylformamide-water (1:1), methanol, tetrahydrofuran and methanol. Subsequently, it was dried under reduced pressure to obtain 16.83 g (1.17 mmol/g) of a resin compound [1] shown in the above figure.

(2) A mixture comprising 16.73 g of the resin compound obtained in the above (1), 8.50 g of (S)-1-bromoacetyl-2-cyanopyrrolidine, 6.82 ml of diisopropylethylamine, and 80 ml of dimethylformamide was stirred at 50° C. for 18 hours. The resin was collected by filtration, and washed with dimethylformamide, 10% triethylamine-methylene chloride, dimethylformamide-water (1:1), methanol, tetrahydrofuran and methanol. Subsequently, it was dried under reduced pressure to obtain 19.14 g (1.02 mmol/g) of a resin compound (2) shown in the above figure.

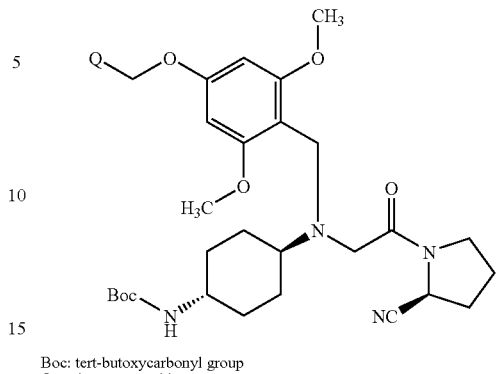

Boc: tert-butoxycarbonyl group
Q: polystyrene residue

Reference Example 4

To 250 ml of an ethanol solution containing 30.00 g of 1,4-trans-cyclohexane diamine and 131 ml of 2N hydrochloric acid was added dropwise over 4 hours 150 ml of an ethanol solution containing 52.13 g of di-tert-butyl-dicarbonate under ice-cooling. The reaction mixture was stirred for 20 hours, concentrated and diluted with an aqueous citric acid solution. It was then washed with chloroform and made alkaline by an aqueous sodium hydroxide solution. The solution was extracted with chloroform, dried, and concentrated to obtain 22.33 g of N-tert-butoxycarbonyl-trans-1,4-cyclohexanediamine.

Using this compound and a resin ((4-formyl-3,5-dimethoxyphenyloxy)methyl polystyrene), the resin compound shown in the above figure was obtained in the same manner as mentioned above Reference Example 3 (1) and (2).

Reference Example 5

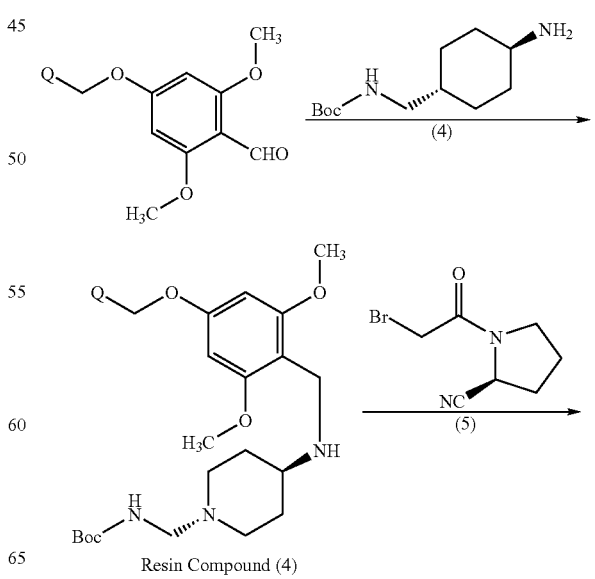

Resin Compound (4)

-continued

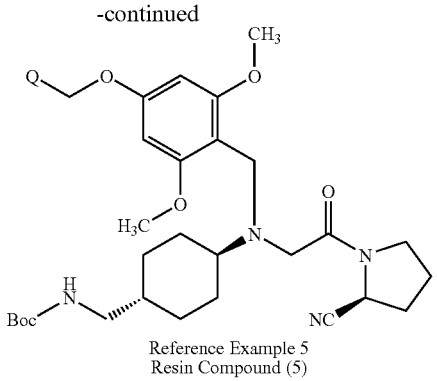

Reference Example 5
Resin Compound (5)

Boc: tert-butoxycarbonyl group
Q: polystyrene residue (1) 200 ml of a dioxane-water (1:1) solution containing 10.0 g of trans-4-aminomethylcyclohexanecarboxylic acid, 14.6 g of di-tert-butyldicarbonate and 11.2 g of sodium bicarbonate was stirred at room temperature for 7.2 hours. To the reaction mixture were added 50 ml of an aqueous 10% NaOH solution and 300 ml of ether, and an organic phase was separated. Subsequently, an aqueous phase was made acidic by an aqueous 10% HCl solution, and extracted with ethyl acetate. The extract was washed with brine, dried over anhydrous sodium sulfate, and the solvent was removed under reduced pressure. The residue was washed with isopropyl ether to obtain 15.3 g of trans-4-(tert-butoxycarbonyl-aminomethyl)cyclohexanecarboxylic acid.

(2) After 100 ml of a toluene solution containing 5.15 g of the compound obtained in the above (1), 6.05 g of diphenylphosphoryl azide and 3.1 ml of triethylamine was refluxed for 3 hours, 2.3 ml of benzyl alcohol was added thereto and the mixture was further refluxed overnight. After cooling, the reaction mixture was concentrated, and the residue was purified by silica gel flash column chromatography (solvent: ethyl acetate-chloroform (1:20)), and crystallized from hexane to obtain 5.32 g of N-benzyloxycarbony-trans-4-(tert-butoxycarbonylaminomethyl)cyclohexylamine.

(3) 200 ml of an ethanol solution containing 5.19 g of the compound obtained in the above 2) and 10% palladium-carbon was stirred under hydrogen atmosphere at 1 atm for 6 hours. The catalyst was removed by filtration and the filtrate was washed with ethanol. The filtrate and the washing solution were combined. The solvent was removed under reduced pressure and the residue was purified by silica gel column chromatography (solvent: chloroform-methanol-concentrated aqueous ammonia (50:10:1)) and crystallized from a mixed solvent of isopropyl ether-hexane to obtain 2.55 g of trans-4-(tert-butoxycarbonylaminomethyl)cyclohexylamine.

(4) A mixture comprising the compound obtained in the above (3) (2.54 g), 4.15 g (1.43 mmol/g) of a resin ((4-formyl-3,5-dimethoxyphenyloxy)methyl polystyrene, 3.24 g of sodium triacetoxyborohydride and 80 ml of methylene chloride was stirred at room temperature for 20 hours. The resin was collected by filtration, and washed with methylene chloride, dimethylformamide, methylene chloride, 10% triethylamine-methylene chloride, methylene chloride, dimethylformamide, dimethylformamide-water (1:1), dimethylformamide, methanol, tetrahydrofuran, methanol, tetrahydrofuran and methanol. Subsequently, it was dried under reduced pressure to obtain 5.19 g (1.14 mmol/g) of a resin compound (4) shown in the above-mentioned figure.

(5) A mixture comprising 5.12 g (1.14 mmol/g) of the resin obtained in the above (4), 2.53 g of (S)-1-bromoacetyl-2-cyanopyrrolidine, 2.03 ml of diisopropylethylamine and 50 ml of dimethylformamide was stirred at 50° C. for 18 hours. The resin was collected by filtration, and washed with dimethylformamide, dimethylformamide-water (1:1), dimethylformamide, methanol, tetrahydrofuran, methanol, tetrahydrofuran and methanol. Subsequently, it was dried under reduced pressure to obtain 5.78 g (1.01 mmol/g) of a resin compound (5) shown in the above figure.

Reference Example 6-1

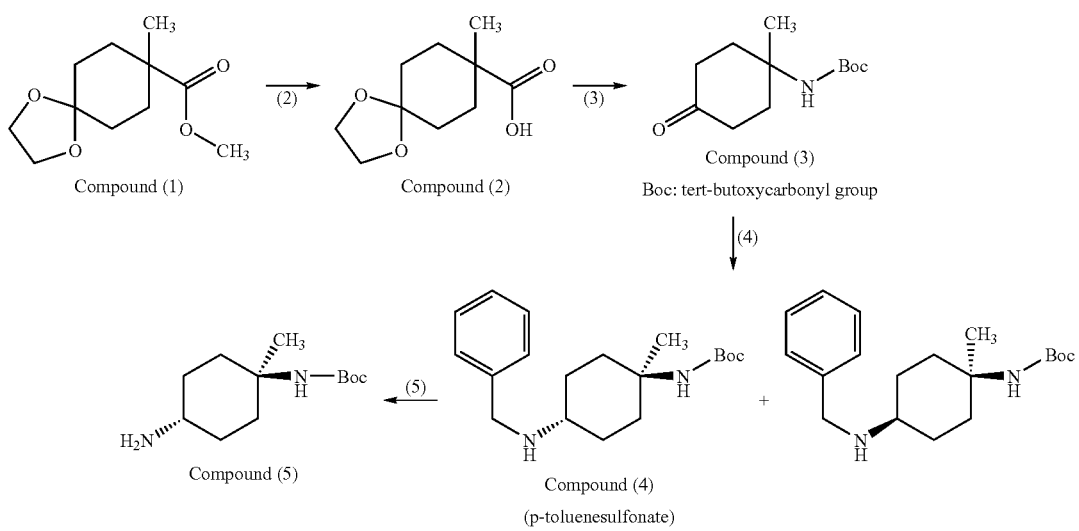

Compound (1) → Compound (2) → Compound (3)
Boc: tert-butoxycarbonyl group

Compound (5) ← Compound (4) (p-toluenesulfonate)

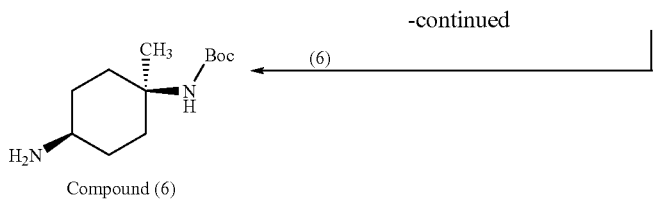

Compound (6)

(1) According to the process described in the literature (JP83-118577), methyl 1,4-dioxaspiro[4.5]decan-8-carboxylate was reacted with methyl iodide in the presence of LDA (lithium diisopropylamide) to obtain methyl 8-methyl-1,4-dioxaspiro[4,5]decan-8-carboxylate (the compound (1) of the above figure).

(The starting material was synthesized according to the processes described in the literature by Rosemmund et al. (Chem. Ber., 1975, Vol. 108, pp. 1871-1895) and the literature by Black et al. (Synthesis, 1981, p. 829).)

(2) A mixture comprising 3.80 g of the compound obtained in the above (1), 3.55 g of sodium hydroxide, 16 mL of methanol and 25 mL of water was refluxed for 2 hours. The reaction mixture was ice-cooled, adjusted to pH 5 by 2N hydrochloric acid and an aqueous 10% citric acid solution, and extracted with ethyl acetate. The extract was washed with water and brine, dried over anhydrous sodium sulfate and the solvent was removed under reduced pressure to obtain 3.46 g of 8-methyl-1,4-dioxaspiro[4.5]decan-8-carboxylic acid (the compound (2) of the above figure).

(3) A mixture comprising 16.19 g of the compound obtained in the above (2), 24.51 g of diphenylphosphoryl azide, 9.00 g of triethylamine and 160 mL of toluene was refluxed for 2.5 hours. The reaction mixture was ice-cooled, washed with an aqueous saturated sodium hydrogencarbonate solution, water and brine, and dried over anhydrous sodium sulfate. Subsequently, the solvent was removed under reduced pressure. 9.55 g of potassium tert-butoxide was slowly added to 100 mL of a dimethylacetamide solution containing the resulting compound under ice-cooling, and the mixture was stirred at room temperature for 1 hour. The reaction mixture was poured into ice-water, and the precipitated crystal was collected by filtration, washed with water and dried. To 100 mL of a tetrahydrofuran solution containing the resulting compound was added 100 mL of an aqueous solution containing 30.87 g of p-toluenesulfonic acid hydrate, and the mixture was stirred at room temperature for 16 hours. The mixture was diluted with an aqueous saturated sodium hydrogencarbonate solution and extracted with ethyl acetate. The extract was washed with water and brine, dried over anhydrous sodium sulfate, and the solvent was removed under reduced pressure to obtain 10.41 g of 4-tert-butoxycarbonylamino-4-methylcyclohexanone (the compound (3) of the above figure).

(4) A mixture comprising 10.41 g of the compound obtained in the above (3), 11.01 g of sodium triacetoxyborohydride, 5.10 mL of benzylamine and 150 mL of methylene chloride was stirred at room temperature for 16 hours. The mixture was diluted with an aqueous saturated sodium hydrogencarbonate solution and extracted with ethyl acetate. The extract was washed with water and brine, dried over anhydrous sodium sulfate and the solvent was removed under reduced pressure. To 15 mL of a methanol solution containing the resulting compound were added 3.32 g of p-toluenesulfonic acid, followed by 160 mL of ether. The precipitates were collected by filtration, washed with ether and dried to obtain 7.49 g of N-benzyl-t-4-tert-butoxycarbonylamino-4-methyl-r-1-cyclohexylamine p-toluenesulfonate (the compound (4) of the above figure).

(5) A mixture comprising 16.63 g of the compound obtained in the above (4), 5.0 g of 10% palladium-carbon and 400 mL of methanol was stirred under hydrogen atmosphere (1 atm) for 24 hours. 10% palladium-carbon was removed by filtration and the filtrate was concentrated. The resulting residue was dissolved in a mixture of 50 mL of an aqueous 10% sodium hydroxide solution and 300 mL of ether. The ether layer was washed with water and brine, dried over anhydrous sodium sulfate and the solvent was removed under reduced pressure to obtain 6.87 g of t-4-tert-butoxycarbonylamino-4-methyl-r-1-cyclohexylamine (the compound (5) of the above figure).

(6) The filtrate in the step of the above (4) was treated with an aqueous sodium hydroxide solution and extracted with chloroform. The extract was washed with water and brine, dried over anhydrous sodium sulfate and the solvent was removed under reduced pressure. The residue was applied to NH-silica gel column chromatography (solvent: hexane-ethyl acetate (30:1 to 3:1)) to obtain N-benzyl-c-4-tert-butoxycarbonylamino-4-methyl-r-1-cyclohexylamine. Next, this compound was treated in the same manner as mentioned above (5) to obtain c-4-tert-butoxycarbonylamino-4-methyl-r-1-cyclohexylamine (the compound (6) of the above figure).

Reference Example 6-2 t-4-tert-Butoxycarbonylamino-4-hydroxymethyl-r-1-cyclohexylamine or c-4-tert-butoxycarbonylamino-4-hydroxymethyl-r-1-cyclohexylamine was obtained in the same manner as in Reference 6-1 (1) to (5) or (6) except for using benzyloxymethyl chloride in place of methyl iodide in the step of Reference Example 6-1 (1).

Also, t-4-tert-butoxycarbonylamino-4-methoxymethyl-r-1-cyclohexylamine or c-4-tert-butoxycarbonylamino-4-methoxymethyl-r-1-cyclohexylamine was obtained in the same manner as Reference Example 6-1, (1) to (5) or (6) except for using methoxymethyl chloride in place of methyl iodide in the step of Reference Example 6-1, (1).

Reference Example 6-3

(1) N-tert-Butoxycarbonyl-4-carboxyl-4-methoxymethylpiperidine was obtained by using N-tert-butoxycarbonyl-4-ethoxycarbonylpiperidine (synthesized according to a method described in a literature of Gilligan et al. (J. Med. Chem., Vol. 37, pp. 364-370, 1994)) and methoxymethyl chloride in the same manner as in Reference Example 6-1 (1), followed by the same manner as in Reference Example 6-1 (2).

N-tert-butoxycarbonyl-4-benzyloxycarbonylamino-4-methoxymethylpiperidine was obtained in the same manner as in Reference Example 6-1 (3) except for using this compound and further using benzyl alcohol in place of potassium tert-butoxide.

(2) A mixture comprising 9.4 g of the compound obtained in the above (1). 1.9 g of 10% palladium-carbon, and 190 mL of methanol was stirred under hydrogen atmosphere (1 atm) for 2 hours. 10% palladium-carbon was removed by filtration and the filtrate was concentrated to obtain 6.02 g of 4-amino-N-tert-butoxycarbonyl-4-methoxymethylpiperidine.

Subsequently, this compound was treated with an acid to remove a protective group (tert-butoxycarbonyl group) to obtain 4-amino-4-methoxymethylpiperidine.

Reference Example 6-4

A mixture comprising 3.78 g of N-tert-butoxycarbonyl-4-benzyloxycarbonylamino-4-methoxymethylpiperidine (a compound obtained in Reference Example 6-3 (1)) and 38 ml of concentrated hydrochloric acid was refluxed for 3 days. The reaction mixture was concentrated and the residue was washed with tetrahydrofuran to obtain 2.8 g of 4-amino-4-hydroxymethylpiperidine.dihydrochloride.

Reference Examples 7-1 to 7-7

(1) 16.7 ml of triethylamine was added to 200 ml of a tetrahydrofuran solution containing 16 g of 4-amino-1-tert-butoxycarbonylpiperidine and 17.5 g of N-carboethoxyphthalimide under ice-cooling, and the mixture was stirred at room temperature for 4 hours. Water was added to the reaction mixture and the resulting mixture was extracted with ethyl acetate. The extract was washed with an aqueous saturated sodium bicarbonate solution, water and brine, dried over anhydrous sodium sulfate, and the solvent was removed under reduced pressure. The residue was suspended in ether-hexane, and crystals were collected by filtration to obtain 25.7 g of 2-(1-tert-butoxycarbonyl-4-piperidyl)-isoindoline-1,3-dione.

A 170 ml of 15% hydrochloric acid-ethanol suspension containing 25.5 g of this compound was stirred at room temperature for 5 hours. Precipitates were collected by filtration to obtain 16.0 g of 2-(4-piperidyl)isoindolin-1,3-dione.hydrochloride.

(2) 3.13 ml of triethylamine was added to 15 ml of tetrahydrofuran-3 ml of N,N-dimethylacetamide solution-containing 1.57 g of the compound obtained in the above (1) and 644 mg of 2-chloropyrimidine, and the mixture was stirred at 50° C. for 12 hours. After cooling, an aqueous saturated sodium bicarbonate solution was added to the mixture, and the resulting mixture was extracted with ethyl acetate. The extract was washed with water and brine, dried over anhydrous sodium sulfate, and the solvent was removed under reduced pressure. The residue was suspended in ether-hexane, and crystals were collected by filtration to obtain 1.50 g of 2-[1-(2-pyrimidinyl)-4-piperidyl]isoindolin-1,3-dione. (yield: 87%)

Subsequently, 0.25 ml of hydrazine monohydrate was added to 15 ml of an ethanol suspension containing 800 mg of this compound and the mixture was refluxed for 2 hours. After cooling, insoluble products were removed by filtration and the solvent was removed under reduced pressure. The residue was purified by NH silica gel flash column chromatography (solvent: chloroform-methanol (500:1)) to obtain 417 mg of 4-amino-1-(2-pyrimidinyl)piperidine (Reference Example 7-1 in Table 9).

Also, compounds of Reference Examples 7-2 to 7-7 in Table 9 were obtained in the same manner as mentioned above by using the corresponding starting materials.

Reference Examples 8-1 to 8-7

2 ml of an ethanol suspension containing 260 mg of 4-amino-4-methylpiperidine (synthesized according to a method described in U.S. Pat. No. 5,821,240), 237 mg of 2-chloropyrimidine and 858 mg of potassium carbonate was stirred at 50° C. for 12 hours. The reaction mixture was poured into water, and extracted with chloroform. The extract was washed with brine, dried over anhydrous sodium sulfate, and the solvent was removed under reduced pressure. The residue was purified by silica gel flash column chromatography [solvent: chloroform-methanol-aqueous ammonia (300': 10:1)] to obtain 259 mg of 4-amino-4-methyl-N-(2-pyrimidinyl)piperidine (Reference Example 8-1 in Table 9).

Also, compounds of Reference Examples 8-2 to 8-7 in Table 9 were obtained in the same manner as mentioned above by using the corresponding starting materials.

Reference Examples 8-8 to 8-21

Compounds of Reference Examples 8-8 to 8-15 in Table 9 were obtained in the same manner as mentioned above-mentioned Reference Example 8-1, using 4-amino-4'-methoxymethylpiperidine (Reference Example 6-3 (2)) and corresponding starting materials.

Also, compounds of Reference Examples 8-16 to 8-21 in Table 9 were obtained in the same manner as mentioned above by using 4-amino-4-hydroxymethylpiperidine.dihydrochloride (Reference Example 6-4) and corresponding starting materials.

Reference Examples 8-22 to 8-23

0.86 ml of triethylamine was added to 15 ml of a tetrahydrofuran suspension containing 1.00 g of t-4-tert-butoxycarbonylamino-4-hydroxymethyl-r-1-cyclohexylamine (Reference Example 6-2) and 897 mg of N-carboethoxyphthalimide, and the mixture was heated at 50° C. for 5 hours. Water was added to the reaction mixture, and the mixture was extracted with ethyl acetate. The organic layer was washed with an aqueous saturated sodium hydrogencarbonate solution and brine, and dried over anhydrous sodium sulfate. The solvent was removed under reduced pressure to obtain 1.47 g of N-tert-butoxycarbonyl-1-hydroxymethyl-t-4-phthalimide-r-1-cyclohexylamine. To a solution of 1.44 g of this compound in 10 ml of dioxane was added 10 ml of 4N hydrochloric acid/dioxane, and the mixture was stirred at room temperature for 3 hours. The reaction mixture was diluted with diethyl ether and crystals were collected by filtration. The obtained crystals were washed with diethyl ether to obtain 1.03 g of 1-hydroxymethyl-t-4-phthalimide-r-1-cyclohexylamine (Reference Example 8-22 in Table 9).

Also, a compound of Reference Example 8-23 in Table 9 was obtained in the same manner as mentioned above.

Reference Example 8-24

(1) 15 ml of toluene-1.5 ml of chloroform solution containing 500 mg of N-tert-butoxycarbonyl-trans-1,4-cyclohexanediamine, 623 mg of ethyl 2-bromomethyl benzoate and 354 mg of triethylamine was heated at 100° C. for 5 hours. After cooling, water was added to the mixture and the resulting mixture was extracted with ethyl acetate. The organic layer was washed with brine, dried over anhydrous sodium sulfate, and the solvent was removed under reduced pressure. The residue was purified by silica gel flash column chromatography to obtain 400 mg of N-tert-butoxycarbonyl-trans-4-(1-oxo-2-isoindolinyl)cyclohexylamine.

(2) 10 ml of 4N HCl/dioxane was added to 10 ml of a dioxane solution containing 380 mg of the compound obtained in the above (1), and the mixture was stirred at room temperature for 5 hours. After the reaction mixture was concentrated, the residue was triturated with diethyl ether to obtain 298 mg of trans-4-(1-oxo-2-isoindolinyl)cyclohexylamine hydrochloride (Reference Example 8-24 in Table 9).

Reference Examples 8-25 to 8-31

15 ml of a chloroform solution containing 500 mg of N-tert-butoxycarbonyl-trans-1,4-cyclohexanediamine and 540 mg of 3-nitrophthalic anhydride was refluxed for 1 hour. After cooling, 756 mg of carbonyldiimidazole was added to the mixture and the resulting mixture was stirred at room temperature for 15 hours. Water was added to the reaction mixture and the resulting mixture was extracted with chloroform. The organic layer was washed with brine, dried over anhydrous sodium sulfate, and the solvent was removed under reduced pressure. The residue was purified by silica gel flash column chromatography to obtain 900 mg of N-tert-butoxycarbonyl-trans-4-(1,3-dioxo-4-nitro-2-isoindolinyl)-cyclohexylamine.

10 ml of 4N HCl/dioxane solution was added to 10 ml of a dioxane suspension containing 885 mg of this compound, and the mixture was stirred at room temperature for 5 hours. After the reaction mixture was concentrated, the residue was triturated with diethyl ether to obtain 700 mg of trans-4-(1,3-dioxo-4-nitro-2-isoindolinyl)cyclohexylamine-hydrochloride (Reference Example 8-25 in Table 9).

Also, compounds of Reference Examples 8-26 to 8-31 in Table 9 were obtained in the same manner by using the corresponding starting materials.

Reference Example 8-32

1.49 ml of triethylamine was added to 20 ml of a methylene chloride solution containing 1.5 g of trimellitic anhydride chloride and 0.303 ml of methanol under ice-cooling, and the mixture was stirred at room temperature for 3-hours. Water was added to the reaction mixture and the resulting mixture was extracted with chloroform. The organic layer was dried over anhydrous sodium sulfate and the solvent was removed under reduced pressure to obtain 1.81 g of 4-methoxycarbonylphthalic anhydride. Using this compound as a starting material in place of 3-nitrophthalic anhydride, trans-4-(1,3-dioxo-5-methoxycarbonyl-2-isoindolinyl)cyclohexylamine hydrochloride (Reference Example 8-32 in Table 9) was obtained in the same manner as in Reference Example 8-25.

Reference Examples 8-33 and 8-34

To 10 ml of a methylene chloride solution containing 1.0 g of trimellitic anhydride chloride were added 354 mg of pyrrolidine and 577 mg of triethylamine under ice-cooling, and the mixture was stirred at room temperature for 2 hours. Water was added to the reaction mixture and the resulting mixture was extracted with chloroform. The organic layer was dried over anhydrous sodium sulfate and the solvent was removed under reduced pressure to obtain 1.09 g of 4-(1-pyrrolidinyl)carbonylphthalic anhydride. Using this compound as a starting material in place of 3-nitrophthalic anhydride, trans-4-[1,3-dioxo-5-(1-pyrrolidinyl)carbonyl-2-isoindolinyl]cyclohexylamine hydrochloride (Reference Example 8-33 in Table 9) was obtained in the same manner as in Reference Example 8-25.

Also, a compound of Reference Example 8-34 in Table 9 was obtained in the same manner as described above.

Reference Example 8-35

(1) 5.92 ml of thionyl chloride was added to 150 ml of a methylene chloride suspension containing 15.00 g of trans-(4-benzyloxycarbonylamino)cyclohexan-1-carboxylic acid, and the mixture was refluxed for 4 hours. The reaction mixture was concentrated under reduced pressure, and by repeating an operation of adding methylene chloride and concentrating the mixture under reduced pressure for 2 times, trans-4-(benzyloxycarbonylamino)cyclohexanecarboxylic acid chloride was obtained.

(2) The compound obtained in the above (1) was dissolved in 70 ml of methylene chloride to make a solution, and added dropwise thereto was an aqueous solution comprising 60 ml of conc. aqueous ammonia-120 ml of water under ice-cooling. The mixture was stirred at room temperature for 30 minutes, and the resulting precipitates were collected by filtration. The precipitates were washed with water, 2-propanol, and isopropyl ether to obtain 14.17 g of trans-4-(benzyloxycarbonylamino)-1-cyclohexanecarboxamide.

(3) 5.54 ml of thionyl chloride was added to 140 ml of an acetonitrile suspension containing 7.00 g of the compound obtained in the above (2), and the mixture was refluxed for 30 minutes. The reaction mixture was concentrated under reduced pressure, and after addition of acetonitrile, it was further concentrated under reduced pressure. Diisopropyl ether was added to the obtained residual solid, and the solid was collected by filtration to obtain 6.14 g of trans-4-(benzyloxycarbonylamino)-1-cyclohexanecarbonitrile.

(4) Hydrogen chloride gas was fed into 24 ml of an ethanol suspension containing 1.20 g of the compound obtained in the above (3) under ice-salt cooling until the starting material was once dissolved, and then, precipitates came out again. This reaction mixture was stirred at room temperature for 14 hours, and concentrated under reduced pressure. To the obtained residue was added an aqueous saturated sodium hydrogencarbonate solution, and then, the mixture was extracted with chloroform twice. The extract was dried over anhydrous sodium sulfate, and concentrated under reduced pressure to obtain 0.93 g of ethyl trans-4-(benzyloxycarbonylamino)cyclohexane-1-imidinate.

(5) 163 mg of ammonium chloride was added to a solution of 6 ml of ethanol-1 ml of water containing 929 mg of the compound obtained in the above (4) and the mixture was stirred at room temperature for 9 hours. The reaction mixture was concentrated under reduced pressure, and an operation of adding toluene and concentrating the mixture under reduced pressure was repeated two times. To the obtained residual solid was added 0.3 ml of ethanol-20 ml of ether, and the solid was collected by filtration to obtain 859 mg of trans-4-(benzyloxycarbonylamino)-1-cyclohexanecarboxamidine.hydrochloride.

(6) Using the compound obtained in the above (5) (500 mg) as a starting material, by reacting the same with ethoxyethylene malononitrile according to the method of Schmidt. et al.

(Schmidt. H. W. et al., J. Hetrocycl Chem., Vol. 24, p. 1305, 1987), trans-1-(benzyloxycarbonylamino)-4-(4-amino-5-cyanopyrimidin-2-yl)cyclohexane (186 mg) was obtained.

(7) 282 µl of trimethylsilyl iodide was added to a suspension of 174 mg of the compound obtained in the above (6) in 7 ml of an acetonitrile under ice-cooling, and the mixture was stirred at room temperature for 1 hour. Ice-cold water was added to the reaction mixture and the mixture was washed with chloroform. Subsequently, potassium carbonate was added to the aqueous layer to saturate the mixture, and it was extracted with chloroform 3 times. The extracts were dried over anhydrous sodium sulfate and concentrated under reduced pressure to obtain 105 mg of trans-4-(4-amino-5-cyanopyrimidin-2-yl)cyclohexylamine (Reference Example 8-35 in Table 9).

Reference Example 8-36

Using trans-4-(benzyloxycarbonylamino)-1-cyclohexanecarboxamidine.hydrochloride (a compound of Reference Example 8-35 (5)) (348 mg) as a starting material, by reacting the same with acetylacetone according to the method of Libman et al. (J. Chem. Soc., p. 2305, 1952), trans-1-benzyloxycarbonylamino-4-(4,6-dimethylpyrimidin-2-yl)cyclohexane (220 mg) was obtained. By treating this compound (205 mg) with trimethylsilyl iodide in the same manner as in Reference Example 8-35 (7), trans-4-(4,6-dimethylpyrimidin-2-yl)cyclohexylamine (Reference Example 8-36 in Table 9) (129 mg) was obtained.

Reference Examples 8-37 to 8-39

A mixture comprising-500 mg of N-tert-butoxycarbonyl-trans-1,4-cyclohexanediamine, 326 mg of 1,4-dichlorobutane, 805 mg of potassium carbonate, 70 mg of sodium iodide and ethanol-water (8 ml-2 ml) was stirred at 90° C. for 12 days. Water was added to the reaction mixture, and the resulting mixture was extracted with chloroform. The extract was washed with brine, dried over anhydrous sodium sulfate, and then, the solvent was removed under reduced pressure. The obtained residue was purified by silica gel flash column chromatography (solvent: chloroform-methanol-aqueous ammonia=100/5/0.5 to 100/10/0.5) to obtain 453 mg of N-tert-butoxycarbonyl trans-4-(1-pyrrolidinyl)cyclohexylamine.

This compound was subjected to a deprotecting treatment under acidic conditions to obtain trans-4-(1-pyrrolidinyl)cyclohexylamine (Reference Example 8-37 in Table 9).

Also, compounds of Reference Examples 8-38 to 8-39 in Table 9 were obtained in the same manner as mentioned above.

Reference Example 8-40

A mixture comprising 10 g of trans-4-(tert-butoxycarbonylamino)cyclohexanecarboxylic acid, 7.93 g of 2-chloro-3-aminopyridine, 10.2 g of 1-(3-dimethylaminopropyl)-3-ethylcarbodiimide hydrochloride, 6.5 g of 4-dimethylaminopyridine, and 180 mL of N,N-dimethylformamide was stirred at room temperature for 15 hours. To the reaction mixture was added an aqueous sodium hydrogencarbonate solution to make the solution alkaline, and extracted with ethyl acetate. The extract was washed with water and brine, dried over anhydrous sodium sulfate, and the solvent was removed under reduced pressure to obtain trans-4-tert-butoxycarbonylamino-N-(2-chloro-3-pyridyl)-cyclohexanecarboxamide.

Reference Example 8-41

A mixture comprising 500 mg of trans-4-tert-butoxycarbonylamino-N-(2-chloro-3-pyridyl)cyclohexanecarboxamide (Reference Example 8-40), 858 mg of 2,4-bis-(4-methoxy-phenyl)-1,3-dithio-2,4-diphosphetane-2,4-disulfide and 10 mL of tetrahydrofuran was stirred at 60° C. for 18 hours. Insoluble materials were removed by filtration and the filtrate was concentrated under reduced pressure. The obtained residue was purified by silica gel flash column chromatography (solvent: chloroform-methanol 50:1).

The obtained crude crystals were suspended in 5 mL of ethanol and 10 mL of 4N-hydrochloric acid-ethanol solution was added to the suspension, and the mixture was refluxed for 1.5 hours. Ethanol was removed under reduced pressure and the resulting residue was dissolved in water and washed with ether. Potassium carbonate was added to the aqueous layer to make the solution alkaline, and the solution was extracted with chloroform. The extract was washed with water and brine, dried over anhydrous sodium sulfate, and the solvent was removed under reduced pressure to obtain 195 mg of trans-4-(thiazolo[5,4-b]pyridin-2-yl)cyclohexylamine (Reference Example 8-41 in Table 9).

Reference Example 8-42

By treating trans-4-(benzyloxycarbonylamino)cyclohexanecarboxylic acid and 2-aminophenol in the same manner as in Reference Example 8-40, trans-4-benzyloxycarbonylamino-N-(2-hydroxyphenyl)cyclohexanecarboxamide was obtained.

A mixture comprising 300 mg of this compound, 286 mg of pyridinium-p-toluenesulfonate, 6 ml of methanol, and 6 mL of 1,2-dichloromethane was refluxed for 48 hours. To the reaction mixture was added water and ethyl acetate, and the organic layer was separated. The extract was washed with brine, dried over anhydrous sodium sulfate, and the solvent was removed under reduced pressure. The residue was purified by silica gel flash column chromatography (solvent: chloroform).

A mixture comprising 150 mg of this compound, 30 mg of 10% palladium-carbon and 7.5 mL of methanol was stirred under hydrogen atmosphere (at 1 atm) at room temperature for 2 hours. The catalyst was removed by filtration and the filtrate was concentrated to obtain 63 mg of trans-4-(benzo[d][1,3]oxazol-2-yl)cyclohexylamine (Reference Example 8-42 in Table 9).

Reference Example 8-43

(1) In 35 ml of tetrahydrofuran was suspended 0.74 g of sodium boron hydride, and boron trifluoride diethyl complex was added to the suspension under ice-cooling. The mixture was stirred as such under ice-cooling for 30 minutes, and 90 ml of a tetrahydrofuran solution containing 3.60 g of trans-4-(benzyloxycarbonylamino)cyclohexanecarboxylic acid was added thereto under ice-cooling. After the mixture was stirred at room temperature for 2 hours, the reaction mixture was poured into an ice water and extracted with chloroform. The extract was washed with water and brine, dried over anhydrous sodium sulfate, and the solvent was removed under reduced pressure. The residue was suspended in diisopropyl ether and collected by filtration to obtain N-benzyloxycarbonyl-trans-4-(hydroxymethyl)cyclohexylamine.

(2) 0.81 ml of oxalyl chloride was added to 35 ml of a dichloromethane solution containing 1.95 g of the compound obtained in the above (1) and 1.45 g of dimethylsulfoxide at −78° C. The mixture was stirred at −45° C. for 2 hours, and then, it was cooled down to −78° C. To the mixture was added 5 ml of a dichloromethane solution containing 5.62 g of triethylamine, and after elevating the temperature to room temperature, the mixture was stirred for 2 hours. The reaction mixture was washed with water, hydrochloric acid solution and brine, dried over anhydrous sodium sulfate, and the solvent was removed under reduced pressure. The residue was purified by silica gel chromatography (solvent: hexane-ethyl acetate=4:1) to obtain trans-4'-(benzyloxycarbonylamino) cyclohexanecarbaldehyde.

(3) To a solution of 512 μL of thionyl chloride in 4 mL of dichloromethane was added dropwise a solution of 568 μL of pyridine in 4 mL of dichloromethane, under ice-cooling. Subsequently, 1.53 g of the compound obtained in the above (2) was added thereto. The reaction mixture was stirred at room temperature for 1 hour, and added thereto were 715 mg of 2-aminobenzylamine, followed by a solution of 15 mL of water containing 961 mg of sodium acetate. After the reaction mixture was stirred at room temperature for 1 hour, dichloromethane was removed under reduced pressure. To the residual mixture was added an aqueous 10%-sodium hydroxide solution to make the mixture alkaline, and it was stirred at room temperature for 30 minutes, and then, extracted with chloroform. The extract was washed with water and brine, dried over anhydrous sodium sulfate, and the solvent was removed under reduced pressure. A mixture comprising the obtained residue, 2.66 g of 2,3-dichloro-5,6-dicyano-1,4-benzoquinone and 75 mL of toluene was stirred at room temperature for 14 hours. The reaction mixture was diluted with chloroform and successively washed with an aqueous 10%-sodium hydroxides solution, water and brine, dried over anhydrous sodium sulfate, and the solvent was removed under reduced pressure. The residue was purified by silica gel flash column chromatography (solvent: chloroform). The obtained residue was further suspended in a mixed solvent of isopropyl ether-hexane, and the resulting precipitates were collected by filtration.

In 7 mL of acetonitrile was dissolved 362 mg of this compound. Under ice-cooling, 427 μL of trimethylsilyl iodide was added dropwise thereto, and the mixture was stirred at room temperature for 15 minutes. To the reaction mixture were added methanol and water, and it was washed with chloroform. To the aqueous layer was added potassium carbonate to make the solution alkaline, and it was extracted with chloroform. The extract was washed with water and brine, dried over anhydrous sodium sulfate, and the solvent was removed under reduced pressure to obtain 220 mg of trans-4-(quinazolin-2-yl)cyclohexylamine (Reference Example 8-43 in Table 9).

Reference Example 8-44

Trans-4-(benzyloxycarbonylamino)cyclohexanecarboxylic acid and 3-(aminomethylcarbonyl)pyridine were treated in the same manner as mentioned above Reference Example 8-40 to obtain trans-4-benzyloxycarbonylamino-N-(3-pyridylcarbonylmethyl)cyclohexanecarboxamide.

A mixture comprising 600 mg of this compound, 283 μL of phosphorous oxychloride and 9 mL of N,N-dimethylformamide was stirred at room temperature for 1 hour. The reaction mixture was poured into water, and after the mixture was made alkaline by adding an aqueous sodium bicarbonate solution, it was extracted with ethyl acetate. The extract was washed with water and brine, dried over anhydrous sodium sulfate, and the solvent was removed under reduced pressure. The residue was suspended in diethyl ether, and the resulting precipitates were collected by filtration.

A mixture comprising 350 mg of this compound, 70 mg of 10% palladium-carbon and 17.5 mL of methanol was stirred under hydrogen atmosphere (1 atm) at room temperature for 20 hours. The catalyst was removed by filtration and the filtrate was concentrated to obtain 211 mg of trans-4-[5-(3-pyridyl)-1,3-oxazol-2-yl]cyclohexylamine (Reference Example 8-44 in Table 9).

Reference Examples 8-45 to 8-56

4-tert-butoxycarbonylamino-4-methylcyclohexanone (the compound (3) of Reference Example 6-1) and corresponding starting materials (amine compounds) were stirred in the presence of sodium triacetoxyborohydride at room temperature for 16 hours for reaction to proceed. Subsequently, an acid treatment was carried out for removing the protective group (t-butoxycarbonyl group) to obtain compounds of Reference Examples 8-45 to 8-56 in Table 9.

Reference Examples 8-57 to 8-59

418 mg of sodium triacetoxyborohydride was added to a solution of 300 mg of t-4-tert-butoxycarbonylamino-4-methyl-r-1-cyclohexylamine (a compound obtained in the above Reference Example 6-1 (5)) dissolved in a mixed solvent of 2 ml of tetrahydrofuran and 0.5 ml of formalin, and the mixture was stirred at room temperature for 16 hours. An aqueous 10% sodium hydroxide solution was added thereto and the mixture was extracted with chloroform, and dried over anhydrous sodium sulfate. The solvent was removed under reduced pressure and the residue was purified by silica gel column chromatography (solvent: chloroform-methanol-aqueous ammonia (50:1:0.1 to 10:1:0.1).

This compound was stirred in 2 ml of 4N hydrochloric acid-dioxane, and 2 ml of ethanol for 8 hours, and then, the reaction mixture was concentrated. An aqueous 10% sodium hydroxide solution was added thereto. The mixture was extracted with chloroform, dried over anhydrous sodium sulfate, and the solvent was removed under reduced pressure to obtain 55 mg of t-4-dimethylamino-1-methyl-r-1-cyclohexylamine (Reference Example 8-57 in Table 9).

Similarly, compounds of Reference Examples 8-58 to 8-59 in Table 9 were obtained.

Reference Examples 9-1 to 9-3

To 10 ml of a methylene chloride solution containing 1.04 g of triphosgene were added 10 ml of a methylene chloride solution containing 1.59 g of N-ethoxycarbonylpiperazine and 1.4 ml of triethylamine under ice-cooling, and the mixture was stirred as such for 15 minutes.

To the mixture was added 10 ml of a methylene chloride solution containing 1.00 g of 4-tert-butoxycarbonyl-aminopiperidine and 0.77 ml of triethylamine under ice-cooling, and the mixture was stirred overnight at room temperature. The reaction mixture was poured into an ice water and extracted with chloroform. The extract was washed with brine, dried over anhydrous magnesium sulfate and the solvent was removed under reduced pressure. The residue was purified by silica gel flash column chromatography (solvent; ethyl acetate:hexane=4:1) to obtain 0.94 g of 4-tert-butoxycarbonylamino-1-(4-ethoxycarbonyl-1-piperazinyl)carbonylpiperidine.

In 6 ml of methylene chloride was dissolved 0.66 g of this compound, and 2 ml of trifluoroacetic acid was added thereto, and the mixture was stirred at room temperature for 3 hours. The solvent was removed under reduced pressure and the residue was purified by NH silica gel flash column chromatography (solvent; chloroform:methanol=100:1): to obtain 0.42 g of 4-amino-1-(4-ethoxycarbonyl-1-piperazinyl)carbonylpiperidine (Reference Example 9-1 in Table 10).

Also, by using 4-tert-butoxycarbonylaminopiperidine and corresponding starting materials, compounds of Reference Examples 9-2 and 9-3 were obtained in the same manner as mentioned above.

Reference Examples 9-4 and 9-5

(1) N-nitrosomethylurea was added dropwise to a suspension comprising an aqueous potassium hydroxide solution (4 g of KOH/10 ml of water) and 27 ml of ether under ice-cooling. After completion of the dropwise addition, the ether layer of the reaction mixture was separated and potassium hydroxide was added thereto, and the mixture was left in a refrigerator for 3 hours. To an ether solution of this diazomethane was gradually added 2.00 g of trans-4-(benzyloxycarbonylamino) cyclohexane carboxylic acid chloride (a compound obtained in Reference Example 8-35 (1)), and the mixture was stirred at room temperature for 2 hours. The resulting crystals were collected by filtration and washed with ether to obtain 1.63 g of N-benzyloxycarbonyl-trans-4-(diazoacetyl)cyclohexylamine.

(2) To a suspension of 8 ml of dioxane containing 800 mg of the compound obtained in the above (1) were added morpholine and an aqueous solution of silver nitrate (100 mg/1 ml), and the mixture was stirred at room temperature for 1 hour, and then, at 60° C. for 30 minutes. After the reaction mixture was cooled down to room temperature, water was added thereto and the mixture was extracted with ethyl acetate. The extract was successively washed with water and brine, dried over anhydrous sodium sulfate, and the solvent was removed under reduced pressure. The obtained residue was suspended in ether and the resulting precipitates were collected by filtration to obtain 741 mg of N-benzyloxycarbonyl-trans-4-(morpholinocarbonylmethyl)-cyclohexylamine.

A suspension of 4, ml of methanol containing this compound (350 mg) and 70 mg of 10% palladium-carbon was stirred under hydrogen atmosphere at room temperature and at normal pressure for 3 hours. The catalyst was removed by filtration and the filtrate was concentrated to obtain trans-4-(morpholinocarbonylmethyl)cyclohexylamine (Reference Example 9-4 in Table 10).

(3) To 10 ml of a methylene chloride solution containing 1.00 g of the compound obtained in the above (1) was added 10 ml of 1N hydrochloric acid-ether solution, and the mixture was stirred at room temperature for 4 hours. To the reaction mixture was added an aqueous saturated sodium bicarbonate solution and extracted with chloroform. The extract was washed with brine, dried over anhydrous sodium sulfate and concentrated under reduced pressure to obtain N-benzyloxycarbonyl-trans-4-(chloroacetyl)cyclohexylamine.

A mixture comprising this compound (400 mg), 1.12 g of morpholine and 6 ml of methylene chloride was stirred at room temperature overnight. Water was added to the reaction mixture and the resulting mixture was extracted with chloroform. The extract was successively washed with water and brine, dried over anhydrous sodium sulfate and concentrated under reduced pressure. The obtained residue was suspended in ether and resulting precipitates were collected by filtration to obtain 417 mg of N-benzyloxycarbonyl trans-4-(morpholinomethylcarbonyl)cyclohexylamine.

A suspension of 4 ml of methanol containing this compound and 72 mg of 10% palladium-carbon was stirred under hydrogen atmosphere at room temperature and normal pressure for one hour. The catalyst was removed by filtration and the filtrate was concentrated to obtain trans-4-(morpholinomethylcarbonyl)cyclohexylamine (Reference Example 9-5 in Table 10).

Reference Examples 9-6 and 9-7

Ethyl trans-4-aminocyclohexanecarboxylate hydrochloride (Reference Example 9-6) and ethyl cis-4-aminocyclohexanecarboxylate.hydrochloride (Reference Example 9-7) were synthesized according to the method described in a literature (Johnston et al., J. Med. Chem., 1971, Vol. 14, pp. 600-614).

Reference Examples 9-8 to 9-12

To 6 mL of a tetrahydrofuran solution containing 1.0 g of trans-4-(tert-butoxycarbonylamino)cyclohexanol and 873 mg of benzylbromide was gradually added 204 mg of 60% sodium hydride, 0.5 mL of dimethyl sulfoxide was then further added thereto, and the mixture was stirred at 70° C. for 2 hours. The reaction mixture was poured into water and extracted with chloroform. The extract was washed with water and brine, dried over anhydrous sodium-sulfate, and the solvent was removed under reduced pressure. The residue was applied to silica gel column chromatography (solvent: hexane-ethyl acetate (4:1)), and the obtained powdery crystals were suspended in an ethyl acetate-hexane mixed solvent, and collected by filtration to obtain trans-1-tert-butoxycarbonylamino-4-(benzyloxy)cyclohexane.

To a suspension of this compound in ethanol was added 2N hydrochloric acid-dioxane solution, and the mixture was stirred at room temperature for 18 hours to effect deprotection to obtain trans-4-(benzyloxy)cyclohexylamine hydrochloride (Reference Example 9-8).

Also, by using corresponding starting materials, compounds of Reference Examples 9-9 to 9-12 in Table 10 were obtained in the same manner as mentioned above.

Reference Example 9-13

In 10 ml of methanol was dissolved 204 mg of N-tert-butoxycarbonyl-trans-4-(2-propen-1-yloxy)cyclohexylamine (the compound of Reference Example 9-11). 44 mg of 10% palladium-carbon was added thereto, and the mixture was stirred under hydrogen atmosphere at normal pressure, at room temperature, for 2 days. The catalyst was removed by filtration and the solvent was removed and the residue was stirred in 2 ml of trifluoroacetic acid for 3 hours. The solvent was removed, and the residue was mixed with an aqueous 10% sodium hydroxide solution, extracted with chloroform and dried over anhydrous sodium sulfate. The solvent was removed under reduced pressure to obtain 102 mg of trans-4-(propoxy)cyclohexylamine (Reference Example 9-13 in Table 10).

Reference Examples 9-14 to 9-29

(1) 9.33 g of sodium boron hydride was suspended in 200 ml of tetrahydrofuran, and added thereto was boron trifluoride diethyl complex under ice-cooling. The mixture was stirred as such under ice-cooling for 30 minutes, and then, 150 ml of a tetrahydrofuran solution containing 40 g of trans-4-(tert-butoxycarbonylamino)cyclohexane carboxylic acid was added thereto under ice-cooling. The mixture was stirred at room temperature for 4 hours, and the reaction mixture was poured into ice water, and extracted with chloroform. The extract was washed with water and brine, dried over anhydrous sodium sulfate, and the solvent was removed under reduced pressure. The residue was recrystallized from ethyl acetate-hexane to obtain 20 g of N-tert-butoxycarbonyl-trans-4-(hydroxymethyl)cyclohexylamine.

(2) By using the compound obtained in the above (1) and corresponding starting materials, compounds of Reference Examples 9-14 to 9-29 in Table 10 were obtained in the same manner as in Reference Example 9-8.

Reference Examples 9-30 to 9-33

(1) To a methylene chloride suspension containing 5.00 g of trans-4-(tert-butoxycarbonylamino)cyclohexanol were added 4.86 ml of triethylamine and 3.09 g of methanesulfonyl chloride at 0° C., and the mixture was stirred for 10 minutes. Water was added to the reaction mixture and the resulting mixture was extracted with ethyl acetate. The extract was washed with water, an aqueous saturated sodium bicarbonate solution and brine, dried over anhydrous sodium sulfate, and the solvent was removed under reduced pressure. The residue was suspended in an ethyl acetate-isopropyl ether mixed solvent, and collected by filtration to obtain 6.19 g of trans-4-tert-butoxycarbonylaminocyclo-hexylmethane sulfonate.

(2) 0.818 g of 60% sodium hydride was added to 10 ml of a dimethylformamide solution containing 2-mercaptopyridine-5-carbonitrile under ice-cooling and the mixture was stirred at room temperature for 1 hour. Added thereto was 2.00 g of the compound obtained in the above (1), and the mixture was stirred at room temperature overnight, and at 80° C. for 8 hours, and cooled down to room temperature. Water and methyl acetate were added to the reaction mixture and the organic layer was separated. The extract was successively washed with an aqueous sodium hydroxide solution, water and brine, dried over anhydrous sodium sulfate, and the solvent was removed under reduced pressure. The residue was purified by silica gel flash column chromatography (solvent: ethyl acetate-hexane (1:6)) to obtain 0.977 g of cis-1-tert-butoxycarbonylamino-4-(5-cyano-2-pyridylthio)cyclohexane.

0.977 g of this compound was dissolved in chloroform and 4 ml of 4N-hydrochloric acid-dioxane solution was added thereto, and the mixture was stirred at room temperature for 4 hours. To the reaction mixture was added a little amount of methanol to crystallize an objective compound, and the solvent was evaporated to dryness. The residue was suspended in a mixed solvent of methanol:diisopropyl ether, and collected by filtration to obtain 0.787 g of cis-4-(5-cyano-2-pyridylthio)cyclohexylamine (Reference Example 9-30 in Table 10).

Also, by using corresponding starting materials, compounds of Reference Examples 9-31 to 9-33 in Table 10 were obtained in the same manner as mentioned above.

Reference Example 10-1

(1) To a suspension in which 42.8 g of 5-nitroisoindoline had been added to an aqueous potassium carbonate solution (108 g of potassium carbonate, 200 ml of water) was added dropwise 200 ml of an ethyl acetate solution containing 31.2 ml of chloroacetyl chloride at 0° C. over 1 hour. The mixture was further stirred at 0° C. for 45 minutes and precipitates were collected by filtration. The obtained solid was treated with activated carbon in ethyl acetate and recrystallized to obtain 2-chloroacetyl-5-nitroisoindoline.

(2) In 10 ml of N,N-dimethylformamide were stirred 1.21 g of the compound obtained in the above (1), 1.07 g of N-tert-butoxycarbonyl-trans-1,4-cyclohexanediamine and 1.39 g of potassium carbonate at room temperature for 20 hours. The reaction mixture was poured into water and precipitated solids were collected by filtration, washed with water, dried, and purified by silica gel column chromatography (solvent, chloroform-methanol=98:2 to 95:5) to obtain N-tert-butoxycarbonyl-trans-4-[(5-nitro-2-isoindolinyl)-carbonylmethylamino]cyclohexylamine. In 3 ml of trifluoroacetic acid was dissolved 284 mg of this compound and the Solution was stirred at room temperature for 2 hours. The reaction mixture was concentrated under reduced pressure, and the residue was made basic by 10% sodium hydroxide and extracted with chloroform. The extract was dried over anhydrous sodium sulfate and concentrated under reduced pressure to obtain trans-4-[(5-nitro-2-isoindolinyl)carbonylmethylamino]cyclohexylamine (Reference Example 10-1 in Table 11).

Reference Examples 10-2 to 10-13

10 ml of a N,N-dimethylformamide solution containing 1 g of N-tert-butoxycarbonyl-trans-1,4-cyclohexanediamine, 632 mg of 3-pyridinecarboxylic acid, 1.07° g of 1-ethyl-3-(3-dimethylaminopropyl)-carbodiimide and 757 mg of 1-hydroxybenzotriazole was stirred at room temperature for 24 hours. To the reaction mixture was added an aqueous saturated sodium hydrogencarbonate solution and the resulting mixture was extracted with ethyl acetate. The extract was washed with brine, dried over anhydrous sodium sulfate, and the solvent was removed under reduced pressure. The residue was washed with diethyl ether to obtain N-tert-butoxycarbonyl-trans-4-(3-pyridylcarbonylamino)cyclohexylamine. A mixture comprising 1.27 g of this compound and 13 ml of 15% hydrochloric acid-ethanol solution was stirred at 50° C. for 2 hours. After cooling, precipitates were filtered and washed with diethyl ether to obtain 1.12 g of trans-4-(3-pyridylcarbonylamino)cyclohexylamine.dihydrochloride (Reference Example 10-2 in Table 11).

Also, by using corresponding starting materials, compounds of Reference Examples 10-3 and 10-4 in Table 11 were obtained in the same manner.

Also, by using t- or c-4-tert-butoxycarbonylamino-4-methyl-r-1-cyclohexylamine (the compound of Reference Example 6-1 (5) or (6)) and corresponding starting materials, compounds of Reference Examples 10-5 to 10-10 in Table 11 were obtained in the same manner. (Provided that the formed hydrochloride was converted into a free form by treating with an aqueous potassium carbonate solution.)

Also, by using t- or c-4-tert-butoxycarbonylamino-4-hydroxymethyl-r-1-cyclohexylamine (Reference Example 6-2) and corresponding starting materials, compounds of Reference Examples 10-11 to 10-13 in Table 11 were obtained in the same manner.

Reference Examples 10-14 to 10-17

(1) To 160 ml of a methylene chloride solution containing 16.93 g of 4-(tert-butoxycarbonylamino)cyclohexanone and 10.55 ml of N-methylbenzylamine was added 19.08 g of sodium triacetoxyborohydride under ice-cooling, and the mixture was stirred at room temperature for 14 hours. The reaction mixture was diluted with an aqueous sodium hydrogencarbonate solution and extracted with ethyl acetate. The extract was washed with water and brine, dried over anhydrous sodium sulfate and the solvent was removed under reduced pressure. The obtained residue was suspended in hexane and collected by filtration. This mother liquor was concentrated and the residue was purified by NH-silica gel chromatography (solvent: hexane-ethyl acetate (97:3 to 83:17)). The residue was further suspended in hexane and collected by filtration and combined with the filtered product to obtain 13.55 g of N'-benzyl-N-tert-butoxycarbonyl-N'-methyl-trans-1,4-cyclohexanediamine.

A suspension of 13.53 g of this compound and 2.00 g of palladium hydroxide-carbon in methanol was subjected to catalytic hydrogenation under normal pressure and at room temperature over 5 hours. The catalyst was removed by filtration and the filtrate was concentrated under reduced pressure to obtain 9.93 g of N-tert-butoxycarbonyl-N'-methyl-trans-1,4-cyclohexanediamine.

(2) A mixture comprising 500 mg of the compound obtained in the above (1), 326 mg of 2-pyrazinecarboxylic acid, 355 mg of 1-hydroxybenzotriazole, 997 mg of O-benzotriazol-1-yl-N,N,N',N'-tetramethyluroniumhexafluorophosphate, 578 µl of N-methylmorpholine and 11 ml of N,N-dimethylformamide was stirred at room temperature for 14 hours. To the reaction mixture were added water, followed by an aqueous saturated sodium hydrogencarbonate solution, and the resulting mixture was extracted with ethyl acetate. The extract was washed with an aqueous saturated sodium hydrogencarbonate solution, water and brine, dried over anhydrous sodium sulfate, and the solvent was removed under reduced pressure.

The obtained residue was suspended in diisopropyl ether, and collected by filtration to obtain N-tert-butoxycarbonyl-N'-methyl-N'-(2-pyrazinylcarbonyl)-trans-1,4-cyclohexanediamine.

Subsequently, 420 mg of this compound was dissolved in 6 ml of dioxane, then, 5 ml of 4N hydrochloric acid-dioxane was added thereto, and the mixture was stirred at room temperature for 15 hours. The reaction mixture was diluted with ether, and the resulting precipitates were collected by filtration, and washed with ether to obtain powder. A solution of the obtained powder dissolved in water was saturated with potassium carbonate, and extracted with chloroform. The extract was dried over anhydrous sodium sulfate and the solvent was removed under reduced pressure to obtain N-methyl-N-(2-pyrazinylcarbonyl)-trans-1,4-cyclohexanediamine (Reference Example 10-14 in Table 11).

Also, by using the compound obtained in the above (1) and corresponding starting materials (carboxylic acid compounds), compounds of Reference Examples 10-15 to 10-17 in Table 11 were obtained in the same manner as mentioned above.

Reference Examples 10-18 to 10-20

254 µl of methanesulfonyl chloride was added to a methylene chloride solution containing 500 mg of N-tert-butoxycarbonyl-N'-methyl-trans-1,4-cyclohexanediamine (Reference Example 10-14 (1)) and 763 µl of triethylamine, and the mixture was stirred at room temperature for 14 hours. To the reaction mixture were added water, followed by an aqueous saturated sodium hydrogencarbonate solution, and the mixture was extracted with ethyl acetate. The extract was washed with an aqueous saturated sodium hydrogencarbonate, water and brine, dried over anhydrous sodium sulfate, and the solvent was removed under reduced pressure. The obtained residue was suspended in diisopropyl ether, and collected by filtration to obtain N-tert-butoxycarbonyl-N'-methyl-N'-methylsulfonyl-trans-1,4-cyclohexanediamine. Subsequently, this compound was treaded with hydrochloric acid to obtain-N-methyl-N-methyl-sulfonyl-trans-1,4-cyclohexanediamine (Reference Example 10-18 in Table 11).

Also, by using corresponding starting materials (chlorides), compounds of Reference Examples 10-19 and 10-20 in Table 11 were obtained in the same manner as mentioned above.

In the following Table 1 to Table 11, chemical structures and physical properties of the compounds of the above Examples and Reference Examples are shown. (In these Tables, "Me" represents methyl group. Also, in the Tables, MS·APCI (m/z) represents values from mass spectrometry (atmospheric pressure chemical ionization mass spectrometry).)

TABLE 1

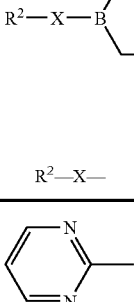

| Example No. | R²—X— | B | R¹ | Salt | Physical properties, etc. |
|---|---|---|---|---|---|
| 1-1 | 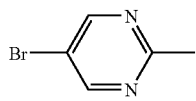 | N | H | 2HCl | Colorless powder MS · APCI (m/z): 315 [M + H]+ |
| 1-2 | Br—(pyrimidine) | N | H | 2HCl | Colorless powder MS · APCI (m/z): 499 [M + H]+ |

TABLE 1-continued

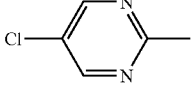

| Example No. | R²—X— | B | R¹ | Salt | Physical properties, etc. |
|---|---|---|---|---|---|
| 1-3 | 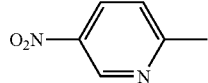 | N | H | 2HCl | Colorless powder MS·APCI (m/z): 349 [M + H]+ |
| 1-4 | 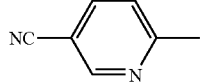 | N | H | 2HCl | Pale yellowish powder MS·APCI (m/z): 359 [M + H]+ |
| 1-5 | 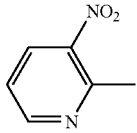 | N | H | 2HCl | Colorless powder MS·APCI (m/z): 339 [M + H]+ |
| 1-6 | 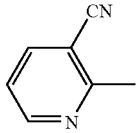 | N | H | 2HCl | Yellowish powder MS·APCI (m/z): 359 [M + H]+ |
| 1-7 | 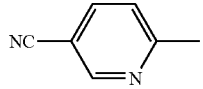 | N | H | 2HCl | Colorless powder MS·APCI (m/z): 339 [M + H]+ |
| 1-8 | 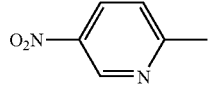 | N | Me | 2HCl | Colorless powder MS·APCI (m/z): 353 [M + H]+ |
| 1-9 | 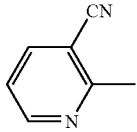 | N | Me | 2HCl | Yellowish powder MS·APCI (m/z): 373 [M + H]+ |
| 1-10 | 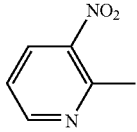 | N | Me | 2HCl | Colorless powder MS·APCI (m/z): 353 [M + H]+ |
| 1-11 | 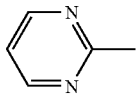 | N | Me | 2HCl | Yellowish powder MS·APCI (m/z): 329 [M + H]+ |
| 1-12 | 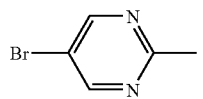 | N | Me | 2HCl | Colorless powder MS·APCI (m/z): 329 [M + H]+ |
| 1-13 | | N | Me | 2HCl | Colorless powder MS·APCI (m/z): 407, 409 [M + H]+ |

TABLE 1-continued

R²—X—B—[cyclohexyl with R¹]—NH—CH₂—C(O)—N(pyrrolidine-2-CN)

| Example No. | R²—X— | B | R¹ | Salt | Physical properties, etc. |
|---|---|---|---|---|---|
| 1-14 | 2-pyrazinyl (methyl-substituted) | N | Me | 2HCl | Yellowish powder<br>MS·APCI (m/z): 329 [M + H]+ |
| 1-15 | 5-nitro-2-methylpyridin-yl (O₂N-pyridine) | N | CH₂OMe | 2HCl | Yellowish powder<br>MS·APCI (m/z): 403 [M + H]+ |
| 1-16 | 5-cyano-2-methylpyridin-yl (NC-pyridine) | N | CH₂OMe | 2HCl | Colorless powder<br>MS·APCI (m/z): 383 [M + H]+ |
| 1-17 | 3-nitropyridin-2-yl (NO₂-pyridine) | N | CH₂OMe | 2HCl | Yellowish powder<br>MS·APCI (m/z): 403 [M + H]+ |
| 1-18 | 3-cyanopyridin-2-yl (CN-pyridine) | N | CH₂OMe | 2HCl | Colorless powder<br>MS·APCI (m/z): 383 [M + H]+ |
| 1-19 | 2-pyrimidinyl | N | CH₂OMe | 2HCl | Colorless powder<br>MS·APCI (m/z): 359 [M + H]+ |
| 1-20 | pyrazinyl | N | CH₂OMe | 2HCl | Yellowish powder<br>MS·APCI (m/z): 359 [M + H]+ |
| 1-21 | 6-chloropyridazin-3-yl (Cl-pyridazine) | N | CH₂OMe | 2HCl | Colorless powder<br>MS·APCI (m/z): 393 [M + H]+ |
| 1-22 | pyridazin-3-yl | N | CH₂OMe | 2HCl | Yellowish powder<br>MS·APCI (m/z): 359 [M + H]+ |
| 1-23 | 5-cyano-2-methylpyridin-yl (NC-pyridine) | N | CH₂OH | 2HCl | Colorless powder<br>MS·APCI (m/z): 369 [M + H]+ |
| 1-24 | 2-pyrimidinyl | N | CH₂OH | 2HCl | Colorless powder<br>MS·APCI (m/z): 345 [M + H]+ |
| 1-25 | pyrazinyl | N | CH₂OH | 2HCl | Yellowish powder<br>MS·APCI (m/z): 345 [M + H]+ |

TABLE 1-continued

| Example No. | R²—X— | B | R¹ | Salt | Physical properties, etc. |
|---|---|---|---|---|---|
| 1-26 | 5-nitro-2-methylpyridin-2-yl (O₂N-pyridine-CH₃) | N | CH₂OH | 2HCl | Yellowish powder MS · APCI (m/z): 389 [M + H]+ |
| 1-27 | 3-cyano-2-methylpyridine | N | CH₂OH | 2HCl | Colorless powder MS · APCI (m/z): 369 [M + H]+ |
| 1-28 | 3-nitro-2-methylpyridine | N | CH₂OH | 2HCl | Yellowish powder MS · APCI (m/z): 389 [M + H]+ |
| 1-29 | phthalimidyl | CH | H | HCl | Colorless powder MS · APCI (m/z): 381 [M + H]+ |
| 1-30 | isoindolin-1-on-2-yl | CH | H | HCl | Colorless powder MS · APCI (m/z): 367 [M + H]+ |
| 1-31 | 4-nitrophthalimidyl | CH | H | HCl | Colorless powder MS · APCI (m/z): 426 [M + H]+ |
| 1-32 | 4-methylphthalimidyl | CH | H | HCl | Colorless powder MS · APCI (m/z): 395 [M + H]+ |
| 1-33 | pyrrolo[3,4-b]pyridine-5,7-dione-6-yl | CH | H | 2HCl | Colorless powder MS · APCI (m/z): 382 [M + H]+ |

TABLE 1-continued

| Example No. | R²—X— | B | R¹ | Salt | Physical properties, etc. |
|---|---|---|---|---|---|
| 1-34 | (2,5-dioxopyrrolidin-1-yl) | CH | H | HCl | Colorless powder<br>MS · APCI (m/z): 333 [M + H]+ |
| 1-35 | 3-(trifluoroacetamido)-2,5-dioxopyrrolidin-1-yl | CH | H | HCl | Colorless powder<br>MS · APCI (m/z): 444 [M + H]+ |
| 1-36 | 3-(benzyloxycarbonylamino)-2,5-dioxopyrrolidin-1-yl | CH | H | HCl | Colorless powder<br>MS · APCI (m/z): 482 [M + H]+ |
| 1-37 | 3-(methoxycarbonylamino)-2,5-dioxopyrrolidin-1-yl | CH | H | HCl | Colorless powder<br>MS · APCI (m/z): 406 [M + H]+ |
| 1-38 | 5-(methoxycarbonyl)-1,3-dioxoisoindolin-2-yl | CH | H | HCl | Colorless powder<br>MS · APCI (m/z): 439 [M + H]+ |
| 1-39 | 5-(pyrrolidin-1-ylcarbonyl)-1,3-dioxoisoindolin-2-yl | CH | H | HCl | Colorless powder<br>MS · APCI (m/z): 478 [M + H]+ |
| 1-40 | 5-(piperidin-1-ylcarbonyl)-1,3-dioxoisoindolin-2-yl | CH | H | HCl | Colorless powder<br>MS · APCI (m/z): 492 [M + H]+ |

TABLE 1-continued

| Example No. | R²—X— | B | R¹ | Salt | Physical properties, etc. |
|---|---|---|---|---|---|
| 1-41 | 4-amino-5-cyanopyrimidin-2-yl | CH | H | 2HCl | Colorless powder MS·APCI (m/z): 354 [M + H]+ |
| 1-42 | 4,6-dimethylpyrimidin-2-yl | CH | H | HCl | Colorless powder MS·APCI (m/z): 342 [M + H]+ |
| 1-43 | pyrrolidin-1-yl | CH | H | 2HCl | Colorless powder MS·APCI (m/z): 305 [M + H] |
| 1-44 | morpholin-4-yl | CH | H | 2HCl | Colorless powder MS·APCI (m/z): 321 [M + H] |
| 1-45 | isoindolin-2-yl | CH | H | 2HCl | Colorless powder MS·APCI (m/z): 353 [M + H] |
| 1-46 | thiazolo[5,4-b]pyridin-2-yl | CH | H | 2HCl | Purified powder MS·APCI (m/z): 370 [M + H]+ |
| 1-47 | benzoxazol-2-yl | CH | H | HCl | Purified powder MS·APCI (m/z): 353 [M + H]+ |
| 1-48 | quinazolin-2-yl | CH | H | 2HCl | Purified powder MS·APCI (m/z): 364 [M + H]+ |
| 1-49 | 5-(pyridin-3-yl)oxazol-2-yl | CH | H | 2HCl | Purified powder MS·APCI (m/z): 380 [M + H]+ |
| 1-50 | phthalimid-2-yl | CH | $CH_2OH$ | HCl | Colorless powder MS·APCI (m/z): 411 [M + H]+ |
| 1-51 | pyrrolidin-1-yl | CH | Me | 2HCl | Colorless powder MS·APCI (m/z): 319 [M + H]+ |

TABLE 1-continued

| Example No. | R²—X— | B | R¹ | Salt | Physical properties, etc. |
|---|---|---|---|---|---|
| 1-52 | NC-CH₂-NH- | CH | Me | 2HCl | Purified powder MS · APCI (m/z): 304 |
| 1-53 | (H₃C—O—CH₂CH₂)₂N- | CH | Me | 2HCl | Purified powder MS · APCI (m/z): 381 |
| 1-54 | (H₃C)₂N- | CH | Me | 2HCl | Purified powder MS · APCI (m/z): 293 |
| 1-55 | (CH₃)₂CH-NH- | CH | Me | 2HCl | Purified powder MS · APCI (m/z): 307 |
| 1-56 | sec-Bu-NH- | CH | Me | 2HCl | Purified powder MS · APCI (m/z): 321 |
| 1-57 | 2-pyridyl-CH₂CH₂-N(CH₃)- | CH | Me | 3HCl | Colorless powder MS · APCI (m/z): 384 [M + H]+ |
| 1-58 | ethoxycarbonyl-piperazinyl-C(O)- | N | H | HCl | Colorless purified powder MS · APCI (m/z): 421 |
| 1-59 | morpholinyl-C(O)- | N | H | HCl | Colorless purified powder MS · APCI (m/z): 350 |
| 1-60 | (H₃C)₂N-C(O)- | CH | H | HCl | Colorless purified powder MS · APCI (m/z): 308 [M + H]+ |
| 1-61 | morpholinyl-C(O)-CH- | CH | H | HCl | Colorless powder MS · APCI (m/z): 363 [M + H] |
| 1-62 | morpholinyl-CH₂-C(O)- | CH | H | 2HCl | Colorless powder MS · APCI (m/z): 363 [M + H] |

TABLE 1-continued

| Example No. | R²—X— | B | R¹ | Salt | Physical properties, etc. |
|---|---|---|---|---|---|
| 1-63 | H₃C-O-C(=O)- (ethyl ester) | CH | H | HCl | Colorless powder<br>MS·APCI (m/z): 308 [M + H]+ |
| 1-64 | H₃C-O-C(=O)- | CH | H | HCl | Colorless powder<br>MS·APCI (m/z): 308 [M + H]+ |
| 1-65 | Ph-CH₂-O- | CH | H | HCl | Colorless powder<br>MS·APCI (m/z): 342 |
| 1-66 | H₃C-O- | CH | H | HCl | Purified powder<br>MS·APCI (m/z): 266 |
| 1-67 | H₃C-CH₂-O- | CH | H | HCl | Purified powder<br>MS·APCI (m/z): 280 |
| 1-68 | H₂C=CH-CH₂-O- | CH | H | HCl | Purified powder<br>MS·APCI (m/z): 292 |
| 1-69 | H₃C-O-CH₂CH₂-O- | CH | H | HCl | Purified powder<br>MS·APCI (m/z): 310 |
| 1-70 | H₃C-CH₂-CH₂-O- | CH | H | HCl | Purified powder<br>MS·APCI (m/z): 294 |
| 1-71 | 3-NO₂-pyridin-2-yl-O- | CH | H | 2HCl | Colorless purified powder<br>MS·APCI (m/z): 388 |
| 1-72 | 5-NO₂-pyridin-2-yl-O- | CH | H | 2HCl | Colorless purified powder<br>MS·APCI (m/z): 388 |
| 1-73 | 3-CN-pyridin-2-yl-O- | CH | H | 2HCl | Colorless purified powder<br>MS·APCI (m/z): 368 |
| 1-74 | 5-CN-pyridin-2-yl-O- | CH | H | 2HCl | Colorless purified powder<br>MS·APCI (m/z): 368 |
| 1-75 | 4-CF₃-pyrimidin-2-yl-O- | CH | H | HCl | Colorless purified powder<br>MS·APCI (m/z): 412 |
| 1-76 | pyrazin-2-yl-O- | CH | H | HCl | Colorless purified powder<br>MS·APCI (m/z): 344 |

TABLE 1-continued

| Example No. | R²—X— | B | R¹ | Salt | Physical properties, etc. |
|---|---|---|---|---|---|
| 1-77 | 3-chloro-pyrazin-2-yl-oxyethyl | CH | H | HCl | Colorless purified powder MS·APCI (m/z): 378 |
| 1-78 | 4-fluoro-2-cyanophenoxyethyl | CH | H | HCl | Colorless purified powder MS·APCI (m/z): 385 |
| 1-79 | 2-cyano-3-methoxyphenoxyethyl | CH | H | HCl | Colorless purified powder MS·APCI (m/z): 397 |
| 1-80 | 3-chloro-2-cyanophenoxyethyl | CH | H | HCl | Colorless purified powder MS·APCI (m/z): 401 |
| 1-81 | 2-cyano-4-methylphenoxyethyl | CH | H | HCl | Colorless purified powder MS·APCI (m/z): 381 |
| 1-82 | 2-cyanophenoxyethyl | CH | H | HCl | Colorless purified powder MS·APCI (m/z): 367 |
| 1-83 | 4-cyanophenoxyethyl | CH | H | HCl | Colorless purified powder MS·APCI (m/z): 367 |
| 1-84 | 2-nitrophenoxyethyl | CH | H | HCl | Colorless purified powder MS·APCI (m/z): 387 |
| 1-85 | 4-nitrophenoxyethyl | CH | H | HCl | Colorless purified powder MS·APCI (m/z): 387 |

TABLE 1-continued

| Example No. | R²—X— | B | R¹ | Salt | Physical properties, etc. |
|---|---|---|---|---|---|
| 1-86 | 5-bromo-pyrimidin-2-yloxy-ethyl | CH | H | HCl | Colorless purified powder<br>MS·APCI (m/z): 423 |
| 1-87 | 5-nitro-pyridin-2-ylthio | CH | H | HCl | Pale yellowish powder<br>MS·APCI (m/z): 390 [M + H]+ |
| 1-88 | 5-trifluoromethyl-pyridin-2-ylthio | CH | H | HCl | Colorless powder<br>MS·APCI (m/z): 413 [M + H]+ |
| 1-89 | 5-cyano-pyridin-2-ylthio | CH | H | HCl | Colorless powder<br>MS·APCI (m/z): 370 [M + H]+ |
| 1-90 | 5-chloro-pyridin-2-ylthio | CH | H | HCl | Colorless powder<br>MS·APCI (m/z): 378 [M + H]+ |
| 1-91 | 2-cyano-pyrrolidinyl-acetyl-amino | CH | H | 2HCl | Purified powder<br>MS·APCI (m/z): 387 [M + H]+ |
| 1-92 | 5-nitro-isoindolin-2-yl-acetyl-amino | CH | H | 2HCl | Colorless powder<br>MS·APCI (m/z): 455 [M + H]+ |
| 1-93 | 2-methoxycarbonyl-nicotinoyl-amino | CH | H | 2HCl | Colorless powder<br>MS·APCI (m/z): 414 [M + H]+ |
| 1-94 | pyridin-2-yl-carbonyl-amino | CH | Me | 2HCl | Colorless powder<br>MS·APCI (m/z): 370 [M + H]+ |
| 1-95 | pyridin-3-yl-carbonyl-amino | CH | Me | 2HCl | Colorless powder<br>MS·APCI (m/z): 370 [M + H]+ |
| 1-96 | pyrazin-2-yl-carbonyl-amino | CH | Me | 2HCl | Colorless powder<br>MS·APCI (m/z): 371 [M + H]+ |

TABLE 1-continued

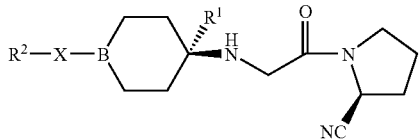

| Example No. | R²—X— | B | R¹ | Salt | Physical properties, etc. |
|---|---|---|---|---|---|
| 1-97 | pyridine-2-C(O)NH- | CH | Me | 2HCl | Colorless powder MS·APCI (m/z): 370 [M + H]+ |
| 1-98 | pyridine-3-C(O)NH- | CH | Me | 2HCl | Colorless powder MS·APCI (m/z): 370 [M + H]+ |
| 1-99 | pyrazine-2-C(O)NH- | CH | Me | 2HCl | Colorless powder MS·APCI (m/z): 371 [M + H]+ |
| 1-100 | pyridine-3-C(O)NH- | CH | CH₂OH | 2HCl | Colorless powder MS·APCI (m/z): 386 [M + H]+ |
| 1-101 | pyrazine-2-C(O)NH- | CH | CH₂OH | HCl | Colorless powder MS·APCI (m/z): 387 [M + H]+ |
| 1-102 | 5-nitrofuran-2-C(O)NH- | CH | CH₂OH | HCl | Colorless powder MS·APCI (m/z): 420 [M + H]+ |
| 1-103 | pyrazine-2-C(O)NH- | CH | H | 2HCl | Purified powder MS·APCI (m/z): 371 [M + H]+ |
| 1-104 | pyridine-2-C(O)NH- | CH | H | 2HCl | Purified powder MS·APCI (m/z): 370 [M + H]+ |
| 1-105 | pyridine-3-C(O)N(CH₃)- | CH | H | 2HCl | Purified powder MS·APCI (m/z): 370 [M + H]+ |
| 1-106 | morpholine-CH₂CH₂C(O)N(CH₃)- | CH | H | 2HCl | Unpurified powder MS·APCI (m/z): 406 [M + H]+ |
| 1-107 | morpholine-C(O)N(CH₃)- | CH | H | HCl | Purified powder MS·APCI (m/z): 378 [M + H]+ |

TABLE 1-continued

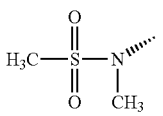

| Example No. | R²—X— | B | R¹ | Salt | Physical properties, etc. |
|---|---|---|---|---|---|
| 1-108 | 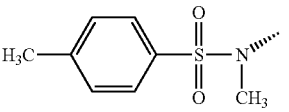 | CH | H | HCl | Purified powder MS · APCI (m/z): 343 [M + H]+ |
| 1-109 | 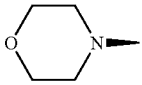 | CH | H | HCl | Purified powder MS · APCI (m/z): 419 [M + H]+ |

TABLE 2

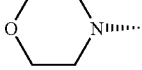

| Example No. | R²—X— | B | R¹ | Salt | Physical properties, etc. |
|---|---|---|---|---|---|
| 2-1 | 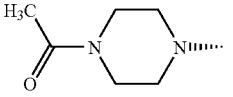 | CH | Me | 2HCl | Purified powder MS•APCI (m/z): 335 |
| 2-2 | 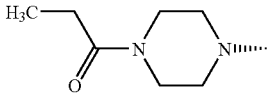 | CH | Me | 2HCl | Purified powder MS•APCI (m/z): 335 |
| 2-3 | 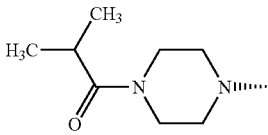 | CH | Me | 2HCl | Purified powder MS•APCI (m/z): 376 |
| 2-4 | 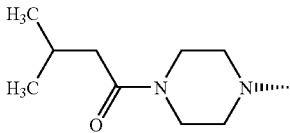 | CH | Me | 2HCl | Purified powder MS•APCI (m/z): 390 |
| 2-5 | | CH | Me | 2HCl | Purified powder MS•APCI (m/z): 404 |
| 2-6 | | CH | Me | 2HCl | Purified powder MS•APCI (m/z): 418 |

TABLE 2-continued

| Example No. | R²—X— | B | R¹ | Salt | Physical properties, etc. |
|---|---|---|---|---|---|
| 2-7 | cyclopropyl-C(O)-piperazinyl | CH | Me | 2HCl | Purified powder MS•APCI (m/z): 402 |
| 2-8 | cyclohexyl-C(O)-piperazinyl | CH | Me | 2HCl | Purified powder MS•APCI (m/z): 444 |
| 2-9 | phenyl-piperazinyl | CH | Me | 2HCl | Purified powder MS•APCI (m/z): 410 |

TABLE 3

| Example No. | R²—X— | B | R¹ | Salt | Physical properties, etc. |
|---|---|---|---|---|---|
| 3 | morpholinyl-C(O)-O— | CH | H | HCl | Colorless crystal Melting point: 213° C.-(decomposed) |

TABLE 4

| Example No. | R²—X— | B | R¹ | Salt | Physical properties, etc. |
|---|---|---|---|---|---|
| 4-1 | benzyl-NH-C(O)-CH₃ | N | H | HCl | Colorless powder MS•APCI (m/z): 370 [M + H]+ |

TABLE 4-continued

| Example No. | R²—X— | B | R¹ | Salt | Physical properties, etc. |
|---|---|---|---|---|---|
| 4-2 | (phenyl-NH-C(=O)-CH₂-) | N | H | HCl | Colorless powder MS·APCI (m/z): 356 [M + H]+ |
| 4-3 | H₃C-(CH₂)₂-NH-C(=O)-CH₂- | N | H | HCl | Colorless powder MS·APCI (m/z): 336 [M + H]+ |
| 4-4 | HOOC-CH₂-C(=O)-CH₂- | N | H | HCl | Colorless powder MS·APCI (m/z): 337 [M + H]+ |
| 4-5 | HOOC-(CH₂)₂-C(=O)-CH₂- | N | H | HCl | Colorless powder MS·APCI (m/z): 351 [M + H]+ |
| 4-6 | CH₃O-C(=O)-CH₂- | N | H | HCl | Colorless powder MS·APCI (m/z): 295 [M + H]+ |
| 4-7 | PhO-C(=O)-CH₂- | N | H | HCl | Colorless powder MS·APCI (m/z): 357 [M + H]+ |
| 4-8 | H₃C-C₆H₄-S(=O)₂-CH₂- | N | H | HCl | Colorless powder MS·APCI (m/z): 391 [M + H]+ |
| 4-9 | H₃C-S(=O)₂-CH₂- | N | H | HCl | Colorless crystal Melting point: 95-98° C. |
| 4-10 | Ph-CH=CH-S(=O)₂-CH₂- | N | H | HCl | Brownish powder MS·APCI (m/z): 403 [M + H]+ |
| 4-11 | quinolin-2-yl-C(=O)-CH₂- | N | H | 2HCl | Colorless powder MS·APCI (m/z): 392 [M + H]+ |
| 4-12 | Ph-C(=O)-CH₂- | N | H | HCl | Colorless powder MS·APCI (m/z): 341 [M + H]+ |

TABLE 4-continued

R²—X—B⟨R¹⟩—NH—CH₂—C(O)—N(pyrrolidine-2-CN)

| Example No. | R²—X— | B | R¹ | Salt | Physical properties, etc. |
|---|---|---|---|---|---|
| 4-13 | 4-Br-C₆H₄-C(O)- | N | H | HCl | Colorless powder MS·APCI (m/z): 419 [M + H]+ |
| 4-14 | 4-(H₂NSO₂)-C₆H₄-C(O)- | N | H | Free form | Colorless crystal Melting point: 135-140° C. MS·APCI (m/z): 420 [M + H]+ |
| 4-15 | 2-pyridyl-C(O)- | N | H | 2HCl | Colorless powder MS·APCI (m/z): 342 [M + H]+ |
| 4-16 | 3-thienyl-C(O)- | N | H | HCl | Colorless powder MS·APCI (m/z): 347 [M + H]+ |
| 4-17 | CH₃O-CH₂-C(O)- | N | H | HCl | Colorless powder MS·APCI (m/z): 309 [M + H]+ |
| 4-18 | CH₃-CH₂-C(O)- | N | H | HCl | Colorless powder MS·APCI (m/z): 307 [M + H]+ |
| 4-19 | morpholino-CH₂-CH₂-C(O)- | N | H | 2HCl | Colorless powder MS·APCI (m/z): 378 [M + H]+ |

TABLE 5

R²—X—B⟨R¹⟩—NH—CH₂—C(O)—N(pyrrolidine-2-CN)

| Example No. | R²—X— | B | R¹ | Salt | Physical properties, etc. |
|---|---|---|---|---|---|
| 5-1 | Ph-NH-C(O)-NH- | CH | H | HCl | Colorless powder MS·APCI (m/z): 370 [M + H]+ |
| 5-2 | 3-NC-C₆H₄-NH-C(O)-NH- | CH | H | HCl | Colorless powder MS·APCI (m/z): 395 [M + H]+ |

TABLE 5-continued

| Example No. | R²—X— | B | R¹ | Salt | Physical properties, etc. |
|---|---|---|---|---|---|
| 5-3 | | CH | H | HCl | Colorless powder MS·APCI (m/z): 350 [M + H]+ |
| 5-4 | | CH | H | HCl | Colorless powder MS·APCI (m/z): (ESI) 351 [M + H] |
| 5-5 | | CH | H | HCl | Brownish powder MS·APCI (m/z): (ESI) 363 [M − H] |
| 5-6 | | CH | H | HCl | Colorless powder MS·APCI (m/z): 309 [M + H]+ |
| 5-7 | | CH | H | HCl | Colorless powder MS·APCI (m/z): 371 [M + H]+ |
| 5-8 | | CH | H | HCl | Colorless powder MS·APCI (m/z): 384 [M + H]+ |
| 5-9 | | CH | H | HCl | Colorless powder MS·APCI (m/z): 322 [M + H]+ |
| 5-10 | | CH | H | HCl | Colorless powder MS·APCI (m/z): 364 [M + H]+ |
| 5-11 | | CH | H | HCl | Brownish powder MS·APCI (m/z): 405 [M + H]+ |
| 5-12 | | CH | H | HCl | Brownish powder MS·APCI (m/z): 329 [M + H]+ |
| 5-13 | | CH | H | 2HCl | Colorless powder MS·APCI (m/z): 356 [M + H]+ |

TABLE 5-continued

[Structure: R²—X—B(cyclohexyl)—N(R¹)H—CH₂—C(=O)—N(pyrrolidinyl with CN)]

| Example No. | R²—X— | B | R¹ | Salt | Physical properties, etc. |
|---|---|---|---|---|---|
| 5-14 | nicotinamide (pyridin-3-yl-C(=O)-NH-) | CH | H | 2HCl | Colorless powder MS·APCI (m/z): 356 [M + H]+ |
| 5-15 | 5-bromo-pyridin-3-yl-C(=O)-NH- | CH | H | 2HCl | Colorless powder MS·APCI (m/z): 434, 436 [M + H]+ |
| 5-16 | 6-chloro-pyridin-3-yl-C(=O)-NH- | CH | H | 2HCl | Colorless powder MS·APCI (m/z): 390 [M + H]+ |
| 5-17 | 6-amino-pyridin-3-yl-C(=O)-NH- | CH | H | 2HCl | Colorless powder MS·APCI (m/z): 371 [M + H]+ |
| 5-18 | pyrazin-2-yl-C(=O)-NH- | CH | H | HCl | Pale yellowish powder MS·APCI (m/z): 357 [M; H]+ |
| 5-19 | quinolin-3-yl-C(=O)-NH- | CH | H | 2HCl | Colorless powder MS·APCI (m/z): 406 [M + H]+ |
| 5-20 | 5-methyl-thiazol-4-yl-C(=O)-NH- | CH | H | HCl | Brownish powder MS·APCI (m/z): 376 [M + H]+ |
| 5-21 | 3-propyl-1-methyl-pyrazol-5-yl-C(=O)-NH- | CH | H | HCl | Colorless powder MS·APCI (m/z): 401 [M + H]+ |
| 5-22 | 5-methyl-isoxazol-3-yl-C(=O)-NH- | CH | H | HCl | Colorless powder MS·APCI (m/z): 360 [M + H]+ |
| 5-23 | 3,4-dimethoxy-phenyl-C(=O)-NH- | CH | H | HCl | Colorless powder MS·APCI (m/z): 415 [M + H]+ |

TABLE 5-continued

| Example No. | R²—X— | B | R¹ | Salt | Physical properties, etc. |
|---|---|---|---|---|---|
| 5-24 | cyclopropyl-C(O)NH— | CH | H | HCl | Colorless powder MS·APCI (m/z): 319 [M + H]+ |
| 5-25 | 1-phenylcyclohexyl-C(O)NH— | CH | H | HCl | Colorless powder MS·APCI (m/z): 437 [M + H]+ |
| 5-26 | (pyridin-2-yl)CH₂C(O)NH— | CH | H | 2HCl | Colorless powder MS·APCI (m/z): 370 [M + H]+ |
| 5-27 | piperidin-1-yl-CH₂C(O)NH— | CH | H | 2HCl | Colorless powder MS·APCI (m/z): 376 [M + H]+ |
| 5-28 | morpholin-4-yl-CH₂CH₂C(O)NH— | CH | H | 2HCl | Colorless powder MS·APCI (m/z): 392 [M + H]+ |
| 5-29 | PhOCH₂C(O)NH— | CH | H | HCl | Colorless powder MS·APCI (m/z): 385 [M + H]+ |
| 5-30 | H₃C−C(O)NH— | CH | H | HCl | Colorless powder MS·APCI (m/z): 293 [M + H]+ |
| 5-31 | (pyridin-2-yl)C(O)NH— | CH | H | 2HCl | Colorless amorphous MS·APCI (m/z): 370 [M + H]+ |
| 5-32 | (pyridin-3-yl)C(O)NH— | CH | H | 2HCl | Colorless amorphous MS·APCI (m/z): 370 [M + H]+ |

TABLE 5-continued

| Example No. | R²—X— | B | R¹ | Salt | Physical properties, etc. |
|---|---|---|---|---|---|
| 5-33 | (2-methylthio-pyridine-3-carboxamide) | CH | H | 2HCl | Colorless amorphous MS•APCI (m/z): 416 [M + H]+ |
| 5-34 | (pyrazine-2-carboxamide) | CH | H | HCl | Colorless amorphous MS•APCI (m/z): 371 [M + H]+ |
| 5-35 | (6-oxo-1,6-dihydropyridazine-3-carboxamide) | CH | H | HCl | Colorless amorphous MS•APCI (m/z): 387 [M + H]+ |
| 5-36 | (pyrimidin-2-yl-acetamide) | CH | H | HCl | Colorless amorphous MS•APCI (m/z): 385 [M + H]+ |
| 5-37 | (5-bromo-pyrimidin-2-ylamino) | CH | H | HCl | Colorless powder MS•APCI (m/z): 421 [M + H]+ |
| 5-38 | (5-nitro-pyridin-2-ylamino) | CH | H | 2HCl | Colorless amorphous MS•APCI (m/z): 387 [M + H]+ |
| 5-39 | (5-cyano-pyridin-2-ylamino) | CH | H | 2HCl | Colorless amorphous MS•APCI (m/z): 367 [M + H]+ |

TABLE 6

| Example No. | R²—X— | B | R¹ | Salt | Physical properties, etc. |
|---|---|---|---|---|---|
| 6-1 | (5-chloro-pyrimidin-2-ylamino) | CH | H | 2HCl | Colorless powder MS•APCI (m/z): 377 [M + H]+ |
| 6-2 | (5-methylthio-pyrimidin-2-ylamino) | CH | H | 2HCl | Colorless powder MS•APCI (m/z): 389 [M + H]+ |

TABLE 6-continued

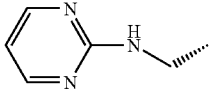

| Example No. | R²—X— | B | R¹ | Salt | Physical properties, etc. |
|---|---|---|---|---|---|
| 6-3 | 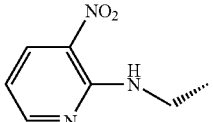 | CH | H | 2HCl | Colorless powder MS•APCI (m/z): 343 [M + H]+ |
| 6-4 | 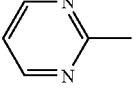 | CH | H | 2HCl | Pale yellowish powder MS•APCI (m/z): 387 [M + H]+ |

TABLE 7

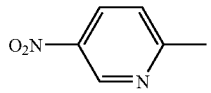

| Example No. | R²—X— | B | R¹ | Salt | Physical properties, etc. |
|---|---|---|---|---|---|
| 7-1 | 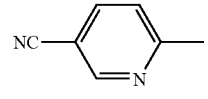 | N | H | 2HCl | Colorless powder MS•APCI (m/z): 333 [M + H]+ |
| 7-2 | 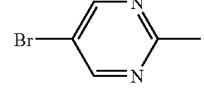 | N | H | 2HCl | Pale yellowish powder MS•APCI (m/z): 377 [M + H]+ |
| 7-3 | 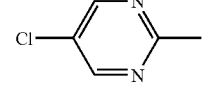 | N | H | 2HCl | Colorless powder MS•APCI (m/z): 357 [M + H]+ |
| 7-4 | 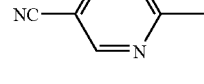 | N | H | 2HCl | Colorless powder MS•APCI (m/z): 411 [M + H]+ |
| 7-5 | 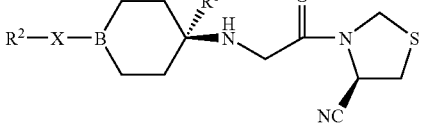 | N | H | 2HCl | Colorless powder MS•APCI (m/z): 367 [M + H]+ |
| 7-6 | 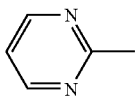 | N | Me | 2HCl | Colorless powder MS•APCI (m/z): 371 [M + H]+ |

TABLE 7-continued

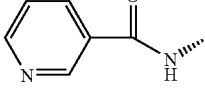

| Example No. | R²—X— | B | R¹ | Salt | Physical properties, etc. |
|---|---|---|---|---|---|
| 7-7 | 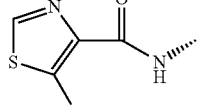 | N | Me | 2HCl | Colorless powder MS•APCI (m/z): 347 [M + H]+ |
| 7-8 | | CH | H | 2HCl | Colorless powder MS•APCI (m/z): 374 [M + H]+ |
| 7-9 | | CH | H | 2HCl | Colorless powder MS•APCI (m/z): 374 [M + H]+ |
| 7-10 | | CH | H | 2HCl | Colorless powder MS•APCI (m/z): 394 [M + H]+ |

TABLE 8

| Example No. | R²—X— | B | R¹ | Salt | Physical properties, etc. |
|---|---|---|---|---|---|
| 8-1 | O₂N-pyridin-2-yl-NH- | CH | H | 2HCl | Pale yellowish powder<br>MS·APCI (m/z): 405 [M + H]+ |
| 8-2 | NC-pyridin-2-yl-NH- | CH | H | 2HCl | Colorless powder<br>MS·APCI (m/z): 385 [M + H]+ |
| 8-3 | Br-pyrimidin-2-yl-NH- | CH | H | 2HCl | Colorless powder<br>MS·APCI (m/z): 439 [M + H]+ |
| 8-4 | Cl-pyrimidin-2-yl-NH- | CH | H | 2HCl | Colorless powder<br>MS·APCI (m/z): 395 [M + H]+ |
| 8-5 | H₃C-S-pyrimidin-2-yl-NH- | CH | H | Free form | Colorless powder<br>MS·APCI (m/z): 407 [M + H]+ |
| 8-6 | pyrimidin-2-yl-NH- | CH | H | 2HCl | Colorless powder<br>MS·APCI (m/z): 361 [M + H]+ |
| 8-7 | pyridin-2-yl-C(O)NH- | CH | H | 2HCl | Colorless powder<br>MS·APCI (m/z): 388 [M + H]+ |
| 8-8 | pyridin-3-yl-C(O)NH- | CH | H | 2HCl | Colorless powder<br>MS·APCI (m/z): 388 [M + H]+ |

TABLE 9

| Reference Example No. | R²—X— | B | R¹ | Salt | Physical properties, etc. |
|---|---|---|---|---|---|
| 7-1 | pyrimidin-2-yl- | N | H | Free form | Colorless crystal<br>Melting point: 76-79° C. |
| 7-2 | O₂N-pyridin-2-yl- | N | H | 2HCl | Colorless crystal<br>Melting point: 251-256° C. |

TABLE 9-continued

R²—X—B—[cyclohexyl(R¹)]—NH₂

| Reference Example No. | R²—X— | B | R¹ | Salt | Physical properties, etc. |
|---|---|---|---|---|---|
| 7-3 | NC-(6-methylpyridin-3-yl) | N | H | Free form | Colorless crystal Melting point: 68-71° C. |
| 7-4 | Br-(2-methylpyrimidin-5-yl) | N | H | Free form | Colorless crystal Melting point: 113-115° C. |
| 7-5 | Cl-(2-methylpyrimidin-5-yl) | N | H | Free form | Colorless crystal Melting point: 54-56° C. |
| 7-6 | (3-nitro-2-methylpyridin-6-yl) | N | H | Free form | Yellowish oil MS·APCI (m/z): 223 [M + H]+ |
| 7-7 | (3-cyano-2-methylpyridin-6-yl) | N | H | Free form | Colorless oil MS·APCI (m/z): 203 [M + H]+ |
| 8-1 | (2-methylpyrimidin-?-yl) | N | Me | Free form | Colorless liquid MS·APCI (m/z): 193 [M + H]+ |
| 8-2 | NC-(6-methylpyridin-3-yl) | N | Me | Free form | Colorless powder MS·APCI (m/z): 217 [M + H]+ |
| 8-3 | O₂N-(6-methylpyridin-3-yl) | N | Me | Free form | Yellowish powder MS·APCI (m/z): 237 [M + H]+ |
| 8-4 | (3-cyano-2-methylpyridin-6-yl) | N | Me | Free form | Colorless liquid MS·APCI (m/z): 217 [M + H]+ |
| 8-5 | (3-nitro-2-methylpyridin-6-yl) | N | Me | Free form | Yellowish powder MS·APCI (m/z): 237 [M + H]+ |
| 8-6 | Br-(2-methylpyrimidin-5-yl) | N | Me | Free form | Colorless powder MS·APCI (m/z): 271, 273 [M + H]+ |

TABLE 9-continued

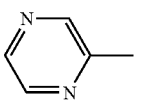

| Reference Example No. | R²—X— | B | R¹ | Salt | Physical properties, etc. |
|---|---|---|---|---|---|
| 8-7 | 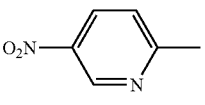 | N | Me | Free form | Colorless powder MS·APCI (m/z): 193 [M + H]+ |
| 8-8 | 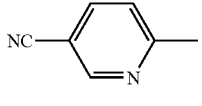 | N | CH₂OMe | Free form | Yellowish powder MS·APCI (m/z): 267 [M + H]+ |
| 8-9 | 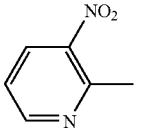 | N | CH₂OMe | Free form | Colorless powder MS·APCI (m/z): 247 [M + H]+ |
| 8-10 | 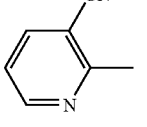 | N | CH₂OMe | Free form | Yellowish liquid MS·APCI (m/z): 267 [M + H]+ |
| 8-11 | 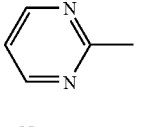 | N | CH₂OMe | Free form | Colorless liquid MS·APCI (m/z): 247 [M + H]+ |
| 8-12 | 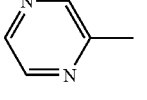 | N | CH₂OMe | Free form | Colorless liquid MS·APCI (m/z): 223 [M + H]+ |
| 8-13 | 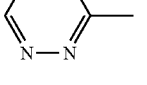 | N | CH₂OMe | Free form | Colorless liquid MS·APCI (m/z): 223 [M + H]+ |
| 8-14 | 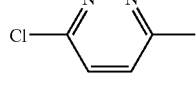 | N | CH₂OMe | Free form | Colorless powder MS·APCI (m/z): 223 [M + H]+ |
| 8-15 | 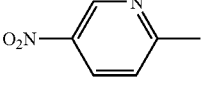 | N | CH₂OMe | Free form | Colorless powder MS·APCI (m/z): 257 [M + H]+ |
| 8-16 | 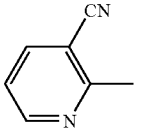 | N | CH₂OH | Free form | Yellowish powder MS·APCI (m/z): 235 [M + H]+ |
| 8-17 |  | N | CH₂OH | Free form | Colorless oil MS·APCI (m/z): 233 [M + H]+ |

TABLE 9-continued

R²—X—B—⟨ring⟩—R¹, NH₂

| Reference Example No. | R²—X— | B | R¹ | Salt | Physical properties, etc. |
|---|---|---|---|---|---|
| 8-18 | 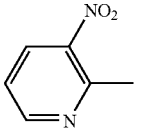 | N | CH₂OH | Free form | Yellowish oil MS•APCI (m/z): 253 [M + H]+ |
| 8-19 | 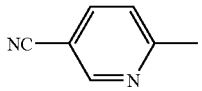 | N | CH₂OH | Free form | Colorless powder MS•APCI (m/z): 233 [M + H]+ |
| 8-20 | 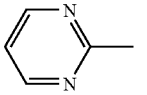 | N | CH₂OH | Free form | Colorless powder MS•APCI (m/z): 209 [M + H]+ |
| 8-21 | 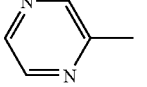 | N | CH₂OH | Free form | Colorless powder MS•APCI (m/z): 209 [M + H]+ |
| 8-22 | 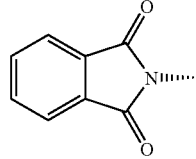 | CH | CH₂OH | HCl | Colorless solid Melting point: 265-267° C. |
| 8-23 | 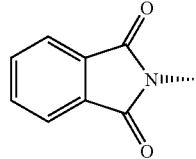 | CH | H | HCl | Colorless solid Melting point: >300° C. MS•APCI (m/z): 245 [M + H]+ |
| 8-24 | 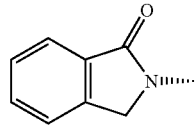 | CH | H | HCl | Colorless solid MS•APCI (m/z): 231 [M + H]+ |
| 8-25 | 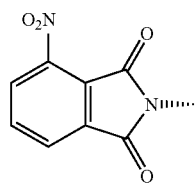 | CH | H | HCl | Colorless solid MS•APCI (m/z): 290 [M + H]+ |
| 8-26 |  | CH | H | HCl | Colorless solid MS•APCI (m/z): 259 [M + H]+ |

TABLE 9-continued

R²—X—B⟨R¹/NH₂⟩

| Reference Example No. | R²—X— | B | R¹ | Salt | Physical properties, etc. |
|---|---|---|---|---|---|
| 8-27 | pyridine-fused succinimide | CH | H | 2HCl | Colorless solid MS•APCI (m/z): 246 [M + H]+ |
| 8-28 | succinimide | CH | H | HCl | Colorless solid MS•APCI (m/z): 197 [M + H]+ |
| 8-29 | trifluoroacetamido-succinimide | CH | H | HCl | Colorless solid MS•APCI (m/z): 308 [M + H]+ |
| 8-30 | Cbz-amino-succinimide | CH | H | HCl | Colorless solid MS•APCI (m/z): 346 [M + H]+ |
| 8-31 | methoxycarbonylamino-succinimide | CH | H | HCl | Colorless solid MS•APCI (m/z): 270 [M + H]+ |
| 8-32 | methyl ester phthalimide | CH | H | HCl | Colorless solid MS•APCI (m/z): 303 [M + H]+ |
| 8-33 | pyrrolidinylcarbonyl phthalimide | CH | H | HCl | Colorless solid MS•APCI (m/z): 342 [M + H]+ |

TABLE 9-continued

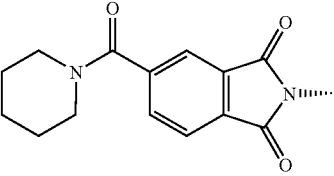

| Reference Example No. | R²—X— | B | R¹ | Salt | Physical properties, etc. |
|---|---|---|---|---|---|
| 8-34 | 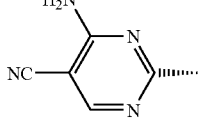 | CH | H | HCl | Colorless solid<br>MS·APCI (m/z):<br>356 [M + H]+ |
| 8-35 | 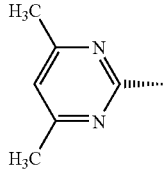 | CH | H | Free form | Colorless crystal<br>Melting point:<br>181-184° C.<br>MS·APCI (m/z): 218<br>[M + H] |
| 8-36 | 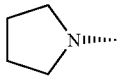 | CH | H | Free form | Slightly brownish oil<br>MS·APCI (m/z): 206<br>[M + H]+ |
| 8-37 |  | CH | H | 2HCl | Pale brownish crystal<br>Melting point:<br>>300° C.<br>MS·APCI (m/z): 169<br>[M + H] |
| 8-38 | 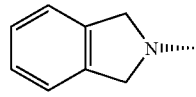 | CH | H | 2HCl | Colorless powder<br>MS·APCI (m/z): 185<br>[M + H] |
| 8-39 | 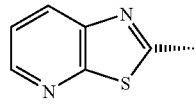 | CH | H | 2HCl | Colorless crystal<br>Melting point:<br>>300° C.<br>MS·APCI (m/z): 217<br>[M + H] |
| 8-41 | 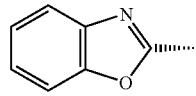 | CH | H | Free form | Yellowish powder<br>MS·APCI (m/z): 234<br>[M + H]+ |
| 8-42 | 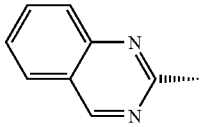 | CH | H | Free form | Colorless powder<br>MS·APCI (m/z): 217<br>[M + H]+ |
| 8-43 | | CH | H | Free form | Colorless powder<br>MS·APCI (m/z): 228<br>[M + H]+ |
| 8-44 | 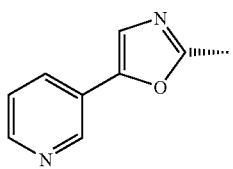 | CH | H | Free form | Colorless oil<br>MS·APCI (m/z): 244<br>[M + H]+ |

TABLE 9-continued

| Reference Example No. | R²—X— | B | R¹ | Salt | Physical properties, etc. |
|---|---|---|---|---|---|
| 8-45 | pyrrolidinyl | CH | Me | 2HCl | Colorless resin MS•APCI (m/z): 183 [M + H]+ |
| 8-46 | 2-(pyridin-2-yl)ethyl-N(CH₃)- | CH | Me | 3HCl | Colorless resin MS•APCI (m/z): 248 [M + H]+ |
| 8-47 | 4-acetylpiperazin-1-yl | CH | Me | | |
| 8-48 | 4-propanoylpiperazin-1-yl | CH | Me | | |
| 8-49 | 4-isobutyrylpiperazin-1-yl | CH | Me | | |
| 8-50 | 4-(3-methylbutanoyl)piperazin-1-yl | CH | Me | | |
| 8-51 | 4-(cyclopropylcarbonyl)piperazin-1-yl | CH | Me | | |
| 8-52 | 4-(cyclohexylcarbonyl)piperazin-1-yl | CH | Me | | |
| 8-53 | 4-phenylpiperazin-1-yl | CH | Me | | |
| 8-54 | morpholin-4-yl | CH | Me | 2HCl | |
| 8-55 | NC-CH₂-NH- | CH | Me | Free form | Oil |

TABLE 9-continued

R²—X—B⟨⟩—R¹/NH₂

| Reference Example No. | R²—X— | B | R¹ | Salt | Physical properties, etc. |
|---|---|---|---|---|---|
| 8-56 | H₃C—O—CH₂CH₂—N(CH₂CH₂—O—CH₃)— | CH | Me | Free form | Oil |
| 8-57 | (H₃C)₂N— | CH | Me | Free form | Powder MS•APCI (m/z): 257 |
| 8-58 | (H₃C)₂CH—NH— | CH | Me | Free form | Purified powder MS•APCI (m/z): 271 |
| 8-59 | H₃C—CH₂—CH(CH₃)—NH— | CH | Me | Free form | Purified oil MS•APCI (m/z): 285 |

TABLE 10

R²—X—B⟨⟩—R¹/NH₂

| Reference Example No. | R²—X— | B | R¹ | Salt | Physical properties, etc. |
|---|---|---|---|---|---|
| 9-1 | H₃C—CH₂—O—C(O)—N(piperazine)—C(O)—CH₃ | N | H | Free form | Colorless oil MS•APCI (m/z): 285 |
| 9-2 | morpholine-N—C(O)—CH₃ | N | H | Free form | Colorless oil MS•APCI (m/z): 214 |
| 9-3 | (H₃C)₂N—C(O)—CH₃ | N | H | Free form | Colorless oil MS•APCI (m/z): 172 |

TABLE 10-continued

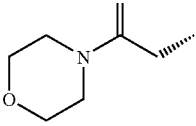

| Reference Example No. | R²—X— | B | R¹ | Salt | Physical properties, etc. |
|---|---|---|---|---|---|
| 9-4 | 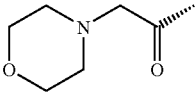 | CH | H | Free form | |
| 9-5 | 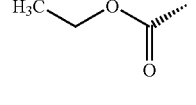 | CH | H | Free form | |
| 9-6 | 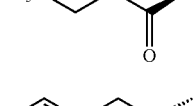 | CH | H | HCl | |
| 9-7 | 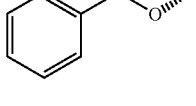 | CH | H | HCl | |
| 9-8 | 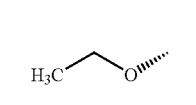 | CH | H | Free form | Oil MS•APCI (m/z): 268 |
| 9-9 | 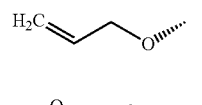 | CH | H | Free form | Oil MS•APCI (m/z): 130 |
| 9-10 | 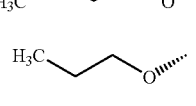 | CH | H | Free form | Oil MS•APCI (m/z): 144 |
| 9-11 | 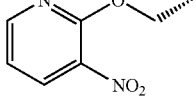 | CH | H | Free form | Oil MS•APCI (m/z): 156 |
| 9-12 | 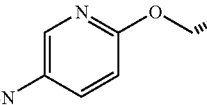 | CH | H | Free form | Oil MS•APCI (m/z): 174 |
| 9-13 | 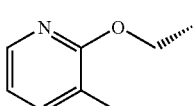 | CH | H | Free form | Oil MS•APCI (m/z): 158 |
| 9-14 | 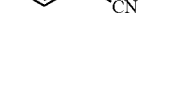 | CH | H | Free form | Yellowish crystal Melting point: 89-90° C. MS•APCI (m/z): 252 |
| 9-15 |  | CH | H | Free form | Pale yellowish crystal Melting point: 133-134° C. MS•APCI (m/z): 252 |
| 9-16 |  | CH | H | Free form | Colorless crystal Melting point: 64-65° C. MS•APCI (m/z): 232 |

TABLE 10-continued

| Reference Example No. | R²—X— | B | R¹ | Salt | Physical properties, etc. |
|---|---|---|---|---|---|
| 9-17 | 5-cyano-2-pyridyl-O-CH₂- | CH | H | Free form | Colorless crystal Melting point: 124-126° C. MS·APCI (m/z): 232 |
| 9-18 | 4-trifluoromethyl-2-pyrimidinyl-O-CH₂- | CH | H | Free form | Yellowish crystal Melting point: 46-49° C. MS·APCI (m/z): 276 |
| 9-19 | 2-pyrazinyl-O-CH₂- | CH | H | Free form | Colorless crystal Melting point: 57-59° C. MS·APCI (m/z): 208 |
| 9-20 | 3-chloro-2-pyrazinyl-O-CH₂- | CH | H | Free form | Pale yellowish oil MS·APCI (m/z): 242 and 244 |
| 9-21 | 5-fluoro-2-cyanophenyl-O-CH₂- | CH | H | Free form | Pale yellowish crystal Melting point: 115-116° C. MS·APCI (m/z): 249 |
| 9-22 | 2-methoxy-6-cyanophenyl-O-CH₂- | CH | H | Free form | Colorless crystal Melting point: 111-112° C. MS·APCI (m/z): 261 |
| 9-23 | 2-chloro-6-cyanophenyl-O-CH₂- | CH | H | Free form | Colorless crystal Melting point: 121-122° C. MS·APCI (m/z): 265 and 267 |
| 9-24 | 4-methyl-2-cyanophenyl-O-CH₂- | CH | H | Free form | Yellowish oil MS·APCI (m/z): 245 |
| 9-25 | 2-cyanophenyl-O-CH₂- | CH | H | Free form | Yellowish oil MS·APCI (m/z): 231 |
| 9-26 | 4-cyanophenyl-O-CH₂- | CH | H | Free form | Yellowish oil MS·APCI (m/z): 231 |

TABLE 10-continued

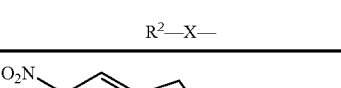

| Reference Example No. | R²—X— | B | R¹ | Salt | Physical properties, etc. |
|---|---|---|---|---|---|
| 9-27 | 2-nitrophenoxymethyl | CH | H | Free form | Yellowish oil<br>MS•APCI (m/z): 251 |
| 9-28 | 4-nitrophenoxymethyl | CH | H | Free form | Yellowish crystal<br>Melting point:<br>86-87° C.<br>MS•APCI (m/z): 251 |
| 9-29 | 5-bromo-2-pyrimidinyloxymethyl | CH | H | Free form | Colorless crystal<br>Melting point:<br>126-127° C.<br>MS•APCI (m/z): 286 and 288 |
| 9-30 | 5-cyano-2-pyridylthio | CH | H | Free form | Colorless crystal<br>Melting point:<br>325-326° C.<br>(decomposed) |
| 9-31 | 5-nitro-2-pyridylthio | CH | H | HCl | Yellowish crystal<br>Melting point:<br>328-329° C.<br>(decomposed) |
| 9-32 | 5-trifluoromethyl-2-pyridylthio | CH | H | HCl | Yellowish crystal<br>Melting point:<br>292-294° C. |
| 9-33 | 5-chloro-2-pyridylthio | CH | H | HCl | Colorless crystal<br>Melting point:<br>239-240° C. |

TABLE 11

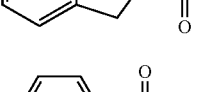

| Reference Example No. | R²—X— | B | R¹ | Salt | Physical properties, etc. |
|---|---|---|---|---|---|
| 10-1 | 5-nitroisoindolin-2-yl-carbonylmethylamino | CH | H | Free form | Yellowish oil<br>MS•APCI (m/z): 319 [M + H]+ |
| 10-2 | nicotinoylamino | CH | H | 2HCl | Colorless crystal<br>Melting point:<br>250-253° C. |

TABLE 11-continued

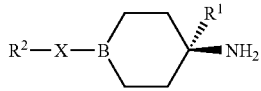

| Reference Example No. | R²—X— | B | R¹ | Salt | Physical properties, etc. |
|---|---|---|---|---|---|
| 10-3 | 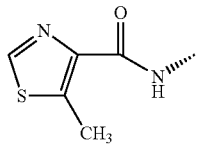 | CH | H | 2HCl | Colorless crystal Melting point: >300 ° C. MS·APCI (m/z): 220 [M + H]+ |
| 10-4 | 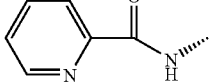 | CH | H | 2HCl | Colorless crystal Melting point: 277-278° C. |
| 10-5 | 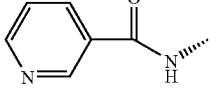 | CH | Me | Free form | Colorless liquid MS·APCI (m/z): 235 [M + H]+ |
| 10-6 | 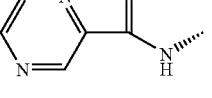 | CH | Me | Free form | Colorless crystal Melting point: 137-140° C. |
| 10-7 | 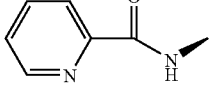 | CH | Me | Free form | Colorless crystal Melting point: 126-128° C. |
| 10-8 | 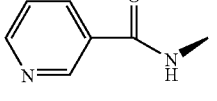 | CH | Me | Free form | Colorless liquid MS·APCI (m/z): 234 [M + H]+ |
| 10-9 | 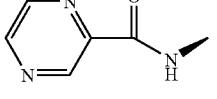 | CH | Me | Free form | Colorless liquid MS·APCI (m/z): 234 [M + H]+ |
| 10-10 | 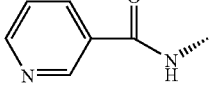 | CH | Me | Free form | Colorless crystal Melting point: 97-99° C. |
| 10-11 | 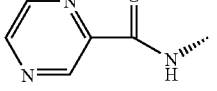 | CH | CH₂OH | 2HCl | Colorless solid MS·APCI (m/z): 250 [M + H]+ |
| 10-12 | 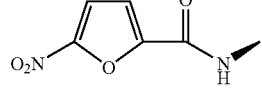 | CH | CH₂OH | HCl | Colorless solid MS·APCI (m/z): 251 [M + H]+ |
| 10-13 |  | CH | CH₂OH | HCl | Pale yellowish powder MS·APCI (m/z): 284 [M + H]+ |

TABLE 11-continued

| Reference Example No. | R²—X— | B | R¹ | Salt | Physical properties, etc. |
|---|---|---|---|---|---|
| 10-14 | pyrazine-C(O)-N(CH₃)- | CH | H | Free form | Colorless crystal Melting point: 60-62° C. |
| 10-15 | pyridin-2-yl-C(O)-N(CH₃)- | CH | H | Free form | Colorless crystal Melting point: 73-75° C. |
| 10-16 | pyridin-3-yl-C(O)-N(CH₃)- | CH | H | Free form | Colorless crystal Melting point: 82-83° C. |
| 10-17 | morpholino-CH₂CH₂-C(O)-N(CH₃)- | CH | H | Free form | Colorless resin MS·APCI (m/z): 270 [M + H]+ |
| 10-18 | H₃C-S(O)₂-N(CH₃)- | CH | H | Free form | Colorless crystal Melting point: 72-73° C. |
| 10-19 | H₃C-C₆H₄-S(O)₂-N(CH₃)- | CH | H | Free form | Colorless crystal Melting point: 91-94° C. |
| 10-20 | morpholino-C(O)-N(CH₃)- | CH | H | Free form | Colorless crystal Melting point: 97-99° C. |

The invention claimed is:

1. A method for inhibiting dipeptidylpeptidase IV activity by administering to a patient in need thereof an effective amount of a composition comprising an aliphatic nitrogen-containing 5-membered ring compound represented by the formula:

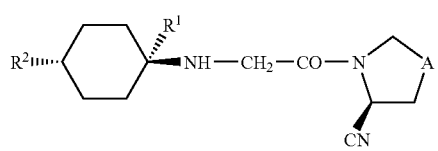

[I]

wherein symbols in the formula have the following meanings:

A: —CH₂— or —S—,

R¹: H, a lower alkyl group, a hydroxy lower alkyl group or a lower alkoxy lower alkyl group, R²: a cyclic group which may be substituted, where the cyclic group portion is a monocyclic or bicyclic heterocyclic group;

or a pharmaceutically acceptable salt thereof, and one or more pharmaceutically acceptable excipient or diluent.

2. A method for treatment of type 2 diabetes, which comprises administering to a patient in need thereof an effective amount of a composition comprising an aliphatic nitrogen-containing 5-membered ring compound represented by the formula:

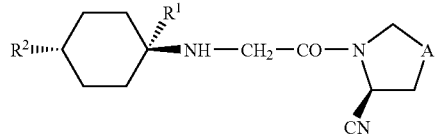

wherein symbols in the formula have the following meanings:

A: —CH$_2$— or —S—,

R$^1$: H, a lower alkyl group, a hydroxy lower alkyl group or a lower alkoxy lower alkyl group, R$^2$: a cyclic group which may be substituted, where the cyclic group portion is a monocyclic or bicyclic heterocyclic group;

or a pharmaceutically acceptable salt thereof, and one or more pharmaceutically acceptable excipient or diluent.

* * * * *